(12) United States Patent
Kim et al.

(10) Patent No.: US 7,652,009 B2
(45) Date of Patent: Jan. 26, 2010

(54) SUBSTITUTED HETEROCYCLES AND METHODS OF USE

(75) Inventors: Tae-Seong Kim, Thousand Oaks, CA (US); Steven Bellon, Wellesley, MA (US); Shon Booker, Thousand Oaks, CA (US); Noel D'Angelo, Thousand Oaks, CA (US); Celia Dominguez, Los Angeles, CA (US); Ingrid Fellows, Fresno, CA (US); Matthew Lee, Calabasas, CA (US); Longbin Liu, Thousand Oaks, CA (US); Elizabeth Rainbeau, Port Hueneme, CA (US); Aaron C. Siegmund, Ventura, CA (US); Andrew Tasker, Simi Valley, CA (US); Ning Xi, Thousand Oaks, CA (US); Yuan Cheng, Newbury Park, CA (US)

(73) Assignee: Amgem Inc., Thousand Oaks, CA (US)

( * ) Notice: Subject to any disclaimer, the term of this patent is extended or adjusted under 35 U.S.C. 154(b) by 486 days.

(21) Appl. No.: 11/289,659

(22) Filed: Nov. 29, 2005

(65) Prior Publication Data

US 2006/0252777 A1  Nov. 9, 2006

Related U.S. Application Data

(60) Provisional application No. 60/632,271, filed on Nov. 30, 2004.

(51) Int. Cl.
*A61K 31/506* (2006.01)
*C07D 401/02* (2006.01)
*C07D 239/22* (2006.01)

(52) U.S. Cl. .................. 514/252.04; 514/269; 544/238; 544/242; 544/298; 544/319

(58) Field of Classification Search ................. 544/224, 544/238, 242, 298, 319; 546/152; 514/252.04, 514/269
See application file for complete search history.

(56) References Cited

U.S. PATENT DOCUMENTS

| | | | |
|---|---|---|---|
| 3,755,332 | A | 8/1973 | Wasley et al. |
| 4,916,135 | A | 4/1990 | Effland et al. |
| 5,580,870 | A | 12/1996 | Barker et al. |
| 5,866,572 | A | 2/1999 | Barker et al. |
| 5,965,563 | A | 10/1999 | Buzzetti et al. |
| 6,143,764 | A | 11/2000 | Kubo et al. |
| 6,265,398 | B1 | 7/2001 | Braun et al. |
| 6,313,129 | B1 | 11/2001 | Uckun et al. |
| 6,358,962 | B2 | 3/2002 | Uckun et al. |
| 6,399,602 | B1 | 6/2002 | Barker et al. |
| 6,469,013 | B2 | 10/2002 | Uckun et al. |
| 6,495,556 | B2 | 12/2002 | Uckun et al. |
| 6,573,289 | B1 | 6/2003 | Tasaka et al. |
| 6,897,214 | B2 | 5/2005 | Barker et al. |
| 2003/0165873 | A1 | 9/2003 | Come et al. |
| 2004/0053908 | A1 | 3/2004 | Funahashi et al. |
| 2004/0209905 | A1 | 10/2004 | Kubo et al. |
| 2004/0242603 | A1 | 12/2004 | Fujiwara et al. |
| 2005/0245547 | A1 | 11/2005 | Kim et al. |

FOREIGN PATENT DOCUMENTS

| | | |
|---|---|---|
| EP | 860433 A1 | 8/1998 |
| EP | 1411046 A1 | 4/2004 |
| EP | 1415987 A1 | 5/2004 |
| EP | 1 548 008 A1 | 6/2005 |
| JP | 63-145272 | 6/1988 |
| JP | 11-158149 | 6/1999 |
| WO | WO 96/23774 | 8/1996 |
| WO | WO 96/29301 | 9/1996 |
| WO | WO 96/29305 | 9/1996 |
| WO | WO 97/03069 | 1/1997 |
| WO | WO97/22596 | 6/1997 |
| WO | WO98/37079 | 8/1998 |
| WO | WO 99/35132 | 7/1999 |
| WO | WO 99/54309 | 10/1999 |
| WO | WO 99/61428 | 12/1999 |
| WO | WO 00/10981 | 3/2000 |
| WO | WO 00/47212 | 8/2000 |
| WO | WO00/50405 | 8/2000 |
| WO | WO 00/56720 | 9/2000 |
| WO | WO 00/61580 | 10/2000 |
| WO | WO 01/21594 | 3/2001 |
| WO | WO 01/70673 | 9/2001 |
| WO | WO 01/70734 | 9/2001 |

(Continued)

OTHER PUBLICATIONS

Sathi, Garima. New Quinolines as Potential CNS Agents. Arch. Pharm. (Weinheim). 316 (1983) 767-772.*

(Continued)

*Primary Examiner*—Kamal A Saeed
*Assistant Examiner*—Samantha L Shterengarts

(57) ABSTRACT

Selected compounds are effective for prophylaxis and treatment of diseases, such as HGF mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

25 Claims, No Drawings

FOREIGN PATENT DOCUMENTS

| | | |
|---|---|---|
| WO | WO 02/22607 | 3/2002 |
| WO | WO 02/22608 | 3/2002 |
| WO | WO 02/30924 | 4/2002 |
| WO | WO 02/076976 | 10/2002 |
| WO | WO02/098426 | 12/2002 |
| WO | WO03/004472 | 1/2003 |
| WO | WO 03/040108 | 5/2003 |
| WO | WO 03/040109 | 5/2003 |
| WO | WO 03/064413 | 8/2003 |
| WO | WO 03/082272 | 10/2003 |
| WO | WO2004/018430 | 3/2004 |
| WO | WO 2004/029045 | 4/2004 |
| WO | WO2004/030672 | 4/2004 |
| WO | WO2004/037784 | 5/2004 |
| WO | WO2004/043379 | 5/2004 |
| WO | WO2004/046133 | 6/2004 |
| WO | WO 2004/078114 | 9/2004 |
| WO | WO2004/083235 | 9/2004 |
| WO | WO 2004/085425 | 10/2004 |
| WO | WO 2004/098604 | 11/2004 |
| WO | WO2005/021553 | 3/2005 |
| WO | WO2005/030140 | 4/2005 |
| WO | WO2005/037285 | 4/2005 |
| WO | WO2005/070891 | 8/2005 |
| WO | WO2005/080377 | 9/2005 |

OTHER PUBLICATIONS

Remington, Joseph P., The Science and Practice of Pharmacy, 20th Ed. (2000), 218-220.*
Anderson et al., "Involvement of the protein tyrosine kinase p56$^{lck}$ in T cell signaling and thymocyte development," Advances in Immunology, 56:151-178 (1994).
Appleby et al., "Defective T cell receptor signaling in mice lacking the thymic isoform of p59$^{fyn}$,"Cell, 70:751-763 (1992).
Asami et al., "Purification and characterization of hepatocyte growth factor from injured liver of carbon tetrachloride-treated rats," Journal of Biochemistry, 109:8-13 (1991).
Asano et al., "Silver halide color photographic materials," Abstract 113:181318 (1990).
Boehm et al., "Antiangiogenic therapy of experimental cancer does not induce acquired drug resistance," Nature, 390:404-407 (1997).
Bolen et al., "Leukocyte protein tyrosine kinases: Potential targets for drug discovery," Annu. Rev. Immunology, 15:371-404 (1997).
Brazhko et al., "Investigations of the biological activity 4-thioquinolines." Abstract 135:189745.
Bussolino et al., "Hepatocyte growth factor is a potent angiogenic factor which stimulates endothelial cell motility and growth," The Journal of Cell Biology, 119(3):629-641 (1992).
Chan et al., "Isoforms of human HGF and their biological activities," Hepatocyte Growth Factor-Scatter Factor (HGF-SF) and the C-Met Receptor, pp. 67-79, Goldberg and Rosen (Eds.), Birkhauser Verlag Basel, Switzerland (1993).
Chatterjee, A.K., "A note on 4-Aminoquinolines. III. Some 4-(quinolylamino)quinolines," Science and Culture 23:195 (1957).
Cockerill et al., "Indazolylamino quinazolines and pyridopyrimidines as inhibitors of the EGFr and C-erbB-2," Bioorganic & Medicinal Chemistry Letters, 11:1401-1405 (2001).
Di Renzo et al., "Selective expression of the Met/HGF receptor in human central nervous system microglia, Oncogene," 8:219-222 (1992).
Gibson et al., "Epidermal growth factor receptor tyrosine kinase: Structure-activity relationships and antitumor activity of novel quinazolines," Bioorganic & Medicinal Chemistry Letters, 7(21):2723-2728 (1997).
Giordano et al., "Transfer of motogenic and invasive response to scatter factor/hepatocyte growth factor by transfection of human MET protooncogene," Proceedings of the National Academy of Sciences, USA, 90:649-653 (1993).

Goldman et al, "Defective expression of p56lck in an infant with severe combined immunodeficiency," Journal of Clinical Investigations, 102(2):421-429 (1998).
Han et al., "Characterization of the DNF15S2 locus on human chromosome 3: Identification of a gene coding for four kringle domains with homology to hepatocyte growth factor," Biochemistry, 30:9768-9780 (1991).
Igawa et al., "Hepatocyte growth factor is a potent mitogen for cultured rabbit renal tubular epithelial cells," Biochemical and Biophysical Research Communications, 174(2):831-838 (1991).
Jeffers et al., "Hepatocyte growth factor/scatter factor-Met signaling in tumorigenicity and invasion/metastasis," J. Mol. Med., 74:505-513 (1996).
Kane et al., "Signal transduction by the TCR for antigen," Current Opinion in Immunology, 12:242-249 (2000).
Kasai et al., "Flexible coordination networks with fluorinated backbones, remarkable ability for induced-fit enclathration of organic molecules," Journal of American Chemical Society, 122:2140-2141 (2000).
Konishi et al., "Preparation of thioquinoline derivatives as antibacterial agents for *Helicobacter pylori*," Chemical Abstracts 125:247631. 1 page.
Lempert-Sreter et al., "The synthesis of di(1-isoquinolinyl) and di(4-quinazolinyl) disulfides form 1(2H)-isoquinolinethiones and 4(3H)-quinazolinethiones, respectively, with tosyl chloride and sodium ethoxide," Acta Chemica Hungarica, 112(1):83-87 (1983).
Makisumi, Yasuo, "The Thio-claisen rearrangement of ally 4-quinolyl sulfides," Tetrahedron Letters, 51:6399-6403 (1966).
Maslankiewicz, M.J., "Reactions of β- and γ-quinolinyl sulfides with a nitrating mixture," Polish Journal of Chemistry, 68(12):2545-2552 (1994).
Matsumoto et al., "Hepatocyte growth factor is a potent stimulator of human melanocyte DNA synthesis and growth," Biochemical and Biophysical Research Communications, 176(1):45-51 (1991).
Matsunaga et al., "C$_{17,20}$-lyase inhibitors. Part 2:Design, synthesis and structure-activity relationships of (2-naphthylmethyl)-1H-imidazoles as novel C$_{17,20}$-lyase inhibitors," Bioorganic & Medicinal Chemistry, 12:4313-4336 (2004).
Maulik et al., "Role of the hepatocyte growth factor receptor, c-Met, in oncogenesis and potential for therapeutic inhibition," Cytokine & Growth Factor Reviews, 13:41-59 (2002).
Montesano et al., "Induction of epithelial tubular morphogenesis in vitro by fibroblast-derived soluble factors," Cell, 66:697-711 (1991).
Monti et al., IV. Abstract 55:2681. 1 page.
Moszew et al., "Thermal reactions of γ-thiols in pyridine and quinoline series." Abstract 77:164418. 1 page.
Nakamura et al., "Partial purification and characterization of hepatocyte growth factor from serum of hepatectomized rats," Biochemical and Biophysical Research Communications, 122(3):1450-1459 (1984).
Naldini et al., "Scatter factor and hepatocyte growth factor are indistinguishable ligands for the *MET* receptor," EMBO Journal, 10:2867-2878 (1991).
Park et al., "Sequence of *MET* protooncogene cDNA has features characteristic of the tyrosine kinase family of growth-factor receptors," Proceedings of the National Academy of Sciences, USA, 84:6379-6383 (1987).
Renfrew, Alice G., "Studies in the Quinoline Series. IV. Quinolyl Mercaptans and Sulfides," J. American Chemical Society, 1433-1436 (1946).
Di Renzo et al., "Overexpression of the c-MET/HGF receptor gene in human thyroid carcinomas," Oncogene, 7:2549-2553 (1992).
Rubin et al., "A broad-spectrum human lung fibroblast-derived mitogen is a variant of hepatocyte growth factor," Proceedings of the National Academy of Sciences, USA, 88:415-419 (1991).
Sinyak et al., "The synthesis and biological properties of the derivatives of 4-heterylmercaptoquinazoline," Khimiko-Farmatsevticheskii Zhurnal, 20(2), 168-171 (1986). Abstract 104:199594.
Solbreux et al., "Extrahepatic bile duct growth in mice repeatedly injected with human normal serum, IgA-deficient serum or purified secretory IgA", Hepatology, 13:735-742 (1991).

Soriano et al., "Targeted disruption of the c-*src* proto-oncogene leads to osteopetrosis in mice," Cell, 64:693-702 (1991).

Stern et al., "Epithelial scatter factor and development of the chick embryonic axis," Development 110:1271-1284(1990).

Stoker et al., "Scatter factor is a fibroblast-derived modulator of epithelial cell mobility," Nature, 327:239-242 (1987).

Thakore, P.V. et al., "Studies in the synthesis of quinoline derivatives. Part VIII. Synthesis of 4:3'-methylenebis(2,2'-dichloro-4'-methylquinoline) derivatives," Journal of the Indian Chemical Society, 54(12):1204-1206 (1977).

Turner et al., "Signalling through the high-affinity IgE receptor FcεRI," Nature, 402:B24-B30 (1999).

Vicentini et al., "Fgr deficiency results in defective eosinophil recruitment to the lung during allergic airway inflammation," The Journal of Immunology, 168:6446-6454 (2002).

Weidner et al., "Scatter Factor: Molecular characteristics and effect on the invasiveness of epithelial cells," The Journal of Cell Biology, 111:2097-2108 (1990).

Wyszomirski et al., "Conformations of monosubstituted and disubstituted 3,4'-, 3,3'- and 4,4'-diquinolinyl sulfides studied by NMR spectroscopy," Phosphorus, Sulfur, and Silicon, 95-96:415-416 (1994).

Zhang et al., "Synthesis and antimalarial activity of 2-dialkylaminomethyl-4-(heterocyclic amino)-5,6,7,8-tetrahydronaphthol derivatives." Abstract 103:87753. 1 page.

Zhang et al., "Synthesis and SAR of potent EGFR/erbB2 dual inhibitors," Bioorganic & Medicinal Chemistry Letters, 14:111-114 (2004).

Breier et al., "The role of vascular endothelial growth factor in blood vessel formation," Trends in Cell Biology, 6:454-456 (1996).

Paolo M. Comoglio, "Structure, biosynthesis and biochemical properties of the HGF receptor in normal and malignant cells," Hepatocyte Growth Factor-Scatter Factor (HGF-SF) and the C-*Met* Receptor, eds. Goldberg and Rosen, Birkhauser Verlag Basel, Switzerland, 131-165 (1993).

Connell et al., "Patent focus on cancer chemotherapeutics. II Angiogenesis agents: Apr. 2000-Sep. 2000" Expert Opinion on Therapeutic Patents, 11(1):77-114 (2001).

Kubo et al., "Synthesis and Structure-Activity Relationship for New Series of 4-Phenoxyquinoline Derivatives as Specific Inhibitors of Platelet-Derived Growth Factor Receptor Tyrosine Kinase," Bioorganic & Medicinal Chemistry 11, 5117-5133 (2003).

Kamel et al., "New 4-substituted phenoxyquinolines of possible antimicrobial activity", Egyptian Journal of Pharmaceutical Sciences, 38(1-3), 61-69 (1997).

Wright et al., "Anilinoquinazoline Inhibitors of Fructose 1,6-Bisphosphatase Bind at a Novel Allosteric Site: Synthesis, In Vitro Characterization, and X-ray Crystallography," Journal of Medicinal Chemistry, (45), 3865-3877 (2002).

Steck et al., "Pyridazines. VI. Some 6-Substituted 3(2H)pyridazinones (1)" Journal of Heterocyclic Chemistry, 11 (5), 755-761, (1974).

Okushima et al., "A Novel Class of Cardiotonics. Synthesis and Pharmacological Properties of [4-(Substituted-amino)phenyl]pyridazinones and Related Derivatives," Journal of Medicinal Chemistry 30(7) 1157-1161 (1987).

Okushima et al., "A new class of cardiotonics. Structure-activity relationships of pyridazinones and pharmacological properties of MCI-154," database accession No. 1993:93799 compounds with RN 145917-30-2 Chemical Abstracts Service; Research and Development Review—Mitsubishi Kasei Corporation 1992, 6(2), 1 page.

A.H. Abadi and H.A. Al-Khamees, "3-Cyano-4,6 disubstituted-2(1H)-imino or oxopyridines: New Antineoplastic Agents with High Selectivity Towards Leukemia Cell Lines," Arch. Pharm. Pharm. Med. Chem 331 (10), 319-324, (1998).

Omar et al., "Synthesis of some new 4-substituted anilinoquinolines of expected biological activity" Chemical Abstracts Service, Database accession No. 1999-458494 Egyptian Journal of Pharmaceutical Sciences, Volume Date 1997, 38(4-6), (1998) 1 page.

* cited by examiner

SUBSTITUTED HETEROCYCLES AND METHODS OF USE

FIELD OF THE INVENTION

This invention is in the field of pharmaceutical agents and specifically relates to compounds, compositions, uses and methods for treating cancer.

BACKGROUND OF THE INVENTION

Protein kinases represent a large family of proteins which play a central role in the regulation of a wide variety of cellular processes, maintaining control over cellular function. A partial list of such kinases includes ab1, Akt, bcr-ab1, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor" (VEGF; originally termed 'Vascular Permeability Factor", VPF), along with its cellular receptors (see G. Breier et al., Trends in Cell Biology, 6:454-456 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors which grow beyond a diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11:77-114 (2001).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

The hepatocyte growth factor receptor ("c-Met") is a unique receptor tyrosine kinase shown to be overexpressed in a variety of malignancies. c-Met typically comprises, in its native form, a 190-kDa heterodimeric (a disulfide-linked 50-kDa α-chain and a 145-kDa β-chain) membrane-spanning tyrosine kinase protein (Proc. Natl. Acad. Sci. USA, 84:6379-6383 (1987)). c-Met is mainly expressed in epithelial cells and stimulation of c-Met leads to scattering, angiogenesis, proliferation and metastasis. (See Cytokine and Growth Factor Reviews, 13:41-59 (2002)).

The ligand for c-Met is hepatocyte growth factor (also known as scatter factor, HGF and SF). HGF is a heterodimeric protein secreted by cells of mesodermal origin (Nature, 327: 239-242 (1987); J. Cell Biol., 111:2097-2108 (1990)).

Various biological activities have been described for HGF through interaction with c-met (Hepatocyte Growth Factor-Scatter Factor (HGF-SF) and the c-Met Receptor, Goldberg and Rosen, eds., Birkhauser Verlag-Basel, 67-79 (1993). The biological effect of HGF/SF may depend in part on the target cell. HGF induces a spectrum of biological activities in epithelial cells, including mitogenesis, stimulation of cell motility and promotion of matrix invasion (Biochem. Biophys. Res. Comm., 122:1450-1459 (1984); Proc. Natl. Acad. Sci. U.S.A., 88:415-419 (1991)). It stimulates the motility and invasiveness of carcinoma cells, the former having been implicated in the migration of cells required for metastasis. HGF can also act as a "scatter factor", an activity that promotes the dissociation of epithelial and vascular endothelial cells (Nature, 327:239-242 (1987); J. Cell Biol., 111:2097-2108 (1990); EMBO J., 10:2867-2878 (1991); Proc. Natl. Acad. Sci. USA, 90:649-653 (1993)). Therefore, HGF is thought to be important in tumor invasion (Hepatocyte Growth Factor-Scatter Factor (HGF-SF) and the C-Met Receptor, Goldberg and Rosen, eds., Birkhauser Verlag-Basel, 131-165 (1993)).

HGF and c-Met are expressed at abnormally high levels in a large variety of solid tumors. High levels of HGF and/or c-Met have been observed in liver, breast, pancreas, lung, kidney, bladder, ovary, brain, prostate, gallbladder and myeloma tumors in addition to many others. The role of HGF/c-Met in metastasis has been investigated in mice using cell lines transformed with HGF/c-Met (J. Mol. Med., 74:505-513 (1996)). Overexpression of the c-Met oncogene has also been suggested to play a role in the pathogenesis and progression of thyroid tumors derived from follicular epithelium (Oncogene, 7:2549-2553 (1992)). HGF is a morphogen (Development, 110:1271-1284 (1990); Cell, 66:697-711 (1991)) and a potent angiogenic factor (J. Cell Biol., 119:629-641 (1992)).

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor. Angiogenesis can be stimulated by HGF, as well as vascular endothelial growth factor (VEGF) and basic fibroblast growth factor (bFGF).

Angiogenesis, the process of sprouting new blood vessels from existing vasculature and arteriogenesis, the remodeling of small vessels into larger conduit vessels are both physiologically important aspects of vascular growth in adult tissues. These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies. The inhibition of vascular growth in these contexts has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Treatment of malaria and related viral diseases may also be mediated by HGF and cMet.

Elevated levels of HGF and c-Met have also been observed in non-oncological settings, such as hypertension, myocardial infarction and rheumatoid arthritis. It has been observed that levels of HGF increase in the plasma of patients with hepatic failure (Gohda et al., supra) and in the plasma (Hepatol., 13:734-750 (1991)) or serum (J. Biochem., 109:8-13 (1991)) of animals with experimentally induced liver damage. HGF has also been shown to be a mitogen for certain cell types, including melanocytes, renal tubular cells, keratinocytes, certain endothelial cells and cells of epithelial origin (Biochem. Biophys. Res. Commun., 176:45-51 (1991); Biochem. Biophys. Res. Commun., 174:831-838 (1991); Biochem., 30:9768-9780 (1991); Proc. Natl. Acad. Sci. USA, 88:415-419 (1991)). Both HGF and the c-Met protooncogene have been postulated to play a role in microglial reactions to CNS injuries (oncogene, 8:219-222 (1993)).

Metastatic SCC cells overexpress c-Met and have enhanced tumoregenesis and metastasis in vivo [G. Gong et al., Oncogene, 23:6199-6208 (2004)]. C-Met is required for tumor cell survival [N. Shinomiya et al., Cancer Research, 64:7962-70 (2004)]. For a general review see C. Birchmeier et al., Nature Reviews/Molecular Biology 4:915-925 (2003).

In view of the role of HGF and/or c-Met in potentiating or promoting such diseases or pathological conditions, it would be useful to have a means of substantially reducing or inhibiting one or more of the biological effects of HGF and its receptor. Thus a compound that reduces the effect of HGF would be a useful compound. Compounds of the current invention have not been previously described as inhibitors of angiogenesis such as for the treatment of cancer.

Kirin Japanese patent application JP11158149, published 28 Nov. 1997, describes substituted phenyl compounds. Kirin publication WO 00/43366 describes substituted phenyl compounds. Kirin publication WO 03/000660 describes substituted phenyl compounds. Substituted quinolines are described in U.S. Pat. No. 6,143,764. WO 02/32872 describes substituted quinolines. Patent Application WO 00/47212 describes substituted quinazoline derivatives. Patent Application WO 98/37079 describes substituted N-heterocyclic compounds. Kubo et al, Biorg. Med. Chem., 11:5117-33 (2003) describes phenoxyquinoline derivatives. Patent Application WO 04/46133, published 3 Jun. 2004, describes amino-heterocycles for treating pain. Patent Application WO 03/004472, published 16 Jan. 2003, describes pyrazine-2-carboxamides. JP63145272, published 17 Jun. 1988, describes 4,5-dihydro-6-(4-substituted phenyl)-3(2H)-pyridazinones. Kamel, et al., Egyptian J. of Pharm. Sci., 38:61-69 (1997) describes 4-substituted phenoxyquinolines. Patent Application WO 04/18430, published 4 Mar. 2004, describes quinoline derivatives. Patent Application WO 02/32872, published 25 Apr. 2002, describes urea derivatives. Patent Application WO 04/37784, published 6 May 2004, describes substituted pyrrolidones. Patent Application WO 00/50405 published 31 Aug. 2000, describes quinoline-6-carboxamides. Patent Application WO 04/083235, published 30 Sep. 2004, describes azaheterocyclyl aromatic compounds.

Compounds of the current invention have not been described as inhibitors of c-Met such as for the treatment of cancer.

DESCRIPTION OF THE INVENTION

A class of compounds useful in treating cancer and angiogenesis is defined by Formula I $$R^1—X—W—A—Y—R \qquad I$$

wherein R is selected from substituted or unsubstituted aryl, substituted or unsubstituted heterocyclyl, substituted or unsubstituted cycloalkyl, substituted or unsubstituted cycloalkenyl, H, —OH, alkylamino, substituted or unsubstituted alkyl, and substituted or unsubstituted alkenyl and substituted or unsubstituted alkynyl;

wherein $R^1$ is

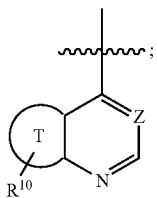

wherein ring T is selected from phenyl and 5-6-membered heteroaryl; wherein Z is selected from N or CH; wherein $R^{10}$ is one or more substituents selected from $C_{1-6}$-alkoxy, $C_{1-6}$-haloalkoxy, $C_{1-6}$-alkylamino-$C_{1-6}$-alkoxy, aryl-$C_{1-6}$-alkoxy, heterocyclyl-$C_{1-6}$-alkoxy, cycloalkyl-$C_{1-6}$-alkoxy, heterocyclyl-$C_{1-6}$-(hydroxyalkoxy), cycloalkyl-$C_{1-6}$-(hydroxyalkoxy), aryl-$C_{1-6}$-(hydroxyalkoxy), $C_{1-6}$-alkoxyalkoxy, aryloxy-$C_{1-6}$-alkoxy, heterocyclyloxy-$C_{1-6}$-alkoxy, cycloalkyloxy-$C_{1-6}$-alkoxy, aryloxy, heterocyclyloxy, and cycloalkyloxy;

wherein W is an substituted or unsubstituted aryl or substituted or unsubstituted 5-6-membered heteroaryl;

wherein A is an substituted or unsubstituted 5-7-membered nitrogen-containing heterocyclyl;

wherein X is selected from O, S, $NR^2$ and $CR^3R^4$;

wherein Y is selected from a direct bond, $—NR^a(CR^3R^4)_p—$, $—O(CR^3R^4)_p—$, $—(CR^3R^4)_p—$, $—S(=O)_t(CR^3R^4)_p—$, $—CO_2—$, $—C(=O)NH—$ and $—C(=O)(CR^3R^4)_p—$; wherein Y is in either direction;

wherein $R^a$ is selected from H, alkyl, heterocyclyl, aryl, arylalkyl, heterocyclylalkyl, cycloalkyl, cycloalkylalkyl, alkenyl, alkynyl, $R^5R^5N—(C=O)—$, and $R^5—(=O)—$; wherein $R^a$ is optionally substituted;

wherein $R^2$ is selected from H, alkyl, haloalkyl, aryl, heterocyclyl, arylalkyl, heterocyclylalkyl, cycloalkyl, cycloalkylalkyl, hydroxyalkyl, alkoxyalkyl, alkylaminoalkyl, alkylthioalkyl, alkenyl, alkynyl and $R^5$-carbonyl;

wherein $R^3$ and $R^4$ is each independently selected from H, alkyl, aryl, heterocyclyl, arylalkyl, heterocyclylalkyl, haloalkyl, cycloalkyl, cycloalkylalkyl, $R^6$ and alkyl substituted with $R^6$;

wherein $R^5$ is selected from H, alkyl, haloalkyl, hydroxyalkyl, alkoxyalkyl, alkylaminoalkyl, alkylthioalkyl, arylalkyl, heterocyclylalkyl, cycloalkylalkyl, aryl, heterocyclyl, alkenyl, alkynyl and cycloalkyl;

wherein $R^{5a}$ is selected from H, alkyl, haloalkyl, arylalkyl, heterocyclylalkyl, cycloalkylalkyl, aryl, heterocyclyl, hydroxyalkyl, alkoxyalkyl, alkylaminoalkyl, alkylthioalkyl, alkenyl, alkynyl and cycloalkyl;

wherein $R^6$ is selected from cyano, $—OR^2$, $—SR^2$, halo, $—SO_2R^2$, $—C(=O)R^2$, $—SO_2NR^2R^5$, $—NR^5C(=O)OR^2$, $—NR^5C(=O)NR^5R^2$, $—NR^5C(=O)R^2$, $—CO_2R^2$, $—C(=O)NR^2R^5$ and $—NR^2R^5$;

wherein $R^{6a}$ is selected from cyano, $—OR^2$, $—SR^2$, halo, $—SO_2R^2$, $—C(=O)R^2$, $—SO_2NR^2R^5$, $—NR^5C(=O)OR^2$, $—NR^5C(=O)NR^5R^2$, $—NR^5C(=O)R^2$, $—CO_2R^2$, $—C(=O)NR^2R^5$ and $—NR^2R^5$;

wherein p is 0, 1, 2, or 3; and wherein t is 0, 1 or 2;

wherein each alkyl, aryl, heteroaryl, cycloalkyl, alkenyl, alkynyl, heterocyclyl, and alkoxy moiety of any R, $R^1$, $R^2$, $R^3$, $R^4$, $R^5$ and $R^a$ is optionally substituted with one or more groups selected from halo, $R^{6a}$, $—NH_2$, $—OR^{5a}$, $—CO_2H$, $(C_1-C_6)$alkylamino, $(C_1-C_6)$alkyl, $(C_3-C_6)$cycloalkyl, $(C_1-C_6)$haloalkyl, di$(C_1-C_6)$alkylamino, $(C_1-C_6)$alkylamino-$(C_1-C_6)$alkyl, $(C_1-C_6)$hydroxyalkylamino, $(C_1-C_6)$alkylamino-$(C_1-C_6)$alkylamino, phenyl, and heterocyclyl;

and pharmaceutically acceptable derivatives thereof.

The invention also relates to compounds of Formula I provided the compound is not 6,7-dimethoxy-4-[[6-methyl-2-(3-thienyl)-3-pyridinyl]oxy]-quinoline, provided W is not thiadiazole-3-yl when A is piperazin-4-yl, X is O, Y is —C(=O)NH—, R is 3,5-bis(trifluoromethyl)phenyl and $R^1$ is 6,7-dimethoxyquinolin-4-yl;

provided W is not 2,3-dimethylpyridyl when A is pyrid-2-yl or pyrid-3-yl, X is O, Y is a direct bond and R is methyl or H;

provided W is not 2,3-dimethylpyridyl when A is thiazol-2-yl, X is O, Y is a direct bond and R is methyl or H;

provided W is not 2-methylpyridyl when A is thiazol-2-yl or 3-thienyl, X is O, Y is a direct bond and R is H;

provided W is not 2-methylthiopyridyl when A is pyrid-3-yl, X is O, Y is a direct bond and R is H;

provided W is not 2-methylpyridyl when A is pyrazol-4-yl, pyrazol-3-yl, isoxazol-5-yl or pyrazol-5-yl, X is O, Y is a direct bond and R is methyl;

provided W is not 2,3-dimethylpyridyl when A is pyrazol-4-yl, X is O, Y is a direct bond and R is H;

provided W is not 2,3-dimethylpyridyl when A is 6-oxo-pyrid-3-yl, X is O, Y is a direct bond and R is H;

provided W is not 2,3-dimethylpyridyl when A is pyrimidin-2-yl, X is O, Y is a direct bond and R is H;

provided W is not 2-methylpyridyl when A is pyrimidin-5-yl, X is O, Y is a direct bond and R is H;

provided W is not 2-methylpyridyl when A is pyridyl, X is O, Y is a direct bond and R is H;

provided W is not 2-iodophenyl when A is imidazol-1-yl, X is O, Y is a direct bond and R is H;

provided W is not dimethylphenyl or methylphenyl, when A is pyrid-3-yl, pyrid-2-yl or isoxazol-5-yl, X is O, Y is a direct bond and R is H;

provided W is not ethoxycarbonylphenyl when A is pyrrol-1-yl, X is O, Y is a direct bond and R is H;

provided A is not 3,4-dihydro-2-oxo-1H-quinazolin-3-yl, morpholin-1-yl or 1-imidazolyl when W is phenyl, X is O, Y is a direct bond and R is H; and provided A is not 2-amino-3-cyano-pyrid-6-yl, 2-oxo-3-cyano-pyrid-6-yl or 2-thio-3-cyano-pyrid-6-yl when W is phenyl, X is O, Y is a direct bond and R is optionally substituted phenyl.

The invention also relates to compounds of Formula I'

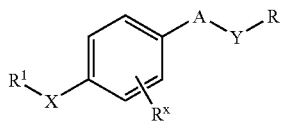

wherein R is selected from substituted or unsubstituted aryl, substituted or unsubstituted heterocyclyl, substituted or unsubstituted cycloalkyl, substituted or unsubstituted cycloalkenyl, H, —OH, alkylamino, substituted or unsubstituted alkyl, and substituted or unsubstituted alkenyl and substituted or unsubstituted alkynyl;

wherein $R^1$ is

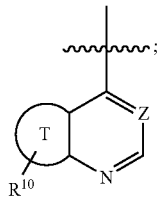

wherein ring T is selected from phenyl and 5-6-membered heteroaryl; wherein Z is selected from N or CH; wherein $R^{10}$ is one or more substituents selected from $C_{1-6}$-alkoxy, $C_{1-6}$-haloalkoxy, $C_{1-6}$-alkylamino-$C_{1-6}$-alkoxy, aryl-$C_{1-6}$-alkoxy, heterocyclyl-$C_{1-6}$-alkoxy, cycloalkyl-$C_{1-6}$-alkoxy, heterocyclyl-$C_{1-6}$-(hydroxyalkoxy), cycloalkyl-$C_{1-6}$-(hydroxyalkoxy), aryl-$C_{1-6}$-(hydroxyalkoxy), $C_{1-6}$-alkoxyalkoxy, aryloxy-$C_{1-6}$-alkoxy, heterocyclyloxy-$C_{1-6}$-alkoxy, cycloalkyloxy-$C_{1-6}$-alkoxy, aryloxy, heterocyclyloxy, and cycloalkyloxy;

wherein A is an substituted or unsubstituted 5-7-membered nitrogen-containing heterocyclyl;

wherein X is selected from O, S, NR and $CR^3R^4$;

wherein Y is selected from a direct bond, $—NR^a(CR^3R^4)_p—$, $—O(CR^3R^4)_p—$, $—(CR^3R^4)_p—$, $—S(=O)_t(CR^3R^4)_p—$, $—CO_2—$, $—C(=O)NH—$ and $—C(=O)(CR^3R^4)_p—$; wherein Y is oriented in either direction;

wherein $R^a$ is selected from H, alkyl, heterocyclyl, aryl, arylalkyl, heterocyclylalkyl, cycloalkyl, cycloalkylalkyl, alkenyl, alkynyl, $R^5R^5N—(C=O)—$, and $R^5—(=O)—$; wherein $R^a$ is optionally substituted;

wherein $R^2$ is selected from H, alkyl, haloalkyl, aryl, heterocyclyl, arylalkyl, heterocyclylalkyl, cycloalkyl, cycloalkylalkyl, alkenyl, alkynyl and $R^5$-carbonyl;

wherein $R^3$ and $R^4$ is each independently selected from H, alkyl, aryl, heterocyclyl, arylalkyl, heterocyclylalkyl, haloalkyl, cycloalkyl, cycloalkylalkyl, $R^6$ and alkyl substituted with $R^6$;

wherein $R^5$ is selected from H, alkyl, haloalkyl, hydroxyalkyl, alkoxyalkyl, alkylaminoalkyl, alkylthioalkyl, arylalkyl, heterocyclylalkyl, cycloalkylalkyl, aryl, heterocyclyl, alkenyl, alkynyl and cycloalkyl;

wherein $R^6$ is selected from cyano, $—OR^2$, $—SR^2$, halo, $—SO_2R^2$, $—C(=O)R^2$, $—SO_2NR^2R^5$, $—NR^5C(=O)OR^2$, $—NR^5C(=O)NR^5R^2$, $—NR^5C(=O)R^2$, $—CO_2R^2$, $—C(=O)NR^2R^5$ and $—NR^2R^5$;

wherein $R^x$ is selected from H, halo, $—NH_2$, $—OH$, $—CO_2H$, $(C_1-C_6)$alkylamino, $(C_1-C_6)$alkyl, $(C_1-C_6)$alkoxy, and $(C_1-C_6)$haloalkyl;

wherein p is 0, 1, 2, or 3; and
wherein t is 0, 1 or 2;

wherein each alkyl, aryl, heteroaryl, cycloalkyl, alkenyl, alkynyl, heterocyclyl, and alkoxy moiety of any R, $R^1$, $R^2$, $R^3$, $R^4$, $R^5$ and $R^a$ is optionally substituted with one or more groups selected from halo, $—NH_2$, $—OH$, $—CO_2H$, $(C_1-C_6)$alkylamino, $(C_1-C_6)$alkyl, $(C_1-C_6)$alkoxy, $(C_1-C_6)$haloalkyl, di$(C_1-C_6)$alkylamino, $(C_1-C_6)$alkylamino-$(C_1-C_6)$alkyl, $(C_1-C_6)$hydroxyalkylamino, $(C_1-C_6)$alkylamino-$(C_1-C_6)$alkylamino, phenyl, and heterocyclyl;

and pharmaceutically acceptable derivatives thereof.

The invention also relates to compounds of Formula I or I' wherein R is selected from H, 6-10 membered aryl, 4-10 membered heterocyclyl, 4-6 membered cycloalkyl, $C_{1-6}$-alkyl, $C_{2-6}$-alkenyl and $C_{2-6}$-alkynyl; wherein R is substituted or unsubstituted; in conjunction with any of the above or below embodiments.

The invention also relates to compounds of Formula I or I' wherein R is optionally substituted phenyl; in conjunction with any of the above or below embodiments.

The invention also relates to compounds of Formula I or I' wherein R is phenyl, 2-fluorophenyl, 3-fluorophenyl, 4-fluorophenyl, 4-methylphenyl, 4-trifluoromethylphenyl or 4-(dimethylamino)phenyl; in conjunction with any of the above or below embodiments.

The invention also relates to compounds of Formula I or I' wherein R is a substituted or unsubstituted heterocyclyl ring selected from pyrrolidinyl, piperidinyl, piperazinyl, 2,3-dihydroindolyl, pyrrolyl, imidazolyl, pyrazolyl, pyrazinyl, pyrimidinyl, pyridyl, quinolinyl, isoquinolinyl, 2,3-dihydrobenzofuryl, 2,3-dihydro-1,4-benzodioxinyl, 1,3-benzodioxolyl, isoxazolyl, isothiazolyl, oxazolyl, thiazolyl, furanyl, and thienyl; in conjunction with any of the above or below embodiments.

The invention also relates to compounds of Formula I or I' wherein R is 3-6 membered cycloalkyl selected from cyclopropyl, cyclobutyl, cyclopentyl and cyclohexyl; in conjunction with any of the above or below embodiments.

The invention also relates to compounds of Formula I or I' wherein R is selected from methyl, ethyl, propyl, butyl, isobutyl, tert-butyl, 3,3-dimethylpropyl and pentyl; in conjunction with any of the above or below embodiments.

The invention also relates to compounds of Formula I or I' wherein R is selected from ethenyl and propenyl; in conjunction with any of the above or below embodiments.

The invention also relates to compounds of Formula I or I' wherein R is H; in conjunction with any of the above or below embodiments.

The invention also relates to compounds of Formula I or I' wherein A is selected from

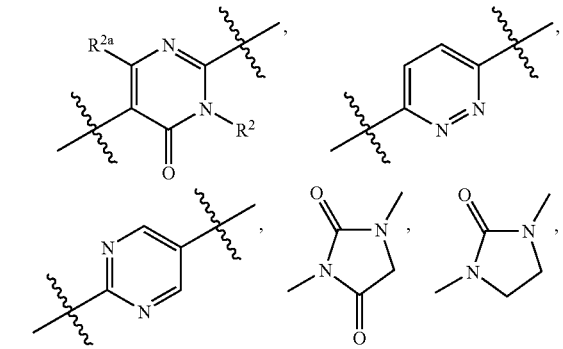

-continued

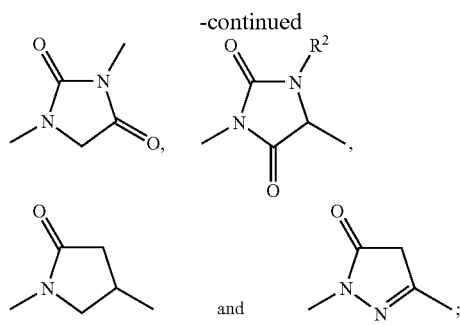

and

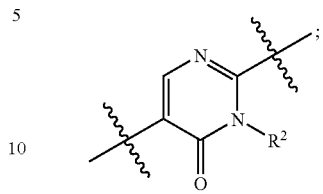

in conjunction with any of the above or below embodiments.

The invention also relates to compounds of Formula I or I' wherein A is wherein A is bound in either direction; wherein $R^2$ is selected from H, $C_{1-3}$-alkyl, aryl-$C_{1-3}$-alkyl, and heterocyclyl-$C_{1-3}$-alkyl; and wherein $R^{2a}$ is selected from H and methyl; in conjunction with any of the above or below embodiments.

The invention also relates to compounds of Formula I or I' wherein A is selected from

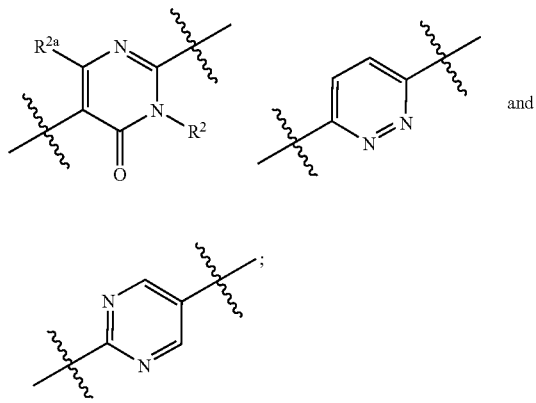

and

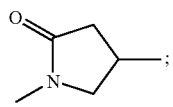

in conjunction with any of the above or below embodiments.

The invention also relates to compounds of Formula I or I' wherein A is

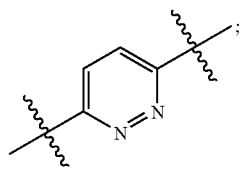

in conjunction with any of the above or below embodiments.

The invention also relates to compounds of Formula I or I' wherein A is selected from

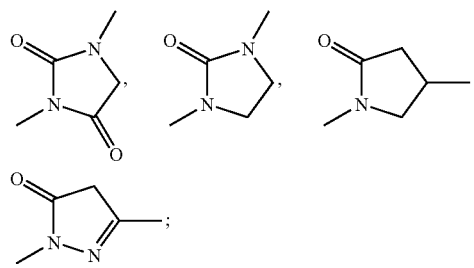

in conjunction with any of the above or below embodiments.

The invention also relates to compounds of Formula I or I' wherein A is

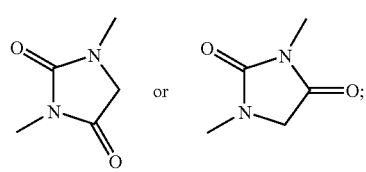

in conjunction with any of the above or below embodiments.

The invention also relates to compounds of Formula I or I' wherein A is

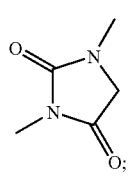

in conjunction with any of the above or below embodiments.

The invention also relates to compounds of Formula I or I' wherein A is

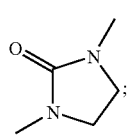

in conjunction with any of the above or below embodiments.

The invention also relates to compounds of Formula I or I' wherein A is

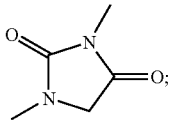

in conjunction with any of the above or below embodiments.

The invention also relates to compounds of Formula I or I' wherein A is

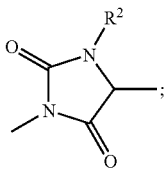

in conjunction with any of the above or below embodiments.

The invention also relates to compounds of Formula I or I' wherein A is

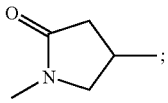

in conjunction with any of the above or below embodiments.

The invention also relates to compounds of Formula I or I' wherein A is

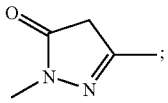

in conjunction with any of the above or below embodiments.

The invention also relates to compounds of Formula I or I' wherein $R^1$ is selected from 9-10-membered bicyclic nitrogen-containing heterocyclyl; in conjunction with any of the above or below embodiments.

The invention also relates to compounds of Formula I or I' wherein $R^1$ is selected from

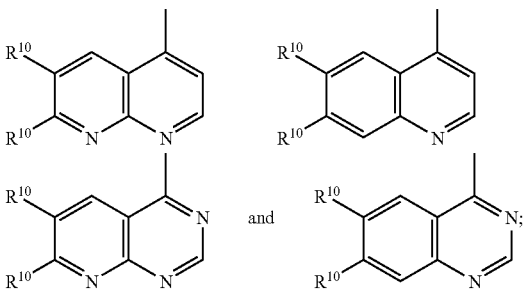

and wherein $R^{10}$ is selected from $C_{1-3}$-alkoxy, $C_{1-3}$-alkylamino-$C_{1-3}$-alkoxy, 5-6 membered heterocyclyl-$C_{1-3}$-alkoxy, $C_{4-6}$-cycloalkyl-$C_{1-3}$-alkoxy, 5-6 membered heterocyclyl-$C_{1-3}$-(hydroxyalkoxy), $C_{3-6}$-cycloalkyl-$C_{1-3}$-(hydroxyalkoxy), $C_{1-2}$-alkoxy-$C_{1-3}$-alkoxy, phenyloxy-$C_{1-3}$ alkoxy, 5-6 membered heterocyclyloxy-$C_{1-3}$-alkoxy, cycloalkyloxy-$C_{1-3}$-alkoxy, 5-6 membered heterocyclyloxy, and $C_{3-6}$-cycloalkyloxy; in conjunction with any of the above or below embodiments.

The invention also relates to compounds of Formula I or I' wherein $R^1$ is selected from 6,7-dimethoxy-4-quinolinyl, 6-methoxy-7-(dimethylaminopropoxy)-4-quinolinyl, 6-methoxy-7-(3-(morpholin-4-yl)propoxy)-4-quinolinyl, 6-methoxy-7-(3-(pyrrolidin-1-yl)propoxy)-4-quinolinyl, 6-methoxy-7-(2-hydroxy-3-(morpholin-4-yl)propoxy)-4-quinolinyl, 6-methoxy-7-(3-(1,2,4-triazol-1-yl)propoxy)-4-quinolinyl, 6-methoxy-7-(3-(4-methylpiperazin-1-yl)propoxy)-4-quinolinyl, 6-methoxy-7-(3-(piperidin-4-yl)propoxy)-4-quinolinyl, 6,7-dimethoxy-4-quinazolinyl, and 6-methoxy-7-(dimethylaminopropoxy)-4-quinazolinyl; in conjunction with any of the above or below embodiments.

The invention also relates to compounds of Formula I or I' wherein $R^1$ is selected from 6-methoxy-7-(3-(morpholin-4-yl)propoxy)-4-quinolinyl; in conjunction with any of the above or below embodiments.

The invention also relates to compounds of Formula I or I' wherein $R^1$ is 6,7-dimethoxy-4-quinolinyl; in conjunction with any of the above or below embodiments.

The invention also relates to compounds of Formula I or I' wherein Y is selected from direct bond, $-NR^b(CR^3R^4)_p-$, $-O(CR^3R^4)_p-$, $-(CR^3R^4)_p-$ and $-C(=O)(CR^3R^4)_p-$; and wherein p is 0 or 1; in conjunction with any of the above or below embodiments.

The invention also relates to compounds of Formula I or I' wherein Y is selected from a direct bond, $-NH-$, $-NHCH_2-$ and $-CH_2-$; in conjunction with any of the above or below embodiments.

The invention also relates to compounds of Formula I or I' wherein Y is $-CH_2-$; in conjunction with any of the above or below embodiments.

The invention also relates to compounds of Formula I or I' wherein Y is a direct bond; in conjunction with any of the above or below embodiments.

The invention also relates to compounds of Formula I or I' wherein Y is $-NH-$; in conjunction with any of the above or below embodiments.

The invention also relates to compounds of Formula I or I' wherein Y is $-N(CH_3)-$; in conjunction with any of the above or below embodiments.

The invention also relates to compounds of Formula I or I' wherein Y is $-CH(CH_3)-$; in conjunction with any of the above or below embodiments.

The invention also relates to compounds of Formula I or I' wherein R is selected from H, ethyl, isopropyl, $(CH_3)_3CCH_2-$, ethenyl, and an unsubstituted or substituted ring selected from phenyl, cyclobutyl, cyclopentyl, cyclohexyl, 2-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; in conjunction with any of the above or below embodiments.

The invention also relates to compounds of Formula I or I' wherein $R^x$ is selected from H, halo, $-NH_2$, $-OH$, $-CO_2H$, C₁-C₃-alkylamino, C₁-C₃-alkyl, C₁-C₃-alkoxy and C₁-C₂haloalkyl; in conjunction with any of the above or below embodiments.

The invention also relates to compounds of Formula I or I' wherein $R^a$ is selected from H, $C_{1-3}$-alkyl, 5-6-membered heterocyclyl, phenyl, phenyl-$C_{1-3}$-alkyl, 5-6-membered heterocyclyl-$C_{1-3}$-alkyl, $C_{3-6}$-cycloalkyl, $C_{3-6}$-cycloalkyl-$C_{1-3}$-alkyl, $R^5R^5N$—(C=O)— and $R^5$—(=O)—; in conjunction with any of the above or below embodiments.

The invention also relates to compounds of Formula I or I' wherein $R^2$ is selected from H, $C_{1-3}$-alkyl, $C_{1-2}$-haloalkyl, phenyl, 5-6-membered heterocyclyl, phenyl-$C_{1-3}$-alkyl, 5-6-membered heterocyclyl-$C_{1-3}$-alkyl, $C_{3-6}$-cycloalkyl, and $C_{3-6}$-cycloalkyl-$C_{1-3}$-alkyl; in conjunction with any of the above or below embodiments.

The invention also relates to compounds of Formula I or I' wherein $R^3$ is selected from H, $C_{1-3}$-alkyl, phenyl, 5-6-membered heterocyclyl, phenyl-$C_{1-3}$-alkyl, 5-6-membered heterocyclyl-$C_{1-3}$-alkyl, $C_{1-2}$-haloalkyl, $C_{3-6}$-cycloalkyl, $C_{3-6}$-cycloalkyl-$C_{1-3}$-alkyl, $R^6$ and $C_{1-3}$-alkyl substituted with $R^6$; in conjunction with any of the above or below embodiments.

The invention also relates to compounds of Formula I or I' wherein $R^4$ is selected from H, $C_{1-3}$-alkyl, phenyl, 5-6-membered heterocyclyl, phenyl-$C_{1-3}$-alkyl, 5-6-membered heterocyclyl-$C_{1-3}$-alkyl, $C_{1-2}$-haloalkyl, $C_{3-6}$-cycloalkyl, $C_{3-6}$-cycloalkyl-$C_{1-3}$-alkyl, $R^6$ and $C_{1-3}$-alkyl substituted with $R^6$; in conjunction with any of the above or below embodiments.

The invention also relates to compounds of Formula I or I' wherein $R^5$ is selected from H, $C_{1-3}$-alkyl, $C_{1-2}$-haloalkyl, phenyl-$C_{1-3}$-alkyl, 5-6-membered heterocyclyl-$C_{1-3}$-alkyl, $C_{3-6}$-cycloalkyl-$C_{1-3}$-alkyl, phenyl, 5-6-membered heterocyclyl, and $C_{3-6}$-cycloalkyl; in conjunction with any of the above or below embodiments.

The invention also relates to compounds of Formula I or I' wherein $R^6$ is selected from —$OR^2$, halo, —$SO_2R^2$, —C(=O)$R^2$, —$SO_2NR^2R^5$, —$NR^5C$(=O)$R^2$, —$CO_2R^2$, —C(=O)$NR^2R^5$ and —$NR^2R^5$; in conjunction with any of the above or below embodiments.

The invention also relates to compounds of Formula I or I' wherein X is O; in conjunction with any of the above or below embodiments.

The invention relates to compounds of Formula I wherein W is phenyl; in conjunction with any of the above or below embodiments.

The invention also relates to compounds of Formula I wherein W is fluorophenyl; in conjunction with any of the above or below embodiments.

The invention also relates to compounds of Formula I and pharmaceutically acceptable salts thereof selected from 2-Benzyl-5-{3-fluoro-4-[6-methoxy-7-(3-morpholin-4-yl-propoxy)-quinolin-4-yloxy]-phenyl}-3-methyl-3H-pyrimidin-4-one;

5-(4-((6,7-bis(methoxy)-4-quinolinyl)oxy)-3-fluorophenyl)-6-methyl-2-(phenylmethyl)-4(3H)-pyrimidinone;

5-(4-((6,7-bis(methoxy)-4-quinolinyl)oxy)-3-fluorophenyl)-2-(phenylmethyl)-4(3H)-pyrimidinone;

5-(3-fluoro-4-((6-methoxy-7-(3-(4-morpholinyl)propoxy)-4-quinolinyl)oxy)phenyl)-2-(phenylmethyl)-4(3H)-pyrimidinone;

5-(3-fluoro-4-((7-(((2R)-2-hydroxy-3-(4-morpholinyl)-propyl)oxy)-6-methoxy-4-quinolinyl)oxy)phenyl)-3-methyl-2-(phenylmethyl)-4(3H)-pyrimidinone;

5-(3-fluoro-4-((6-methoxy-7-((3-(1-pyrrolidinyl)propyl)oxy)-4-quinolinyl)oxy)phenyl)-3-methyl-2-(phenylmethyl)-4(3H)-pyrimidinone;

5-[4-(6,7-Dimethoxy-quinolin-4-yloxy)-3-fluoro-phenyl]-2-(4-fluoro-phenylamino)-3-methyl-3H-pyrimidin-4-one;

5-[4-(6,7-Dimethoxy-quinolin-4-yloxy)-3-fluorophenyl]-2-(3-fluoro-phenylamino)-3-methyl-3H-pyrimidin-4-one;

5-(4-((6,7-bis(methoxy)-4-quinolinyl)oxy)-3-fluorophenyl)-3-methyl-2-methylthio-4(3H)-pyrimidinone;

5-(4-((6,7-bis(methoxy)-4-quinolinyl)oxy)-3-fluorophenyl)-3-methyl-2-(phenylamino)-4(3H)-pyrimidinone;

5-(4-((6,7-bis(methoxy)-4-quinolinyl)oxy)-3-fluorophenyl)-2-((2-fluorophenyl)amino)-3-methyl-4(3H)-pyrimidinone;

5-(3-fluoro-4-((6-methoxy-7-(3-(1H-1,2,4-triazol-1-yl)propoxy)-4-quinolinyl)oxy)phenyl)-3-methyl-2-(phenylmethyl)-4(3H)-pyrimidinone;

5-(4-((6,7-bis(methoxy)-4-quinolinyl)oxy)-3-fluorophenyl)-2-cyclopentyl-3-methyl-4(3H)-pyrimidinone;

5-(3-fluoro-4-((6-methoxy-7-(3-(4-morpholinyl)propoxy)-4-quinolinyl)oxy)phenyl)-2-((4-fluorophenyl)amino)-3-methyl-4(3H)-pyrimidinone;

5-(4-((6,7-bis(methoxy)-4-quinolinyl)oxy)-3-fluorophenyl)-3-methyl-2-((4-methylphenyl)amino)-4(3H)-pyrimidinone;

5-(4-((6,7-bis(methoxy)-4-quinolinyl)oxy)-3-fluorophenyl)-3-methyl-2-((4-(trifluoromethyl)phenyl)amino)-4(3H)-pyrimidinone;

2-((4-(dimethylamino)phenyl)amino)-5-(3-fluoro-4-((6-methoxy-7-((3-(4-morpholinyl)propyl)oxy)-4-quinolinyl)oxy)phenyl)-3-methyl-4(3H)-pyrimidinone;

2-((2,2-dimethylpropyl)amino)-5-(3-fluoro-4-((6-methoxy-7-(3-(4-morpholinyl)propoxy)-4-quinolinyl)oxy)phenyl)-3-methyl-4(3H)-pyrimidinone;

5-(3-fluoro-4-((6-methoxy-7-((3-(4-morpholinyl)propyl)oxy)-4-quinolinyl)oxy)phenyl)-3-methyl-2-(phenylamino)-4(3H)-pyrimidinone;

5-(4-((6,7-bis(methoxy)-4-quinolinyl)oxy)-3-fluorophenyl)-3-methyl-2-((2-methylpropyl)amino)-4(3H)-pyrimidinone;

5-(4-(6,7-bis(methoxy)-4-quinolinyloxy)-3-fluorophenyl)-3-methyl-2-(methyl(phenyl)amino)-4(3H)-pyrimidinone;

5-(4-(6,7-bis(methoxy)-4-quinolinyloxy)-3-fluorophenyl)-3-methyl-2-((1-phenylethyl)amino)-4(3H)-pyrimidinone;

5-(4-(6,7-bis(methoxy)-4-quinolinyloxy)-3-fluorophenyl)-3-methyl-2-phenyl-4(3H)-pyrimidinone;

5-(4-((6,7-bis(methoxy)-4-quinolinyl)oxy)-3-fluorophenyl)-3-methyl-2-(1-pyrrolidinyl)-4(3H)-pyrimidinone;

5-(3-fluoro-4-((6-methoxy-7-(3-(4-methyl-1-piperazinyl)propoxy)-4-quinolinyl)oxy)phenyl)-3-methyl-2-(phenylmethyl)-4(3H)-pyrimidinone;

5-(4-((6,7-bis(methoxy)-4-quinolinyl)oxy)-3-fluorophenyl)-3-methyl-2-((3-methylbutyl)(phenyl)amino)-4(3H)-pyrimidinone;

5-(3-fluoro-4-(6-methoxy-7-((3-(4-morpholinyl)propoxy)-4-quinolinyl)oxy)phenyl)-2-((4-fluorophenyl)methyl)-3-methyl-4(3H)-pyrimidinone;

5-(3-fluoro-4-((6-methoxy-7-((phenylmethoxy)-4-quinolinyl)oxy)phenyl)-3-methyl-2-(phenylmethyl)-4(3H)-pyrimidinone;

5-(4-((6,7-bis(methoxy)-4-quinolinyl)oxy)-3-fluorophenyl)-2-((cyclopropylmethyl)amino)-3-methyl-4(3H)-pyrimidinone;

5-(4-((6,7-bis(methoxy)-4-quinolinyl)oxy)-3-fluorophenyl)-3-methyl-2-((phenylmethyl)amino)-4(3H)-pyrimidinone;

5-(4-((7-(3-(4-ethyl-1-piperazinyl)propoxy)-6-methoxy-4-quinolinyl)oxy)-3-fluorophenyl)-3-methyl-2-(phenylmethyl)-4(3H)-pyrimidinone;

5-(3-fluoro-4-((6-methoxy-7-(3-(4-morpholinyl)propoxy)-4-quinolinyl)oxy)phenyl)-3-methyl-2-((4-methylphenyl)methyl)-4(3H)-pyrimidinone;

5-(3-fluoro-4-((7-((3-(4-hydroxy-1-piperidinyl)propyl)oxy)-6-methoxy-4-quinolinyl)oxy)phenyl)-3-methyl-2-(phenylmethyl)-4(3H)-pyrimidinone;

1-Benzyl-4-{3-fluoro-4-[6-methoxy-7-(3-morpholin-4-yl-propoxy)-quinolin-4-yloxy]-phenyl}-piperazine-2,5-dione;

5-[4-(6,7-Dimethoxy-quinolin-4-yloxy)-3-fluoro-phenyl]-3-methyl-2-(pyridin-2-ylamino)-3H-pyrimidin-4-one;

2-(Amino-phenyl-methyl)-5-[4-(6,7-dimethoxy-quinolin-4-yloxy)-3-fluoro-phenyl]-3-methyl-3H-pyrimidin-4-one;

5-[4-(6,7-Dimethoxy-quinolin-4-yloxy)-3-fluoro-phenyl]-3-methyl-2-[1-(2,2,2-trifluoro-acetyl)-piperidin-3-ylamino]-3H-pyrimidin-4-one;

5-[4-(6,7-Dimethoxy-quinolin-4-yloxy)-3-fluoro-phenyl]-3-methyl-2-(1-propyl-piperidin-3-ylamino)-3H-pyrimidin-4-one;

2-(1-Acetyl-piperidin-3-ylamino)-5-[4-(6,7-dimethoxy-quinolin-4-yloxy)-3-fluoro-phenyl]-3-methyl-3H-pyrimidin-4-one;

3-(4-((6,7-bis(methoxy)-4-quinolinyl)oxy)-3-fluorophenyl)-1-methyl-6-(3-pyridinylamino)-2(1H)-pyridinone;

5-(4-((6,7-bis(methoxy)-4-quinolinyl)oxy)-3-fluorophenyl)-2-(cyclohexylamino)-3-methyl-4(3H)-pyrimidinone;

5-(3-fluoro-4-((6-methoxy-7-((3-(4-morpholinyl)-propyl)oxy)-4-quinolinyl)oxy)phenyl)-2-(hydroxy(phenyl)methyl)-3-methyl-4(3H)-pyrimidinone;

5-(4-((6,7-bis(methoxy)-4-quinolinyl)oxy)-3-fluorophenyl)-2-((4-fluoro-2-methylphenyl)amino)-4(3H)-pyrimidinone;

5-(4-((6,7-bis(methoxy)-4-quinolinyl)oxy)-3-fluorophenyl)-2-((4-fluoro-2-methylphenyl)amino)-3-methyl-4(3H)-pyrimidinone;

5-(4-((6,7-bis(methoxy)-4-quinolinyl)oxy)-3-fluorophenyl)-3-methyl-2-((2-phenylethyl)amino)-4(3H)-pyrimidinone;

5-(4-((6,7-bis(methoxy)-4-quinolinyl)oxy)-3-fluorophenyl)-2-4-fluorophenyl)-3-methyl-4(3H)-pyrimidinone;

5-(3-fluoro-4-((6-(methoxy)-7-((3-(4-morpholinyl)propyl)oxy)-4-quinolinyl)oxy)phenyl)-2-(phenylamino)-4(3H)-pyrimidinone;

5-(4-((6,7-bis(methoxy)-4-quinolinyl)oxy)-3-fluorophenyl)-3-methyl-2-((1R)-1-phenylethyl)-4(3H)-pyrimidinone;

5-(4-((6,7-bis(methoxy)-4-quinolinyl)oxy)-3-fluorophenyl)-2-(phenylamino)-4(3H)-pyrimidinone;

5-(3-fluoro-4-((6-methoxy-7-((3-(4-morpholinyl)propyl)oxy)-4-quinolinyl)oxy)phenyl)-3-methyl-2-((4-methoxyphenyl)amino)-4(3H)-pyrimidinone;

2-((4-chlorophenyl)amino)-5-(3-fluoro-4-((6-methoxy-7-((3-(4-morpholinyl)propyl)oxy)-4-quinolinyl)oxy)phenyl)-3-methyl-4(3H)-pyrimidinone;

5-(3-fluoro-4-((7-hydroxy-6-methoxy-4-quinolinyl)oxy)phenyl)-3-methyl-2-(phenylmethyl)-4(3H)-pyrimidinone;

5-(3-fluoro-4-((6-methoxy-7-((3-(4-morpholinyl)propyl)oxy)-4-quinolinyl)oxy)phenyl)-3-methyl-2-(phenylcarbonyl)-4(3H)-pyrimidinone;

5-(4-((6,7-bis(methoxy)-4-quinolinyl)oxy)-3-fluorophenyl)-3-methyl-2-(phenylmethyl)-4(3H)-pyrimidinone;

{2-[4-(6,7-Dimethoxy-quinolin-4-yloxy)-3-fluoro-phenyl]-pyrimidin-5-yl}-phenylamine;

2-(4-(6,7-dimethoxynaphthalen-1-yloxy)-3-fluorophenyl)-N-isopentyl-N-phenylpyrimidin-5-amine;

{6-[4-(6,7-Dimethoxy-quinolin-4-yloxy)-phenyl]-pyridazin-3-yl}-phenyl-amine;

4-[4-(6-Benzyl-pyridazin-3-yl)-2-fluoro-phenoxy]-6,7-dimethoxy-quinoline;

4-[2-Fluoro-4-(6-phenoxy-pyridazin-3-yl)-phenoxy]-6,7-dimethoxy-quinoline;

6-(4-((6,7-bis(methoxy)-4-quinolinyl)oxy)-3-fluorophenyl)-N-(3-chlorophenyl)-3-pyridazinamine;

6-(4-((6,7-bis(methoxy)-4-quinolinyl)oxy)-3-fluorophenyl)-N-methyl-N-phenyl-3-pyridazinamine;

6-(4-((6,7-bis(methoxy)-4-quinolinyl)oxy)-3-fluorophenyl)-N-(2-chlorophenyl)-3-pyridazinamine;

6-(4-((6,7-bis(methoxy)-4-quinolinyl)oxy)-3-chlorophenyl)-N-phenyl-3-pyridazinamine;

4-((4-(6-(2,3-dihydro-1H-indol-1-yl)-3-pyridazinyl)-2-fluorophenyl)oxy)-6,7-bis(methoxy)quinolines;

6-(4-((6,7-bis(methoxy)-4-quinolinyl)oxy)-3-fluorophenyl)-N-(3-fluorophenyl)-3-pyridazinamine;

6-(4-((6,7-bis(methoxy)-4-quinolinyl)oxy)-3-fluorophenyl)-N-(2-methoxyphenyl)-3-pyridazinamine;

6-(3-fluoro-4-((6-methoxy-7-((3-(4-morpholinyl)propyl)oxy)-4-quinolinyl)oxy)phenyl)-N-phenyl-3-pyridazinamine;

6-(4-((6,7-bis(methoxy)-4-quinolinyl)oxy)-3-fluorophenyl)-N-phenyl-3-pyridazinamine;

6-(4-((6,7-bis(methoxy)-4-quinolinyl)oxy)-3-fluorophenyl)-N-(2,2,2-trifluoroethyl)-3-pyridazinamine;

6-(4-((6,7-bis(methoxy)-4-quinolinyl)oxy)-3-fluorophenyl)-N-cyclopentyl-3-pyridazinamine;

6-(4-((6,7-bis(methoxy)-4-quinolinyl)oxy)-3-fluorophenyl)-N-(2,3-dimethylphenyl)-3-pyridazinamine;

6-(4-((6,7-bis(methoxy)-4-quinolinyl)oxy)-3-fluorophenyl)-N-(2-methylphenyl)-3-pyridazinamine;

1-(4-(6,7-Dimethoxyquinolin-4-yloxy)-3-fluorophenyl)-4-(phenoxymethyl)pyrrolidin-2-one;

N-(1-(4-(6,7-Dimethoxyquinolin-4-yloxy)-3-fluorophenyl)-5-oxopyrrolidin-3-yl)benzamide;

4-Benzoyl-1-(4-(6,7-dimethoxyquinolin-4-yloxy)-3 fluorophenyl)pyrrolidin-2-one;

1-(4-(6,7-Dimethoxyquinolin-4-yloxy)-3-fluorophenyl)-4-(methoxy(phenyl)methyl)pyrrolidin-2-one;

1-Benzyl-3-(4-(7-(benzyloxy)-6-methoxyquinolin-4-yloxy)-3-fluorophenyl)imidazolidine-2,4-dione;

1-Benzyl-3-(3-fluoro-4-(6-methoxy-7-(3-morpholino-propoxy)quinolin-4-yloxy)phenyl)imidazolidine-2,4-dione;

1-(3-Fluoro-4-((6-methoxy-7-(3-(4-morpholinyl)propoxy)-4-quinolinyl)oxy)phenyl)-2-imidazolidinone;

1-(4-((6,7-bis(methoxy)-4-quinolinyl)oxy)-3-fluorophenyl)-4-((ethoxy)(phenyl)methyl)-2-pyrrolidinone;

1-(4-((6,7-bis(methoxy)-4-quinolinyl)oxy)-3-fluorophenyl)-4-(phenyl(propoxy)methyl)-2-pyrrolidinone;

3-(4-((6,7-bis(methoxy)-4-quinolinyl)oxy)-3-fluorophenyl)-1-(phenylmethyl)-2,4-imidazolidinedione;

1-{3-Fluoro-4-[6-methoxy-7-(3-morpholin-4-yl-propoxy)-quinolin-4-yloxy]-phenyl}-4-(methoxy-phenyl-methyl)-pyrrolidin-2-one;

3-{3-Fluoro-4-[6-methoxy-7-(3-morpholin-4-yl-propoxy)-quinolin-4-yloxy]-phenyl}-5-methyl-imidazolidine-2,4-dione;

5-Benzyl-3-{3-fluoro-4-[6-methoxy-7-(3-morpholin-4-yl-propoxy)-quinolin-4-yloxy]-phenyl}-imidazolidine-2,4-dione;

1-[4-(6,7-Dimethoxy-quinolin-4-yloxy)-3-fluoro-phenyl]-4-(phenyl-propoxy-methyl)-pyrrolidin-2-one;

1-[4-(6,7-Dimethoxy-quinolin-4-yloxy)-3-fluoro-phenyl]-4-(phenyl-propoxy-methyl)-pyrrolidin-2-one;

3-[4-(7-Benzyloxy-6-methoxy-quinolin-4-yloxy)-3-fluoro-phenyl]-1-phenyl-imidazolidine-2,4-dione;

3-{3-Fluoro-4-[6-methoxy-7-(3-morpholin-4-yl-propoxy)-quinolin-4-yloxy]-phenyl}-1-isobutyl-imidazolidine-2,4-dione;

5-Benzyl-3-{3-fluoro-4-[6-methoxy-7-(3-morpholin-4-yl-propoxy)-quinolin-4-yloxy]-phenyl}-1-methyl-imidazolidine-2,4-dione;

3-{3-Fluoro-4-[6-methoxy-7-(3-morpholin-4-yl-propoxy)-quinolin-4-yloxy]-phenyl}-1-phenethyl-imidazolidine-2,4-dione;

1-[4-(6,7-Dimethoxy-quinolin-4-yloxy)-3-fluoro-phenyl]-4-(phenyl-propoxy-methyl)-pyrrolidin-2-one;

1-[4-(6,7-Dimethoxy-quinolin-4-yloxy)-3-fluoro-phenyl]-4-(phenyl-propoxy-methyl)-pyrrolidin-2-one;

4-Benzyl-1-{3-fluoro-4-[6-methoxy-7-(3-morpholin-4-yl-propoxy)-quinolin-4-yloxy]-phenyl}-pyrrolidin-2-one;

4-Benzyl-1-[4-(6,7-dimethoxy-quinolin-4-yloxy)-3-fluoro-phenyl]-pyrrolidin-2-one;

3-Benzyl-1-{3-fluoro-4-[6-methoxy-7-(3-morpholin-4-yl-propoxy)-quinolin-4-yloxy]-phenyl}-imidazolidine-2,4-dione; and 1-[4-(6,7-Dimethoxy-quinolin-4-yloxy)-3-fluoro-phenyl]-4-phenoxymethyl-pyrrolidin-2-one.

The invention also relates to compounds of Formula II

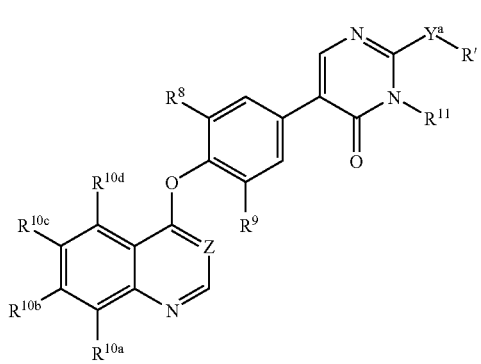

II wherein $Y^a$ is selected from a direct bond, —$NR^b(CH_2)_p$— and —$CH_2$—;
wherein p is 0, 1, 2, or 3; wherein $R^b$ is H or $C_{1-3}$-alkyl,
wherein Z is CH or N;
wherein R' is selected from H, $C_{1-6}$-alkyl, di-$C_{1-3}$-alkylamino and an unsubstituted or substituted ring selected from phenyl, $C_{3-6}$-cycloalkyl, pyrrolidinyl, piperidinyl, piperazinyl, 2,3-dihydroindolyl, pyrrolyl, imidazolyl, pyrazolyl, pyrazinyl, pyrimidinyl, pyridyl, quinolinyl, isoquinolinyl, 2,3-dihydrobenzofuryl, 2,3-dihydro-1,4-benzodioxinyl, 1,3-benzodioxolyl, isoxazolyl, isothiazolyl, oxazolyl, thiazolyl, furanyl, and thienyl;
wherein $R^8$ is selected from H, fluoro, chloro and methyl;
wherein $R^9$ is selected from H, methyl and fluoro;
wherein $R^{10a}$, $R^{10b}$, $R^{10c}$ and $R^{10d}$ is each independently selected from $C_{1-3}$-alkoxy, $C_{1-3}$-alkylamino-$C_{1-3}$-alkoxy, 5-6 membered heterocyclyl-$C_{1-3}$-alkoxy, $C_{4-6}$-cycloalkyl-$C_{1-3}$-alkoxy, 5-6 membered heterocyclyl-$C_{1-3}$-(hydroxyalkoxy), $C_{3-6}$-cycloalkyl-$C_{1-3}$-(hydroxyalkoxy), $C_{1-2}$-alkoxy-$C_{1-3}$-alkoxy, phenyloxy-$C_{1-3}$alkoxy, 5-6 membered heterocyclyloxy-$C_{1-4}$-alkoxy, cycloalkyloxy-$C_{1-3}$-alkoxy, 5-6 membered heterocyclyloxy, and $C_{3-6}$-cycloalkyloxy; and
wherein $R^{11}$ is H or methyl;

and pharmaceutically acceptable derivatives thereof.

The invention also relates to compounds of Formula II wherein Z is CH; in conjunction with any of the above or below embodiments.

The invention also relates to compounds of Formula II wherein $Y^a$ is selected from a direct bond, —$N(CH_3)$—, —$N(CH_2CH_2CH(CH_3)_2)$—, —$NHCH_2$—, —$NH(CH_2)_2$—, —$NHCH_2(CH_3)$—, —NH— and —$CH_2$—; in conjunction with any of the above or below embodiments.

The invention also relates to compounds of Formula II wherein $R^{11}$ is methyl; in conjunction with any of the above or below embodiments.

The invention also relates to compounds of Formula II wherein R' is selected from ethyl, isopropyl, isobutyl, $(CH_3)_3CCH_2$—, and dimethylamino; in conjunction with any of the above or below embodiments.

The invention also relates to compounds of Formula II wherein R' is selected from cyclopropyl, cyclobutyl, cyclopentyl and cyclohexyl; in conjunction with any of the above or below embodiments.

The invention also relates to compounds of Formula II wherein R' is cyclopropyl or cyclopentyl; in conjunction with any of the above or below embodiments.

The invention also relates to compounds of Formula II wherein R' is selected from 1-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; in conjunction with any of the above or below embodiments.

The invention also relates to compounds of Formula II wherein R' is selected from phenyl, 2-fluorophenyl, 3-fluorophenyl, 4-fluorophenyl, 4-methylphenyl, 4-trifluoromethylphenyl, and 4-(dimethylamino)phenyl; in conjunction with any of the above or below embodiments.

The invention also relates to compounds of Formula II wherein $R^8$ is H; in conjunction with any of the above or below embodiments.

The invention also relates to compounds of Formula II wherein $R^9$ is H, methyl or fluoro; in conjunction with any of the above or below embodiments.

The invention also relates to compounds of Formula II wherein $R^{10a}$ and $R^{10d}$ are both H; and wherein $R^{10b}$ and $R^{10c}$ are independently selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy; in conjunction with any of the above or below embodiments.

The invention also relates to compounds of Formula II wherein $R^{10c}$ is methoxy; in conjunction with any of the above or below embodiments.

The invention also relates to compounds of Formula II and pharmaceutically acceptable salts thereof selected from 2-Benzyl-5-{3-fluoro-4-[6-methoxy-7-(3-morpholin-4-yl-propoxy)-quinolin-4-yloxy]-phenyl}-3-methyl-3H-pyrimidin-4-one;

5-(3-fluoro-4-((6-methoxy-7-(3-(4-morpholinyl)propoxy)-4-quinolinyl)oxy)phenyl)-2-(phenylmethyl)-4(3H)-pyrimidinone;

5-(3-fluoro-4-((7-(((2R)-2-hydroxy-3-(4-morpholinyl)-propyl)oxy)-6-methoxy-4-quinolinyl)oxy)phenyl)-3-methyl-2-(phenylmethyl)-4(3H)-pyrimidinone;

5-(3-fluoro-4-((6-methoxy-7-((3-(1-pyrrolidinyl)propyl)oxy)-4-quinolinyl)oxy)phenyl)-3-methyl-2-(phenylmethyl)-4(3H)-pyrimidinone;

5-[4-(6,7-Dimethoxy-quinolin-4-yloxy)-3-fluoro-phenyl]-2-(4-fluoro-phenylamino)-3-methyl-3H-pyrimidin-4-one;

5-(4-((6,7-bis(methoxy)-4-quinolinyl)oxy)-3-fluorophenyl)-3-methyl-2-(phenylamino)-4(3H)-pyrimidinone;
5-(3-fluoro-4-((6-methoxy-7-(3-(1H-1,2,4-triazol-1-yl)propoxy)-4-quinolinyl)oxy)phenyl)-3-methyl-2-(phenylmethyl)-4(3H)-pyrimidinone;
5-(3-fluoro-4-((6-methoxy-7-(3-(4-morpholinyl)propoxy)-4-quinolinyl)oxy)phenyl)-2-((4-fluorophenyl)amino)-3-methyl-4(3H)-pyrimidinone;
2-((4-(dimethylamino)phenyl)amino)-5-(3-fluoro-4-((6-methoxy-7-((3-(4-morpholinyl)propyl)oxy)-4-quinolinyl)oxy)phenyl)-3-methyl-4(3H)-pyrimidinone;
2-((2,2-dimethylpropyl)amino)-5-(3-fluoro-4-((6-methoxy-7-(3-(4-morpholinyl)propoxy)-4-quinolinyl)oxy)phenyl)-3-methyl-4(3H)-pyrimidinone;
5-(3-fluoro-4-((6-methoxy-7-((3-(4-morpholinyl)propyl)oxy)-4-quinolinyl)oxy)phenyl)-3-methyl-2-(phenylamino)-4(3H)-pyrimidinone;
5-(3-fluoro-4-((6-methoxy-7-(3-(4-methyl-1-piperazinyl)propoxy)-4-quinolinyl)oxy)phenyl)-3-methyl-2-(phenylmethyl)-4(3H)-pyrimidinone;
5-(3-fluoro-4-(6-methoxy-7-((3-(4-morpholinyl)propoxy)-4-quinolinyl)oxy)phenyl)-2-((4-fluorophenyl)methyl)-3-methyl-4(3H)-pyrimidinone;
5-(4-((7-(3-(4-ethyl-1-piperazinyl)propoxy)-6-methoxy-4-quinolinyl)oxy)-3-fluorophenyl)-3-methyl-2-(phenylmethyl)-4(3H)-pyrimidinone;
5-(3-fluoro-4-((6-methoxy-7-(3-(4-morpholinyl)propoxy)-4-quinolinyl)oxy)phenyl)-3-methyl-2-((4-methylphenyl)methyl)-4(3H)-pyrimidinone;
5-(3-fluoro-4-((7-((3-(4-hydroxy-1-piperidinyl)propyl)oxy)-6-methoxy-4-quinolinyl)oxy)phenyl)-3-methyl-2-(phenylmethyl)-4(3H)-pyrimidinone;
5-(3-fluoro-4-((6-methoxy-7-((3-(4-morpholinyl)-propyl)oxy)-4-quinolinyl)oxy)phenyl)-2-(hydroxy(phenyl)methyl)-3-methyl-4(3H)-pyrimidinone;
5-(4-((6,7-bis(methoxy)-4-quinolinyl)oxy)-3-fluorophenyl)-2-((4-fluoro-2-methylphenyl)amino)-3-methyl-4(3H)-pyrimidinone;
5-(3-fluoro-4-((6-methoxy-7-((3-(4-morpholinyl)propyl)oxy)-4-quinolinyl)oxy)phenyl)-2-(phenylamino)-4(3H)-pyrimidinone;
5-(4-((6,7-bis(methoxy)-4-quinolinyl)oxy)-3-fluorophenyl)-2-(phenylamino)-4(3H)-pyrimidinone;
5-(3-fluoro-4-((6-methoxy-7-((3-(4-morpholinyl)propyl)oxy)-4-quinolinyl)oxy)phenyl)-3-methyl-2-((4-methoxyphenyl)amino)-4(3H)-pyrimidinone;
2-((4-chlorophenyl)amino)-5-(3-fluoro-4-((6-methoxy-7-((3-(4-morpholinyl)propyl)oxy)-4-quinolinyl)oxy)phenyl)-3-methyl-4(3H)-pyrimidinone; and
5-(4-((6,7-bis(methoxy)-4-quinolinyl)oxy)-3-fluorophenyl)-3-methyl-2-(phenylmethyl)-4(3H)-pyrimidinone.

The invention also relates to compounds of Formula IIIa or IIIb

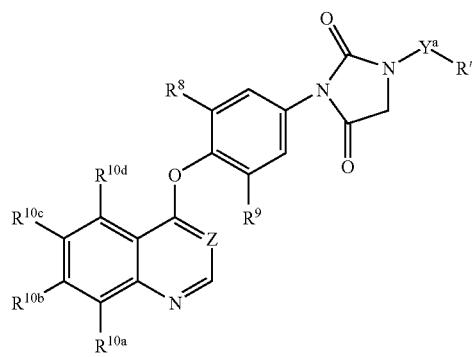

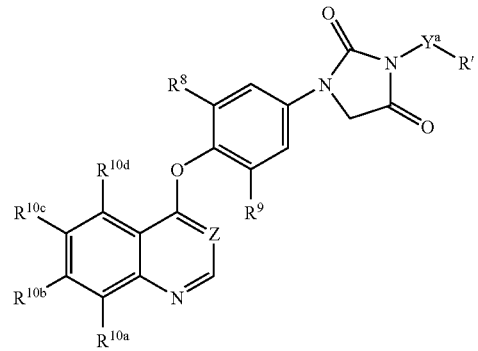

wherein $Y^a$ is selected from a direct bond, $-NR^b(CH_2)_p-$, $-CH_2CH_2-$ and $-CH_2-$; wherein p is 0, 1, 2, or 3; wherein $R^b$ is H or $C_{1-3}$-alkyl, wherein Z is CH or N;

wherein R' is selected from H, $C_{1-6}$-alkyl, di-$C_{1-3}$-alkylamino and an unsubstituted or substituted ring selected from phenyl, $C_{3-6}$-cycloalkyl, pyrrolidinyl, piperidinyl, piperazinyl, 2,3-dihydroindolyl, pyrrolyl, imidazolyl, pyrazolyl, pyrazinyl, pyrimidinyl, pyridyl, quinolinyl, isoquinolinyl, 2,3-dihydrobenzofuryl, 2,3-dihydro-1,4-benzodioxinyl, 1,3-benzodioxolyl, isoxazolyl, isothiazolyl, oxazolyl, thiazolyl, furanyl, and thienyl;

wherein $R^8$ is selected from H, fluoro, chloro and methyl;

wherein $R^9$ is selected from H, methyl and fluoro; and wherein $R^{10a}$, $R^{10b}$, $R^{10c}$ and $R^{10d}$ is each independently selected from $C_{1-3}$-alkoxy, $C_{1-3}$-alkylamino-$C_{1-3}$-alkoxy, 5-6 membered heterocyclyl-$C_{1-3}$-alkoxy, $C_{4-6}$-cycloalkyl-$C_{1-3}$-alkoxy, 5-6 membered heterocyclyl-$C_{1-3}$-(hydroxyalkoxy), $C_{3-6}$-cycloalkyl-$C_{1-3}$-(hydroxyalkoxy), $C_{1-2}$-alkoxy-$C_{1-3}$-alkoxy, phenyloxy-$C_{1-3}$alkoxy, 5-6 membered heterocyclyloxy-$C_{1-4}$-alkoxy, cycloalkyloxy-$C_{1-3}$-alkoxy, 5-6 membered heterocyclyloxy, and $C_{3-6}$-cycloalkyloxy;

and pharmaceutically acceptable derivatives thereof.

The invention also relates to compounds of Formula IIIa or IIIb wherein Z is CH; in conjunction with any of the above or below embodiments.

The invention also relates to compounds of Formula IIIa or IIIb wherein $Y^a$ is selected from a direct bond, $-N(CH_3)-$, $-N(CH_2CH_2CH(CH_3)_2)-$, $-NHCH_2-$, $-NH(CH_2)_2-$, $-NHCH_2(CH_3)-$, $-NH-$ and $-CH_2-$; in conjunction with any of the above or below embodiments.

The invention also relates to compounds of Formula IIIa or IIIb wherein R' is selected from ethyl, isopropyl, isobutyl, $(CH_3)_3CCH_2-$, and dimethylamino; in conjunction with any of the above or below embodiments.

The invention also relates to compounds of Formula IIIa or IIIb wherein R' is selected from cyclopropyl, cyclobutyl, cyclopentyl and cyclohexyl; in conjunction with any of the above or below embodiments.

The invention also relates to compounds of Formula IIIa or IIIb wherein R' is cyclopropyl or cyclopentyl; in conjunction with any of the above or below embodiments.

The invention also relates to compounds of Formula IIIa or IIIb wherein R' is selected from 1-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; in conjunction with any of the above or below embodiments.

The invention also relates to compounds of Formula IIIa or IIIb wherein R' is selected from phenyl, 2-fluorophenyl, 3-fluorophenyl, 4-fluorophenyl, 4-methylphenyl, 4-trifluoromethylphenyl, and 4-(dimethylamino)phenyl; in conjunction with any of the above or below embodiments.

The invention also relates to compounds of Formula IIIa or IIIb wherein $R^8$ is H; in conjunction with any of the above or below embodiments.

The invention also relates to compounds of Formula IIIa or IIIb wherein $R^9$ is H, methyl or fluoro; in conjunction with any of the above or below embodiments.

The invention also relates to compounds of Formula IIIa or IIIb wherein $R^{10a}$ and $R^{10d}$ are both H; and wherein $R^{10b}$ and $R^{10c}$ are independently selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy; in conjunction with any of the above or below embodiments.

The invention also relates to compounds of Formula IIIa or IIIb wherein $R^{10c}$ is methoxy; in conjunction with any of the above or below embodiments.

The invention also relates to compounds of Formula IIIa or IIIb and pharmaceutically acceptable salts thereof selected from
5-Benzyl-3-{3-fluoro-4-[6-methoxy-7-(3-morpholin-4-yl-propoxy)-quinolin-4-yloxy]-phenyl}-imidazolidine-2,4-dione;
5-Benzyl-3-{3-fluoro-4-[6-methoxy-7-(3-morpholin-4-yl-propoxy)-quinolin-4-yloxy]-phenyl}-1-methyl-imidazolidine-2,4-dione; and
3-{3-Fluoro-4-[6-methoxy-7-(3-morpholin-4-yl-propoxy)-quinolin-4-yloxy]-phenyl}-1-phenethyl-imidazolidine-2,4-dione.

The invention also relates to compounds of Formula IV

IV wherein $Y^a$ is selected from direct bond, —CO$_2$—, —C(=O)NH—NR$^b$(CH$_2$)$_p$—, —CH$_2$O—, $$\underset{\text{CH}}{\overset{OR^b}{\diagup\diagdown}}$$

and —CH$_2$—; wherein p is 0, 1, 2, or 3; wherein $R^b$ is H or C$_{1-3}$-alkyl;
wherein Z is CH or N;
wherein R' is selected from H, C$_{1-6}$-alkyl, di-C$_{1-3}$-alkylamino and an unsubstituted or substituted ring selected from phenyl, C$_{3-6}$-cycloalkyl, pyrrolidinyl, piperidinyl, piperazinyl, 2,3-dihydroindolyl, pyrrolyl, imidazolyl, pyrazolyl, pyrazinyl, pyrimidinyl, pyridyl, quinolinyl, isoquinolinyl, 2,3-dihydrobenzofuryl, 2,3-dihydro-1,4-benzodioxinyl, 1,3-benzodioxolyl, isoxazolyl, isothiazolyl, oxazolyl, thiazolyl, furanyl, and thienyl;
wherein $R^8$ is selected from H, fluoro, chloro and methyl;
wherein $R^9$ is selected from H, methyl and fluoro; and
wherein $R^{10a}$, $R^{10b}$, $R^{10c}$ and $R^{10d}$ is each independently selected from C$_{1-3}$-alkoxy, C$_{1-3}$-alkylamino-C$_{1-3}$-alkoxy, 5-6 membered heterocyclyl-C$_{1-3}$-alkoxy, C$_{4-6}$-cycloalkyl-C$_{1-3}$-alkoxy, 5-6 membered heterocyclyl-C$_{1-3}$-(hydroxyalkoxy), C$_{3-6}$-cycloalkyl-C$_{1-3}$-(hydroxyalkoxy), C$_{1-2}$-alkoxy-C$_{1-3}$-alkoxy, phenyloxy-C$_{1-3}$alkoxy, 5-6 membered heterocyclyloxy-C$_{1-4}$-alkoxy, cycloalkyloxy-C$_{1-3}$-alkoxy, 5-6 membered heterocyclyloxy, and C$_{3-6}$-cycloalkyloxy;

and pharmaceutically acceptable derivatives thereof.

The invention also relates to compounds of Formula IV wherein Z is CH; in conjunction with any of the above or below embodiments.

The invention also relates to compounds of Formula IV wherein $Y^a$ is selected from a direct bond, —CO$_2$— and —C(=O)NH—; in conjunction with any of the above or below embodiments.

The invention also relates to compounds of Formula IV wherein $R^1$ is selected from ethyl, isopropyl, isobutyl, (CH$_3$)$_3$CCH$_2$—, and dimethylamino; in conjunction with any of the above or below embodiments.

The invention also relates to compounds of Formula IV wherein R' is selected from cyclopropyl, cyclobutyl, cyclopentyl and cyclohexyl; in conjunction with any of the above or below embodiments.

The invention also relates to compounds of Formula IV wherein R' is cyclopropyl or cyclopentyl; in conjunction with any of the above or below embodiments.

The invention also relates to compounds of Formula IV wherein R' is selected from 1-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; in conjunction with any of the above or below embodiments.

The invention also relates to compounds of Formula IV wherein R' is selected from phenyl, 2-fluorophenyl, 3-fluorophenyl, 4-fluorophenyl, 4-methylphenyl, 4-trifluoromethylphenyl, and 4-(dimethylamino)phenyl; in conjunction with any of the above or below embodiments.

The invention also relates to compounds of Formula IV wherein $R^8$ is H; in conjunction with any of the above or below embodiments.

The invention also relates to compounds of Formula IV wherein $R^9$ is H, methyl or fluoro; in conjunction with any of the above or below embodiments.

The invention also relates to compounds of Formula IV wherein $R^{10a}$ and $R^{10d}$ are both H; and wherein $R^{10b}$ and $R^{10c}$ are independently selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy; in conjunction with any of the above or below embodiments.

The invention also relates to compounds of Formula IV wherein $R^{10c}$ is methoxy; in conjunction with any of the above or below embodiments.

The invention also relates to compounds of Formula IV and pharmaceutically acceptable salts thereof selected from
1-{3-Fluoro-4-[6-methoxy-7-(3-morpholin-4-yl-propoxy)-quinolin-4-yloxy]-phenyl}-4-(methoxy-phenyl-methyl)-pyrrolidin-2-one;
1-[4-(6,7-Dimethoxy-quinolin-4-yloxy)-3-fluoro-phenyl]-4-(phenyl-propoxy-methyl)-pyrrolidin-2-one; and
4-Benzyl-1-{3-fluoro-4-[6-methoxy-7-(3-morpholin-4-yl-propoxy)-quinolin-4-yloxy]-phenyl}-pyrrolidin-2-one.

The invention also relates to compounds of Formula V

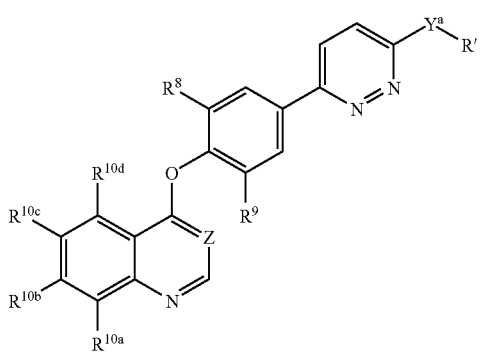

wherein $Y^a$ is a direct bond, $-NR^b(CH_2)_p-$ or $-CH_2-$;
  wherein p is 0, 1, 2, or 3; wherein $R^b$ is H or $C_{1-3}$-alkyl,
wherein Z is CH or N;
wherein R' is selected from H, $C_{1-6}$-alkyl, di-$C_{1-3}$-alkylamino and an unsubstituted or substituted ring selected from phenyl, $C_{3-6}$-cycloalkyl, pyrrolidinyl, piperidinyl, piperazinyl, 2,3-dihydroindolyl, pyrrolyl, imidazolyl, pyrazolyl, pyrazinyl, pyrimidinyl, pyridyl, quinolinyl, isoquinolinyl, 2,3-dihydrobenzofuryl, 2,3-dihydro-1,4-benzodioxinyl, 1,3-benzodioxolyl, isoxazolyl, isothiazolyl, oxazolyl, thiazolyl, furanyl, and thienyl;
wherein $R^8$ is selected from H, fluoro, chloro and methyl;
wherein $R^9$ is selected from H, methyl and fluoro; and
wherein $R^{10a}$, $R^{10b}$, $R^{10c}$ and $R^{10d}$ is each independently selected from $C_{1-3}$-alkoxy, $C_{1-3}$-alkylamino-$C_{1-3}$-alkoxy, 5-6 membered heterocyclyl-$C_{1-3}$-alkoxy, $C_{4-6}$-cycloalkyl-$C_{1-3}$-alkoxy, 5-6 membered heterocyclyl-$C_{1-3}$-(hydroxyalkoxy), $C_{3-6}$-cycloalkyl-$C_{1-3}$-(hydroxyalkoxy), $C_{1-2}$-alkoxy-$C_{1-3}$-alkoxy, phenyloxy-$C_{1-3}$alkoxy, 5-6 membered heterocyclyloxy-$C_{1-4}$-alkoxy, cycloalkyloxy-$C_{1-3}$-alkoxy, 5-6 membered heterocyclyloxy, and $C_{3-6}$-cycloalkyloxy;

and pharmaceutically acceptable derivatives thereof.

The invention also relates to compounds of Formula V wherein Z is CH; in conjunction with any of the above or below embodiments.

The invention also relates to compounds of Formula V wherein $Y^a$ is selected from a direct bond, $-N(CH_3)-$, $-N(CH_2CH_2CH(CH_3)_2)-$, $-NHCH_2-$, $-NH(CH_2)_2-$, $-NHCH_2(CH_3)-$, $-NH-$ and $-CH_2-$; in conjunction with any of the above or below embodiments.

The invention also relates to compounds of Formula V wherein R' is selected from ethyl, isopropyl, isobutyl, $(CH_3)_3CCH_2-$, and dimethylamino; in conjunction with any of the above or below embodiments.

The invention also relates to compounds of Formula V wherein R' is selected from cyclopropyl, cyclobutyl, cyclopentyl and cyclohexyl; in conjunction with any of the above or below embodiments.

The invention also relates to compounds of Formula V wherein R' is cyclopropyl or cyclopentyl; in conjunction with any of the above or below embodiments.

The invention also relates to compounds of Formula V wherein R' is selected from 1-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; in conjunction with any of the above or below embodiments.

The invention also relates to compounds of Formula V wherein R' is selected from phenyl, 2-fluorophenyl, 3-fluorophenyl, 4-fluorophenyl, 4-methylphenyl, 4-trifluoromethylphenyl, and 4-(dimethylamino)phenyl; in conjunction with any of the above or below embodiments.

The invention also relates to compounds of Formula V wherein $R^8$ is H; in conjunction with any of the above or below embodiments.

The invention also relates to compounds of Formula V wherein $R^9$ is H, methyl or fluoro; in conjunction with any of the above or below embodiments.

The invention also relates to compounds of Formula V wherein $R^{10a}$ and $R^{10d}$ are both H; and wherein $R^{10b}$ and $R^{10c}$ are independently selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl)propoxy, triazinylpropoxy, 3-(piperidin-4-yl)propoxy, dimethylaminoethoxy, dimethylaminopropoxy and methoxy; in conjunction with any of the above or below embodiments.

The invention also relates to compounds of Formula V wherein $R^{10c}$ is methoxy; in conjunction with any of the above or below embodiments.

The invention also relates to compounds of Formula V and pharmaceutically acceptable salts thereof selected from
6-(4-((6,7-bis(methoxy)-4-quinolinyl)oxy)-3-fluorophenyl)-N-(2-chlorophenyl)-3-pyridazinamine; and
6-(4-((6,7-bis(methoxy)-4-quinolinyl)oxy)-3-fluorophenyl)-N-(3-fluorophenyl)-3-pyridazinamine.

Indications

Compounds of the present invention would be useful for, but not limited to, the prevention or treatment of angiogenesis related diseases. The compounds of the invention have kinase inhibitory activity, such as VEGFR/KDR and/or c-Met inhibitory activity. The compounds of the invention are useful in therapy as antineoplasia agents or to minimize deleterious effects of VEGF and/or HGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermatomyositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of subcutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

The compounds of the present invention are also useful in the reduction of blood flow in a tumor in a subject.

The compounds of the present invention are also useful in the reduction of metastasis of a tumor in a subject.

The compounds of this invention may also act as inhibitors of other protein kinases, e.g. tie-2, lck, src, fgf, c-Met, ron, ckit and ret, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Where the plural form is used for compounds, salts, and the like, this is taken to mean also a single compound, salt and the like.

Definitions

"Angiogenesis" is defined as any alteration of an existing vascular bed or the formation of new vasculature which benefits tissue perfusion. This includes the formation of new vessels by sprouting of endothelial cells from existing blood vessels or the remodeling of existing vessels to alter size, maturity, direction or flow properties to improve blood perfusion of tissue.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind a HGF receptor. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified from a natural source, chemically synthesized or recombinantly produced. Human HGF is encoded by the cDNA sequence published by Miyazawa et al. (1989), supra, or Nakamura et al. (1989), supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The terms "hepatocyte growth factor" and "HGF" specifically include the delta 5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as p190.sup.MET. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and more preferably at least about 75% sequence homology with any domain of the human c-Met amino acid sequence published in Rodrigues et al., Mol. Cell. Biol., 11:2962-2970 (1991); Park et al., Proc. Natl. Acad. Sci., 84:6379-6383 (1987); or Ponzetto et al., Oncogene, 6:553-559 (1991).

The terms "agonist" and "agonistic" when used herein refer to or describe a molecule which is capable of, directly or indirectly, substantially inducing, promoting or enhancing HGF biological activity or HGF receptor activation.

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by increased levels of HGF or expression of c-Met in the mammal.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

Given that elevated levels of c-Met and HGF are observed in hypertension, arteriosclerosis, myocardial infarction, and rheumatoid arthritis, nucleic acid ligands will serve as useful therapeutic agents for these diseases.

The term "treatment" includes therapeutic treatment as well as prophylactic treatment (either preventing the onset of disorders altogether or delaying the onset of a pre-clinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3, 4-thiadiazolyl, 1,2,5-thiadiazolyl].

The term heterocyclyl also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," denotes a sulfonyl radical substituted with an amine radical, forming a sulfonamide (—$SO_2NH_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The term "aminocarbonyl" denotes an amide group of the formula —C(=O)$NH_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The term "Formulas I-V" includes any sub formulas.

The compounds of the invention are endowed with kinase inhibitory activity, such as KDR and/or c-Met inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of KDR and/or c-Met.

The present invention comprises a pharmaceutical composition comprising a therapeutically-effective amount of a compound of Formulas I-V in association with a least one pharmaceutically-acceptable carrier, adjuvant or diluent.

The present invention also comprises a method of treating angiogenesis related disorders in a subject having or susceptible to such disorder, the method comprising treating the subject with a therapeutically-effective amount of a compound of Formula I-V.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpirin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with VEGFR inhibitors including N-(4-chlorophenyl)-4-(4-pyridinylmethyl)-1-phthalazinamine;

4-[4-[[[[4-chloro-3-(trifluoromethyl)phenyl]amino]carbonyl]amino]phenoxy]-N-methyl-2-pyridinecarboxamide;

N-[2-(diethylamino)ethyl]-5-[(5-fluoro-1,2-dihydro-2-oxo-3H-indol-3-ylidene)methyl]-2,4-dimethyl-1H-pyrrole-3-carboxamide;

3-[(4-bromo-2,6-difluorophenyl)methoxy]-5-[[[[4-(1-pyrrolidinyl)butyl]amino]carbonyl]amino]-4-isothiazolecarboxamide;

N-(4-bromo-2-fluorophenyl)-6-methoxy-7-[(1-methyl-4-piperidinyl)methoxy]-4-quinazolinamine;

3-[5,6,7,13-tetrahydro-9-[(1-methylethoxy)methyl]-5-oxo-12H-indeno[2,1-a]pyrrolo[3,4-c]carbazol-12-yl]propyl ester N,N-dimethyl-glycine;

N-[5-[[[5-(1,1-dimethylethyl)-2-oxazolyl]methyl]thio]-2-thiazolyl]-4-piperidinecarboxamide;

N-[3-chloro-4-[(3-fluorophenyl)methoxy]phenyl]-6-[5-[[[2-(methylsulfonyl)ethyl]amino]methyl]-2-furanyl]-4-quinazolinamine 4-[(4-Methyl-1-piperazinyl)methyl]-N-[4-methyl-3-[[4-(3-pyridinyl)-2-pyrimidinyl]amino]-phenyl]benzamide N-(3-chloro-4-fluorophenyl)-7-methoxy-6-[3-(4-morpholinyl)propoxy]-4-quinazolinamine N-(3-ethynylphenyl)-6,7-bis(2-methoxyethoxy)-4-quinazolinamine N-(3-((((2R)-1-methyl-2-pyrrolidinyl)methyl)oxy)-5-(trifluoromethyl)phenyl)-2-((3-(1,3-oxazol-5-yl)phenyl)amino)-3-pyridinecarboxamide;

2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide;

N-[3-(Azetidin-3-ylmethoxy)-5-trifluoromethyl-phenyl]-2-(4-fluoro-benzylamino)-nicotinamide.

6-fluoro-N-(4-(1-methylethyl)phenyl)-2-((4-pyridinylmethyl)amino)-3-pyridinecarboxamide;

2-((4-pyridinylmethyl)amino)-N-(3-(((2S)-2-pyrrolidinylmethyl)oxy)-5-(trifluoromethyl)phenyl)-3-pyridinecarboxamide;

N-(3-(1,1-dimethylethyl)-1H-pyrazol-5-yl)-2-((4-pyridinylmethyl)amino)-3-pyridinecarboxamide;

N-(3,3-dimethyl-2,3-dihydro-1-benzofuran-6-yl)-2-((4-pyridinylmethyl)amino)-3-pyridinecarboxamide;

N-(3-((((2S)-1-methyl-2-pyrrolidinyl)methyl)oxy)-5-(trifluoromethyl)phenyl)-2-((4-pyridinylmethyl)amino)-3-pyridinecarboxamide;

2-((4-pyridinylmethyl)amino)-N-(3-((2-(1-pyrrolidinyl)ethyl)oxy)-4-(trifluoromethyl)phenyl)-3-pyridinecarboxamide;

N-(3,3-dimethyl-2,3-dihydro-1H-indol-6-yl)-2-((4-pyridinylmethyl)amino)-3-pyridinecarboxamide;

N-(4-(pentafluoroethyl)-3-(((2S)-2-pyrrolidinylmethyl)oxy)phenyl)-2-((4-pyridinylmethyl)amino)-3-pyridinecarboxamide;

N-(3-((3-azetidinylmethyl)oxy)-5-(trifluoromethyl)phenyl)-2-((4-pyridinylmethyl)amino)-3-pyridinecarboxamide;

N-(3-(4-piperidinyloxy)-5-(trifluoromethyl)phenyl)-2-((2-(3-pyridinyl)ethyl)amino)-3-pyridinecarboxamide;

N-(4,4-dimethyl-1,2,3,4-tetrahydro-isoquinolin-7-yl)-2-(1H-indazol-6-ylamino)-nicotinamide;

2-(1H-indazol-6-ylamino)-N-[3-(1-methylpyrrolidin-2-ylmethoxy)-5-trifluoromethyl-phenyl]-nicotinamide;

N-[1-(2-dimethylamino-acetyl)-3,3-dimethyl-2,3-dihydro-1H-indol-6-yl]-2-(1H-indazol-6-ylamino)-nicotinamide;

2-(1H-indazol-6-ylamino)-N-[3-(pyrrolidin-2-ylmethoxy)-5-trifluoromethyl-phenyl]-nicotinamide;

N-(1-acetyl-3,3-dimethyl-2,3-dihydro-1H-indol-6-yl)-2-(1H-indazol-6-ylamino)-nicotinamide;

N-(4,4-dimethyl-1-oxo-1,2,3,4-tetrahydro-isoquinolin-7-yl)-2-(1H-indazol-6-ylamino)-nicotinamide;

N-[4-(tert-butyl)-3-(3-piperidylpropyl)phenyl][2-(1H-indazol-6-ylamino)(3-pyridyl)]carboxamide;

N-[5-(tert-butyl)isoxazol-3-yl][2-(1H-indazol-6-ylamino)(3-pyridyl)]carboxamide; and N-[4-(tert-butyl)phenyl][2-(1H-indazol-6-ylamino)(3-pyridyl)]carboxamide.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. No. 6,630,500, U.S. Pat. No. 6,515,004, U.S. Pat. No. 6,713,485, U.S. Pat. No. 5,521,184, U.S. Pat. No. 5,770,599, U.S. Pat. No. 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufamide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, metallomatrix proteases inhibitors (MMP), COX-2 inhibitors including celecoxib, NSAID's, or $\alpha_v\beta_3$ inhibitors.

The present invention comprises processes for the preparation of a compound of Formula I-V.

Also included in the family of compounds of Formula I-V are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I-V may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I-V include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I-V. When a basic group and an acid group are present in the same molecule, a compound of Formula I-V may also form internal salts.

General Synthetic Procedures

The compounds of the invention can be synthesized according to the following procedures of Schemes 1-13, wherein the substituents are as defined for Formulas I-V, above, except where further noted.

The following abbreviations are used throughout the specification:
HOAC—acetic acid
MeCN—acetonitrile
$NH_4Cl$—ammonium chloride
Ar—argon
HATU—O-(7-azabenzotriazol-1-yl)-N,N,N',N'-tetramethyluroniumhexafluorophosphate
PyBop—benzotriazol-1-yl-oxy-tripyrrolidino-phosphonium hexafluorophosphate
$Pd_2(dba)_3$—bis(dibenzylideneacetone)palladium
BINAP—2,2'-bis(diphenylphosphino)-1,1'-binaphthyl
TEAC—bis(tetra-ethylammonium)carbonate
$BBr_3$—boron tribromide
BSA—bovine serum albumin
$Br_2$—bromine
$Cs_2CO_3$—cesium carbonate
$CHCl_3$—chloroform
Cu—copper
CuI—copper(I) iodide
$Et_2O$—diethyl ether
DBU—1,8-diazabicyclo[5.4.0]undec-7-ene
DIBAL—diisobutylaluminum hydride
DIAD—diisopropyl azodicarboxylate
DIEA—diisopropylethylamine
DMF—dimethylformamide
DMAP—4-dimethylaminopyridine
DMSO—dimethylsulfoxide
EDC, EDCI—1-(3-dimethylaminopropyl)-3-ethylcarbodiimide hydrochloride
dppa—diphenylphosphoryl azide
EtOAc—ethyl acetate
FBS—fetal bovine serum
g—gram
h—hour
HBr—hydrobromic acid
HCl—hydrochloric acid
HOBt—1-hydroxybenzotriazole hydrate
$H_2$—hydrogen
$H_2O_2$—hydrogen peroxide
LiHMDS—lithium bis(trimethylsilyl)-amide
MCPBA—meta-chloroperbenzoic acid
$MgSO_4$—magnesium sulfate
MeOH—methanol
MeI—methyl iodide
$CH_2Cl_2$, DCM—methylene chloride
NMP—N-methylpyrrolidinone
ML—milliliter
$N_2$—nitrogen
Pd/C—palladium on carbon
$Pd(OAc)_2$—palladium acetate
$Pd(OH)_2$—palladium hydroxide
$Pd(PPh_3)_4$—palladium tetrakis triphenylphosphine
$Pd(dppf)Cl_2$—1,1-bis(diphenylphosphino)ferrocene palladium chloride
PBS—phosphate buffered saline
$POCl_3$—phosphorous oxychloride
$K_2CO_3$—potassium carbonate
RT—room temperature
$NaHCO_3$—sodium bicarbonate
$NaBH_4$—sodium borohydride
NaOtBu—sodium tert-butoxide
NaOH—sodium hydroxide
NaH—sodium hydride
NaI—sodium iodide
$Na_2SO_4$—sodium sulfate
TBTU—O-benzotriazol-1-yl-N,N,N',N'-tetramethyluronium tetrafluoroborate
THF—tetrahydrofuran
$Et_3N$, TEA—triethylamine
TFA—trifluoroacetic acid
$P(t-bu)_3$—tri(tert-butyl)phosphine
$H_2O$—water

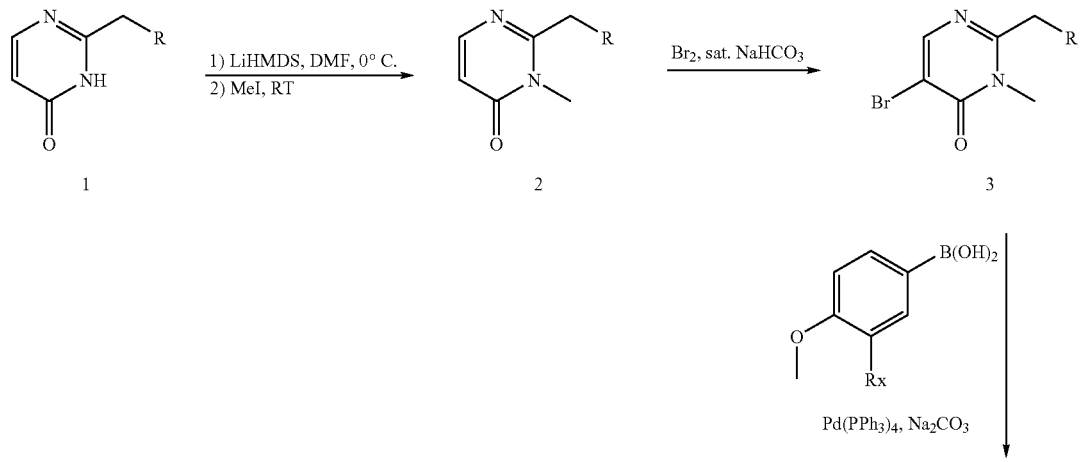

Scheme 1

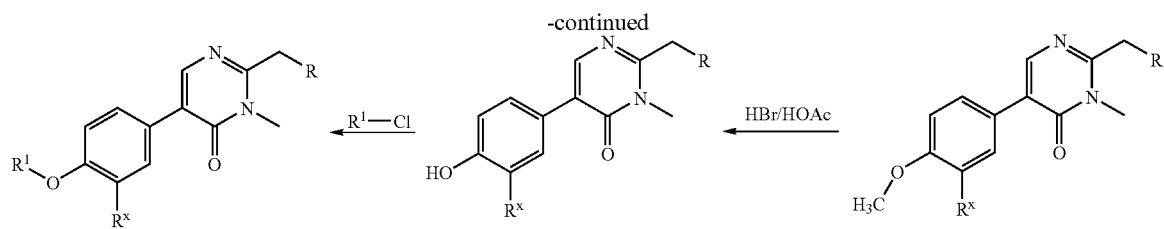

Substituted pyrimidinones 6 can be prepared by the process outlined in Scheme 1. Alkylation of pyrimidinone 1 (prepared similar to that described in WO 94/26715) such as with an alkyl halide in the presence of base (e.g. $Cs_2CO_3$ or LiHMDS) at a temperature of about RT, yields the 3-alkylpyrimidinone 2. Bromination of the 3-alkylpyrimidinone 2, such as with $Br_2$ in the presence of base (e.g. $NaHCO_3$) at a temperature of about RT, provides the 5-bromo-3-alkylpyrimidinone 3. For compounds of the invention where X is O, coupling the 5-bromo-3-alkylpyrimidinone 3 such as with Suzuki coupling with an appropriate boronic acid, provides the 5-phenylpyridinone 4. The reaction is maintained at a temperature>about 50° C., preferably at a temperature above about 75° C., more preferably at about 90° C. The phenol 5 is prepared by dealkylation of the 5-(4-methoxyphenyl)pyridinone 4, such as by treatment with HBr at a temperature above about 100° C., preferably at about 130° C. Treatment of phenol 5 with a halo-substituted ring, such as in the presence of DMAP and NMP, provides compounds 6. Preferably the reaction is at a temperature above RT, preferably above about 50° C., more preferably at about 90° C. More preferably the reaction is heated using a microwave (150 W).

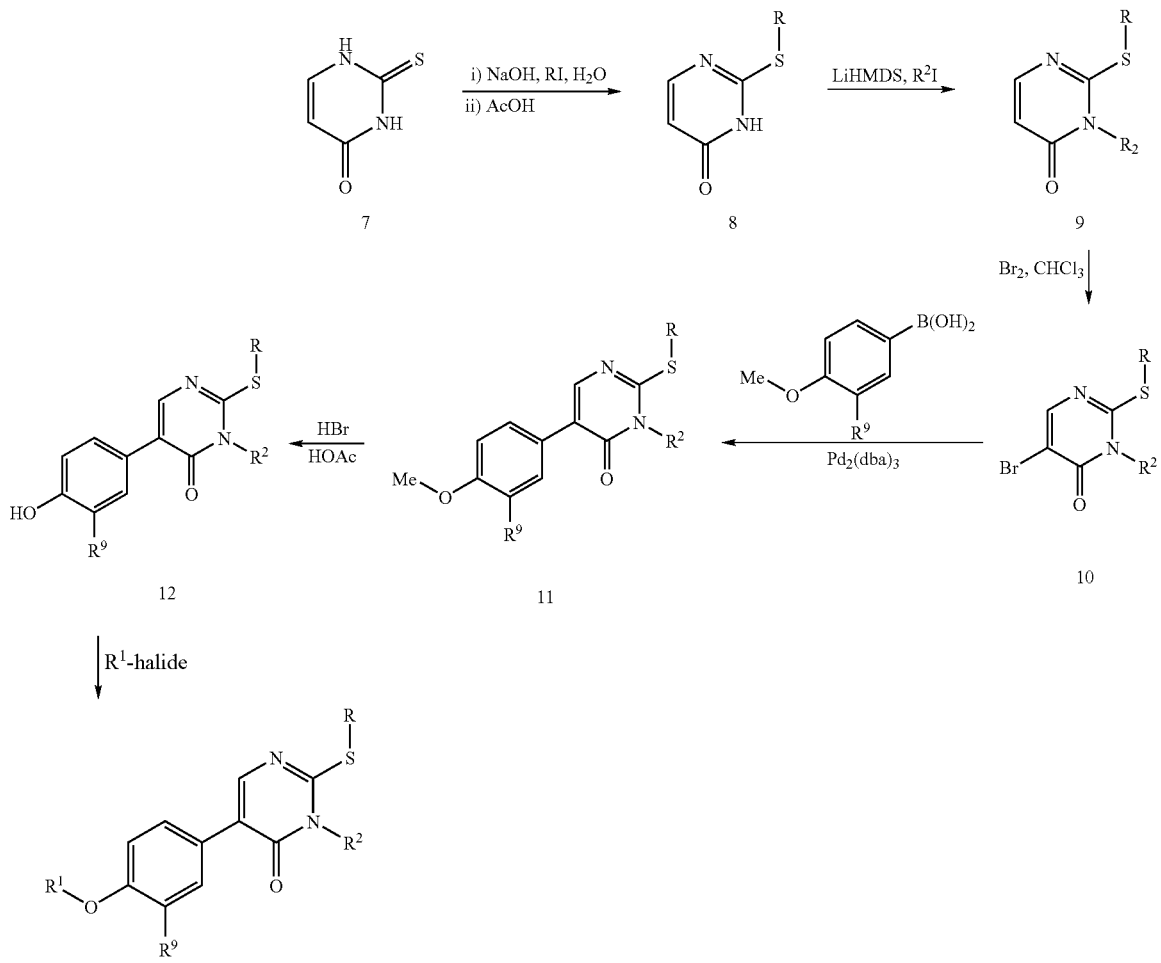

Alternatively, compounds of the invention where Y is S can be prepared by the method described in Scheme 2. Alkylation of the thione 7 (prepared following the procedure of J. Spychala, Syn. Comm., 27(11):1943-1949 (1997), provides the 2-alkylthio-pyrimidinone 8. Subsequent steps similar to that described in Scheme 1 yields the 2-substituted thio-5-(4-hydroxyphenyl) pyrimidinone 12. Further treatment with the halide yield compounds 13.

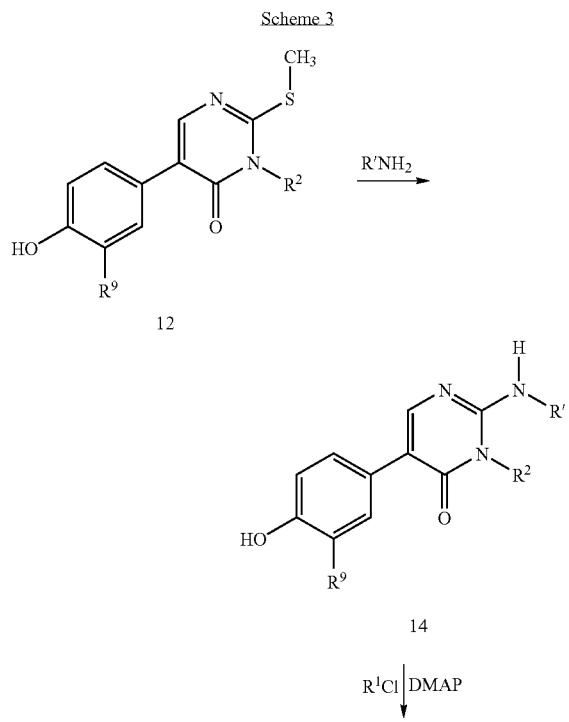

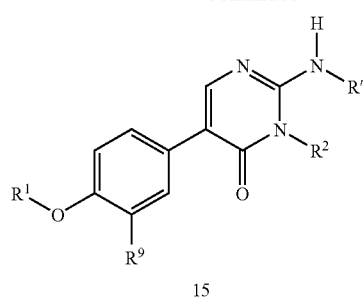

Compounds of the invention where Y is —NH— and X is O can be prepared as shown in Scheme 3. The 2-methylthiopyrimdinone 12 is treated with the appropriate amine, such as in the presence of acid (e.g. HCl) and heated at a temperature of above about 50° C., preferably above about 100° C., more preferably at about 120° C. The reaction can be heated with a microwave (100 W) to form amine 14. Coupling of amine 14 with the appropriate chloride, similar to the method described in Scheme 1 yields compound 15.

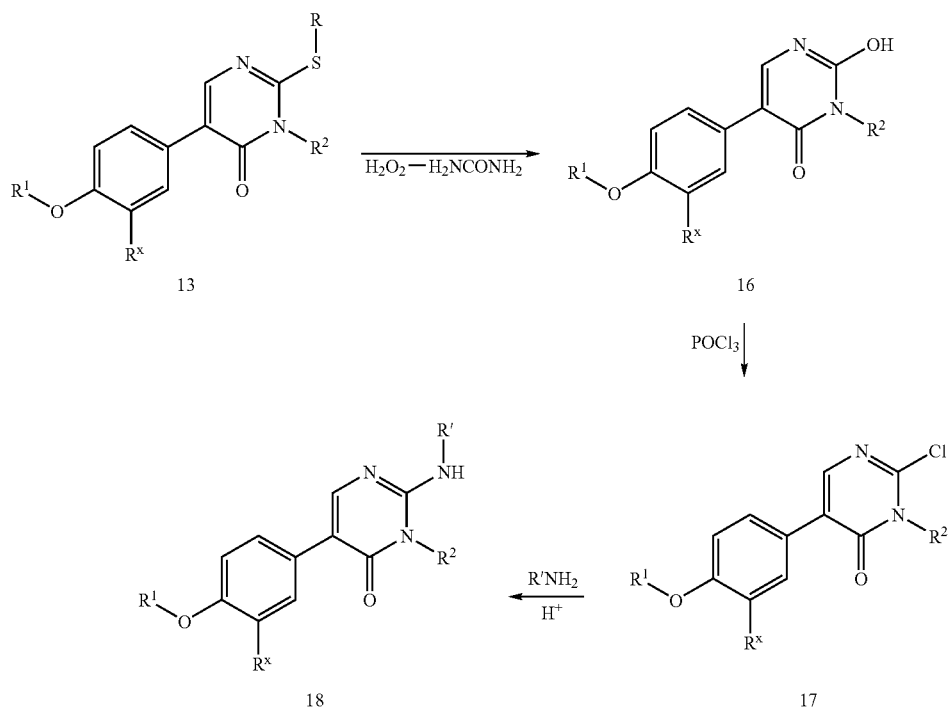

Alternatively, compounds of the invention where Y is —NH— and X is O can be prepared as shown in Scheme 4. The 2-methylthiopyrimdinone 13 (R is CH$_3$) is derivatized to the 2-chloropyrimidinone 17 via the hydroxy intermediate 16 such as by treatment of the thio compound with urea hydrogen peroxide and TFAA, preferably at about RT; followed by POCl$_3$ and base. The chlorination is performed at a temperature above about 50° C., preferably above about 100° C., more preferably at about 125° C. Treatment of the 2-chloropyrimidinone 17 with the suitable amine, such as in the presence of acid (e.g. HCl) preferably at a temperature above about 50° C., more preferably about 60° C., provides compounds 17. Alternatively the reaction is heated with a microwave (60 W).

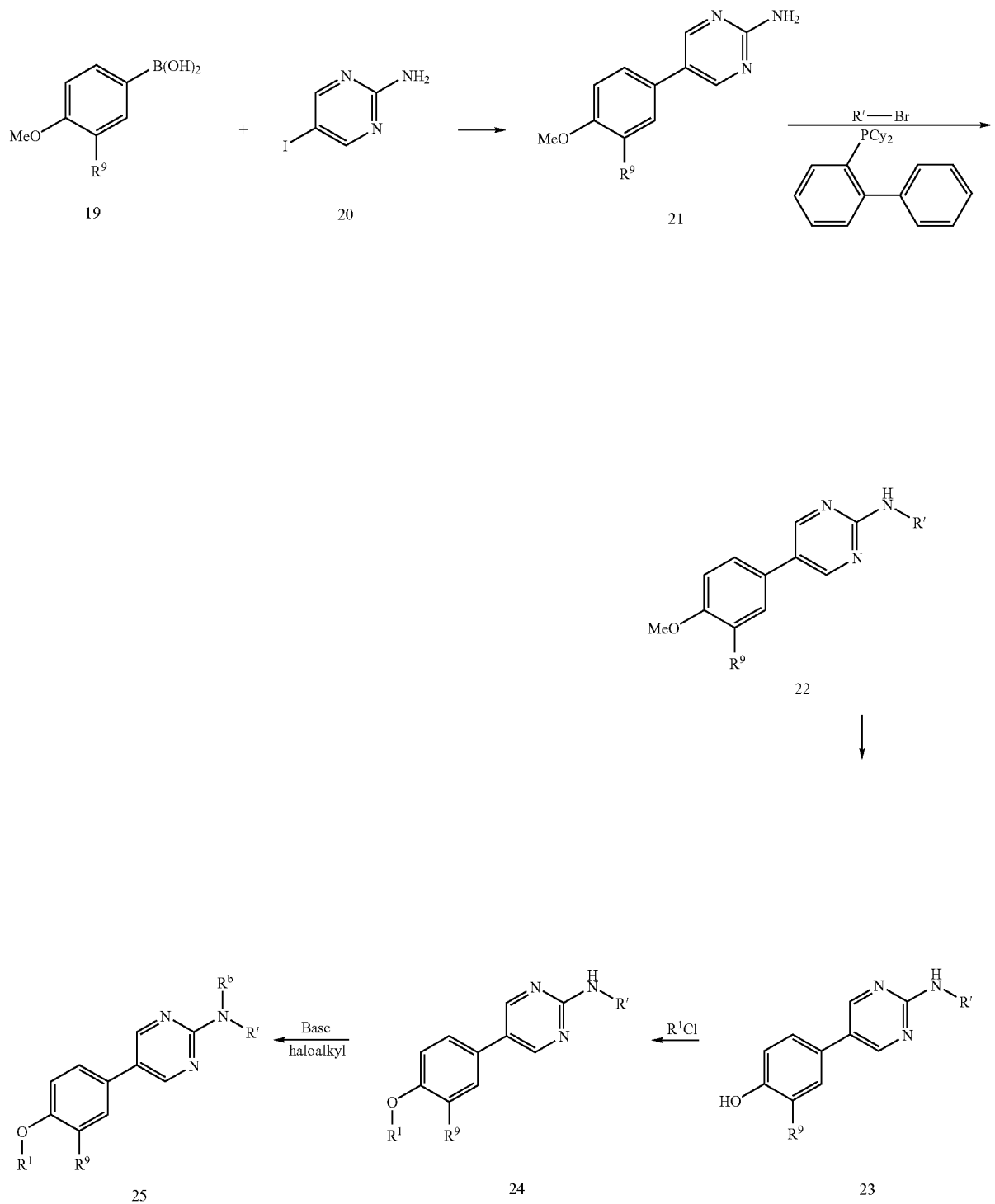

Pyrimidine compounds of the invention can be prepared such as by the method described in Scheme 5. Suzuki coupling of boronic acids 19 with 2-amino-5-halopyrimidine 20, such as in the presence of a Pd catalyst (e.g. Pd(PPh)$_4$) and at a temperature above about 50° C., preferably at about 80° C., provides the bicyclic compound 21. Treatment of the amine 21 with an appropriate halo compound, such as an iodobenzene or bromo derivative, in the presence of a Pd catalyst (e.g. Pd(OAc)$_2$), 2-biscyclohexyl 1,1-biphenyl phosphine and KO$^t$Bu, in an appropriate solvent such as dimethylacetamide and toluene yields the substituted amine 22. The reaction is maintained at a temperature above about 100° C., preferably at about 200° C., and preferably heated in a microwave. Dealkylation of the methoxy compound 22, such as with thiophenol and base (e.g. K$_2$CO$_3$) in a solvent such as NMP, at a temperature above about 100° C., preferably at about 120° C., provides the phenol 23. The phenol 23 is coupled with a halo-substituted ring, such as with a catalytic amount of DMAP at a temperature above about 100° C., preferably at about 180° C., and more preferably heated in a microwave, to provide pyridines 24. Further substitution of the amine can be achieved to provide compounds 25.

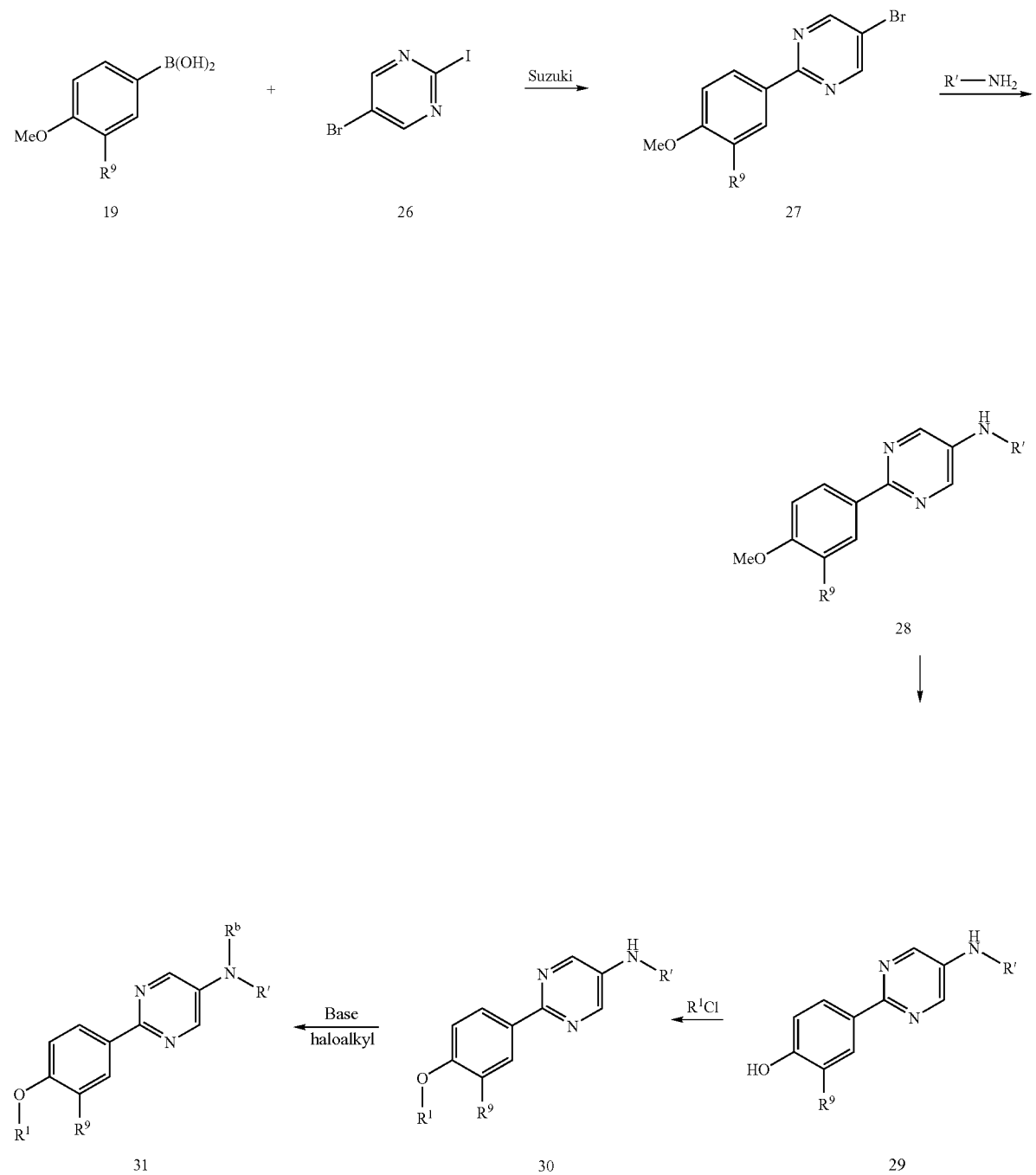

Similar to the methods described in Scheme 5, pyrimidine compounds of the invention can be prepared such as by the method described in Scheme 6. Suzuki coupling of boronic acids 19 with 2,5-dihalopyrimidine 26, such as in the presence of a Pd catalyst (e.g. Pd(dppf)Cl$_2$) and at a temperature above about 50° C., more preferably at about 80° C., provides the bicyclic compound 27. Treatment of halo compound 27 with an appropriate amine, such as an aniline, in the presence of a Pd catalyst (e.g. Pd(OAc)$_2$), BINAP and NaO$^t$Bu, in an appropriate solvent such as toluene, at a temperature above about 50° C., preferably at about 100° C., yields the substituted amine 28. Dealkylation of the methoxy compound 28, such as with thiophenol and K$_2$CO$_3$ in a solvent such as NMP, at a temperature above about 100° C., preferably at about 120° C., provides the phenol 29, which can be coupled with a halo-substituted ring, such as with a catalytic amount of DMAP at a temperature above about 50° C., preferably at about 110° C., to provide pyridines 30. Further alkylation of the amine can be achieved, such as by deprotonation with strong base (e.g. NaH) at a temperature above about RT, preferably at about 50° C., and treatment with haloalkyl (R$^b$-LG) at a temperature above about RT, preferably at about 50° C., to provide compounds 31.

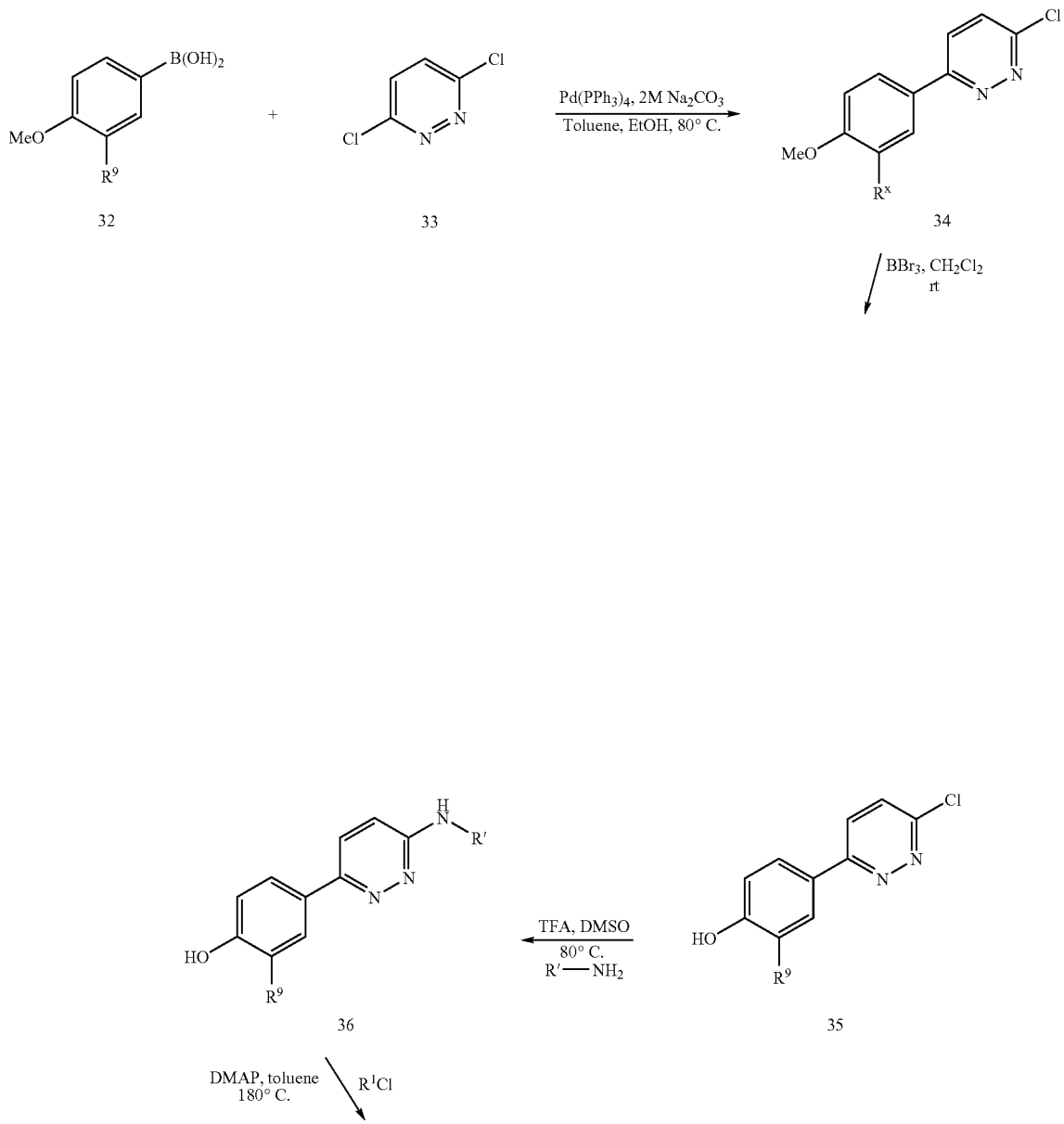

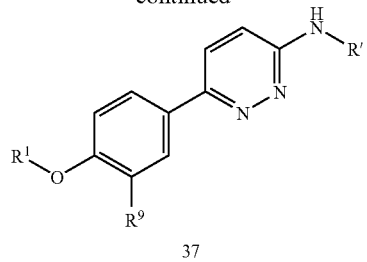

37

Similar to the methods described above, pyridazine compounds of the invention can be prepared such as by the method described in Scheme 7. Suzuki coupling of boronic acids 32 with 2,5-dihalopyrimidine 33, such as in the presence of a Pd catalyst (e.g. Pd(PPh$_3$)$_4$) and at a temperature above about 50° C., more preferably at about 80° C., provides the bicyclic compound 34. Dealkylation of the methoxy compound 34, such as with BBr$_3$ (e.g. 1M) in a solvent such as CH$_2$Cl$_2$, at a temperature of about RT, provides the phenol 35. Where Y is —NH—, amination of the chloro compound 34 with an appropriate amine, such as an aniline, in the presence of a acid (e.g. TFA) in an appropriate solvent such as DMSO, at a temperature above about 50° C., preferably at about 80° C., yields the substituted amine 36. The substituted amine 36 can be coupled with a halo-substituted ring, such as with Cu powder and base (e.g. NaOH) at a temperature above about 50° C., preferably at about 120° C., more preferably in a microwave (60 W), to provide pyridazine 37.

Where Y is —CH$_2$—, the chloro compound 34 can be alkylated, such as with B-benzyl-9-BBN and K$_2$CO$_3$ in the presence of catalytic Pd, preferably Pd(DPPF)Cl$_2$, at a temperature above about 50° C., preferably at about 65° C., to provide alkyl substituted pyridazine compounds.

Where Y is —O—, the chloro compound 34 can be substituted with alcohols, such as with Cs$_2$CO$_3$ in the presence of DMF, at a temperature above about 100° C., preferably at about 150° C., more preferably in a microwave, to provide oxy substituted pyridazine compounds. The methoxy compound can also be converted to the phenol by treatment with pyridine hydrochloride at a temperature above about 100° C., preferably above about 150° C., more preferably at about 170° C.

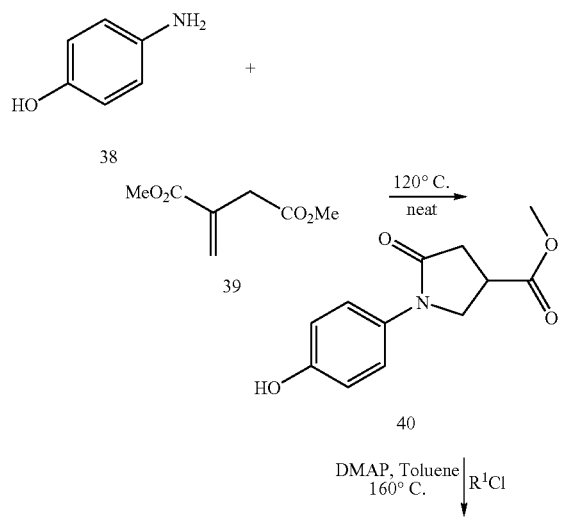

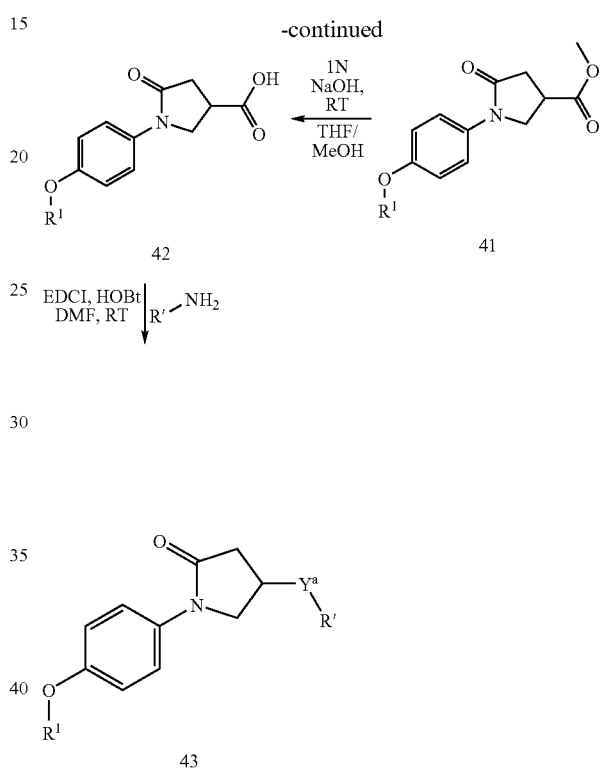

Compounds of the invention, where Y is —C(O)NH— can be prepared such as by the method described in Scheme 8. 1-(4-Hydroxyphenyl)-5-oxo-pyrrolidine-3-carboxylic acid methyl ester 40 is prepared from 4-amino-phenol 38 and 2-methylene-succinic acid dimethyl ester 39 at a temperature above about 50° C., preferably above about 100° C., more preferably at about 110° C. Coupling of the phenol 40 with a halide similar to that described in Scheme 3 yields the ether 41. De-esterification of 41, such as by treatment with base, yields the carboxylic acid 42. The acid 42 can be aminated such as with treatment with an amine in the presence of coupling reagents (e.g. EDC and HOBT) provided the amide 43.

Scheme 9

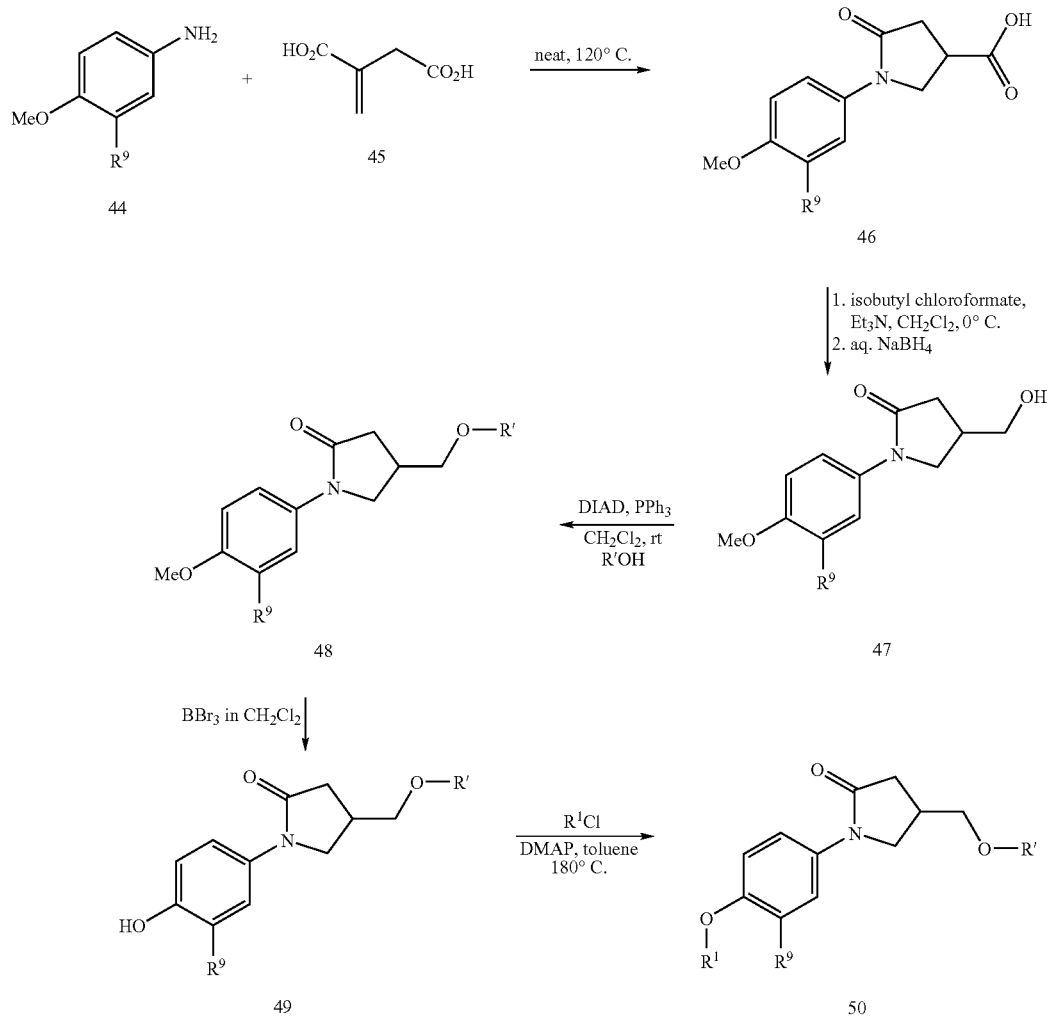

Compounds of the invention, where Y is —OCH₂— can be prepared such as by the method described in Scheme 9. The 5-oxopyrrolidine-3-carboxylic acid 46 an be prepared by reaction of 3-fluoro-4-methoxybenzenamine 44 with itaconic acid 45 at a temperature above about 50° C., preferably above about 100° C., more preferably at about 110° C. Formation of the alcohol 47 is accomplished by treatment of acid 46 first with isobutyl chloroformate in the presence of base, such as TEA, at a temperature below RT, preferably at about 0° C., followed by reduction, such as with NaBH₄. Treatment of the alcohol 47 with R'OH, such as in the presence of DIAD and PPh₃ at a temperature at about RT provided the ether 48. Conversion of the methoxy compound 48 by a method similar to that described in Scheme 7 provided the phenol 49. Treatment of the phenol 49 with the appropriate halide such in the presence of DMAP at a temperature above about 100° C., preferably at about 180° C., more preferably in a microwave, to provide the desired ethers 50.

Scheme 10

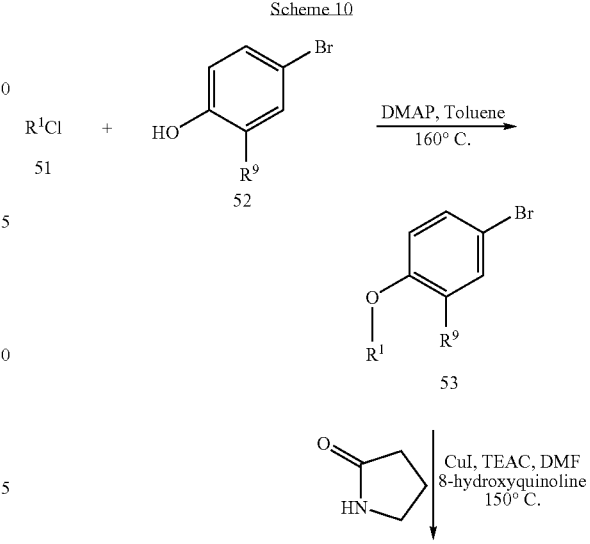

-continued

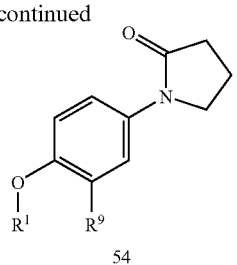

54

Compounds of the invention, where YR is H, can be prepared such as by the method described in Scheme 10. Treatment of an appropriate halide 51 is coupled with an alcohol 52 such as with DMAP at a temperature above about 100° C., preferably at about 160° C., more preferably in a microwave, to provide the desired ether 53. Treatment of the halo compound 53 with the desired cyclic amine, such as pyrrolidin-2-one, in the presence of TEAC, 8-hydroxyquinoline and CuI, at a temperature above about 100° C., preferably at about 150° C., more preferably in a microwave, provides the desired compounds 54.

Scheme 11

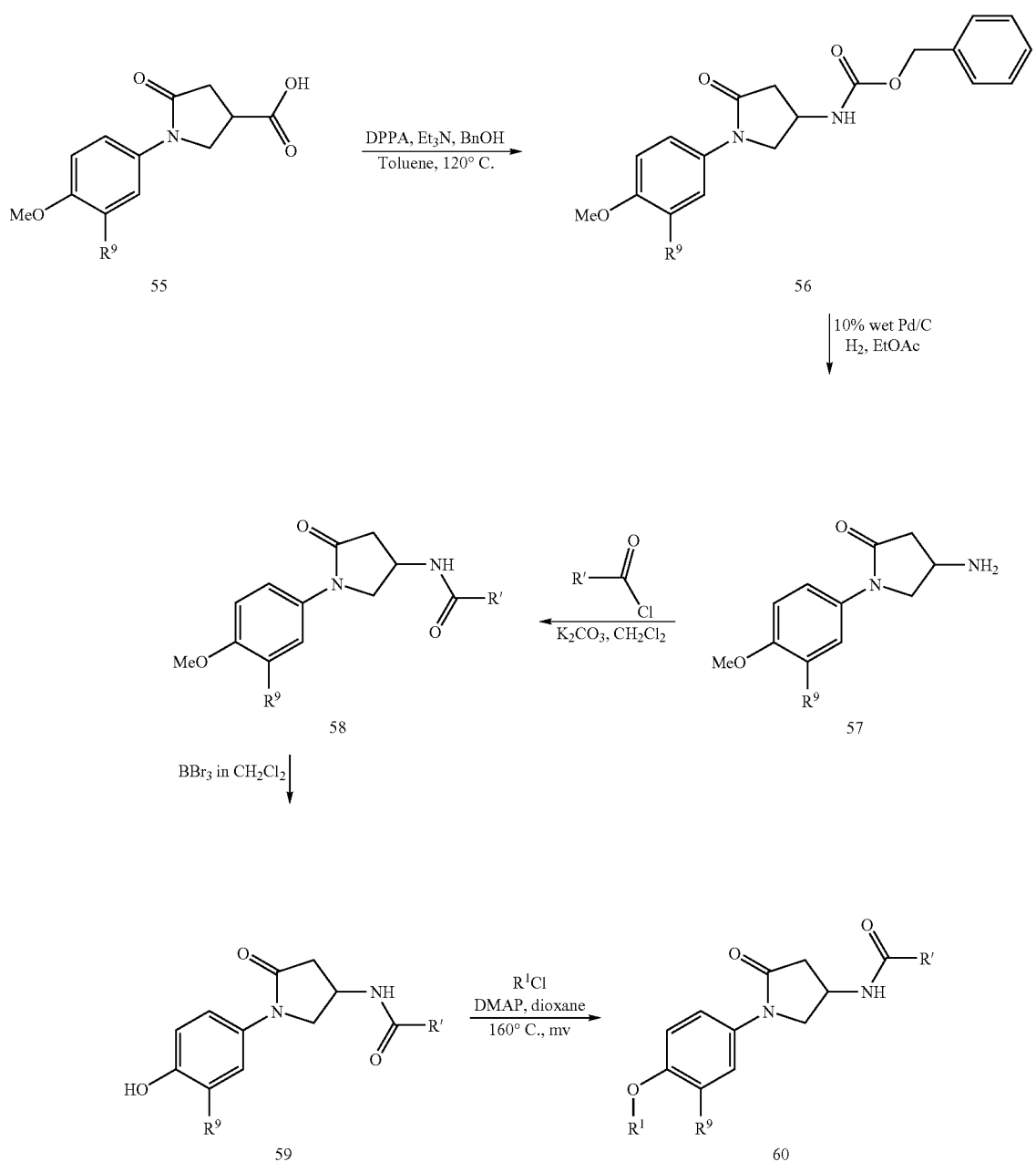

Compounds of the invention, where Y is —NHC(O)— can be prepared such as by the method described in Scheme 11. Treatment of the carboxylic acid 55 such as with TEA and an alcohol, in the presence of DPPA, at a temperature above about 50° C., preferably above about 100° C., more preferably at about 120° C. forms the protected amine 56. Deprotection, such as with Pd/C and H₂ yields the amine 57. Coupling with an appropriate carbonyl reagent, such as an acid cholide, in the presence of base, such as K₂CO₃, provide the desired amide 58. Conversion of the ether 58 to the alcohol 59, by a procedure similar to that described in Scheme 7, followed by coupling with an appropriate halide provides the pyrrolidone 60 of the invention.

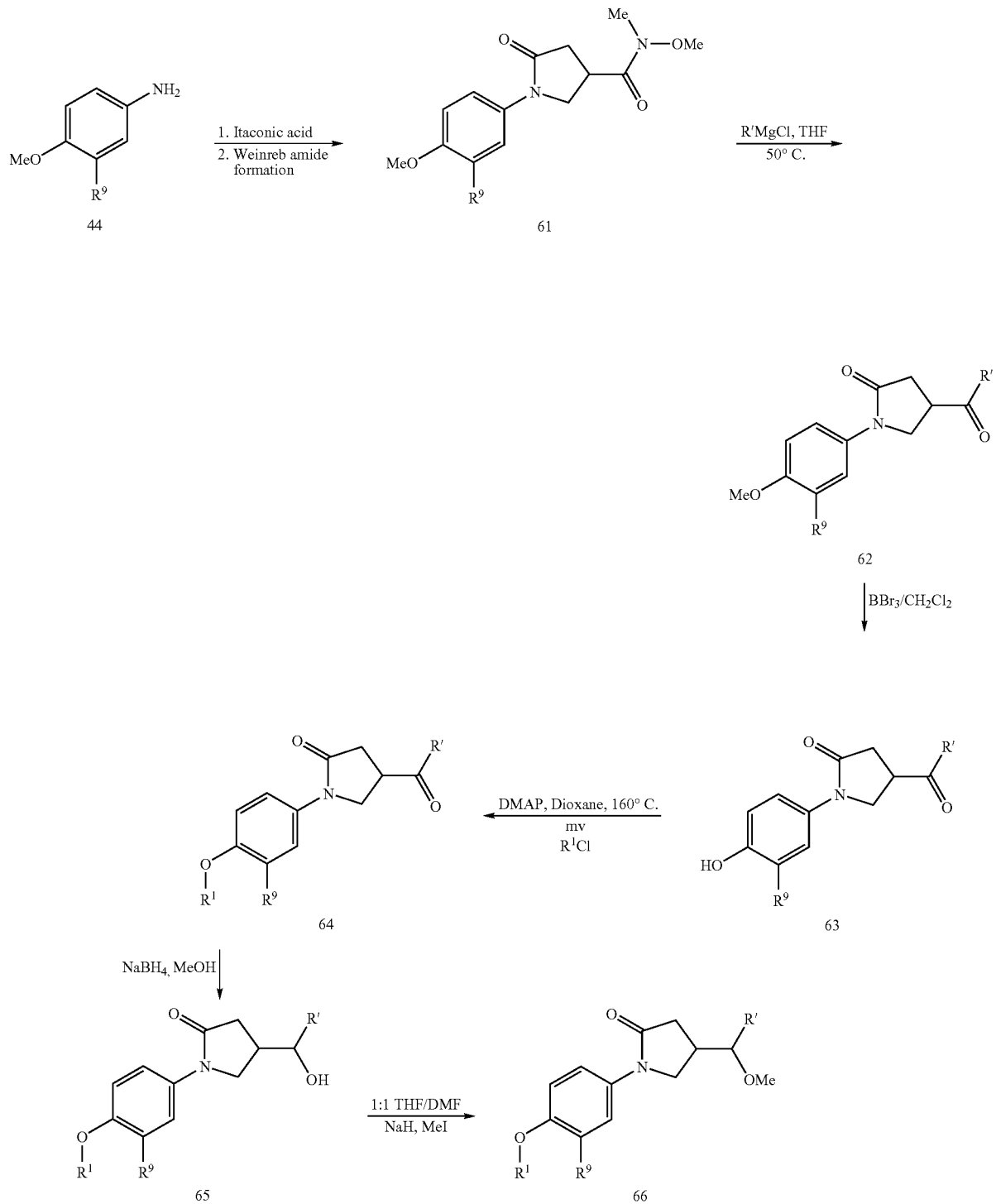

Pyrrolidones of the invention, where Y is either —C(=O)—, —CH(OH)— or —CH(OMe)-can be prepared such as by the method described in Scheme 12. Preparation of the protected carbonyl 61 such as by treatment of the amine 44 with itaconic acid and N-methoxymethanamine hydrochloride and HOBt in the presence of base, such as $Et_3N$ can be achieved at about RT. The desired substituted carbonyl compound 62 is achieved through alkylation, such as by treatment with a Grignard reagent (e.g. R'MgCl) at a temperature above about RT, preferably at about 50° C. Conversion of the ether 62 to the alcohol 63, by a procedure similar to that described in Scheme 7, followed by coupling with an appropriate halide provides the carbonyl compounds of the invention 64. Reduction of the carbonyls 64, such as by treatment with $NaBH_4$ at a temperature of about RT forms the alcohols 65. Alkylation of the alcohols 65, such as by treatment with base (e.g. NaH) followed by reaction with the appropriate alkyl halide yields the desired ether 66.

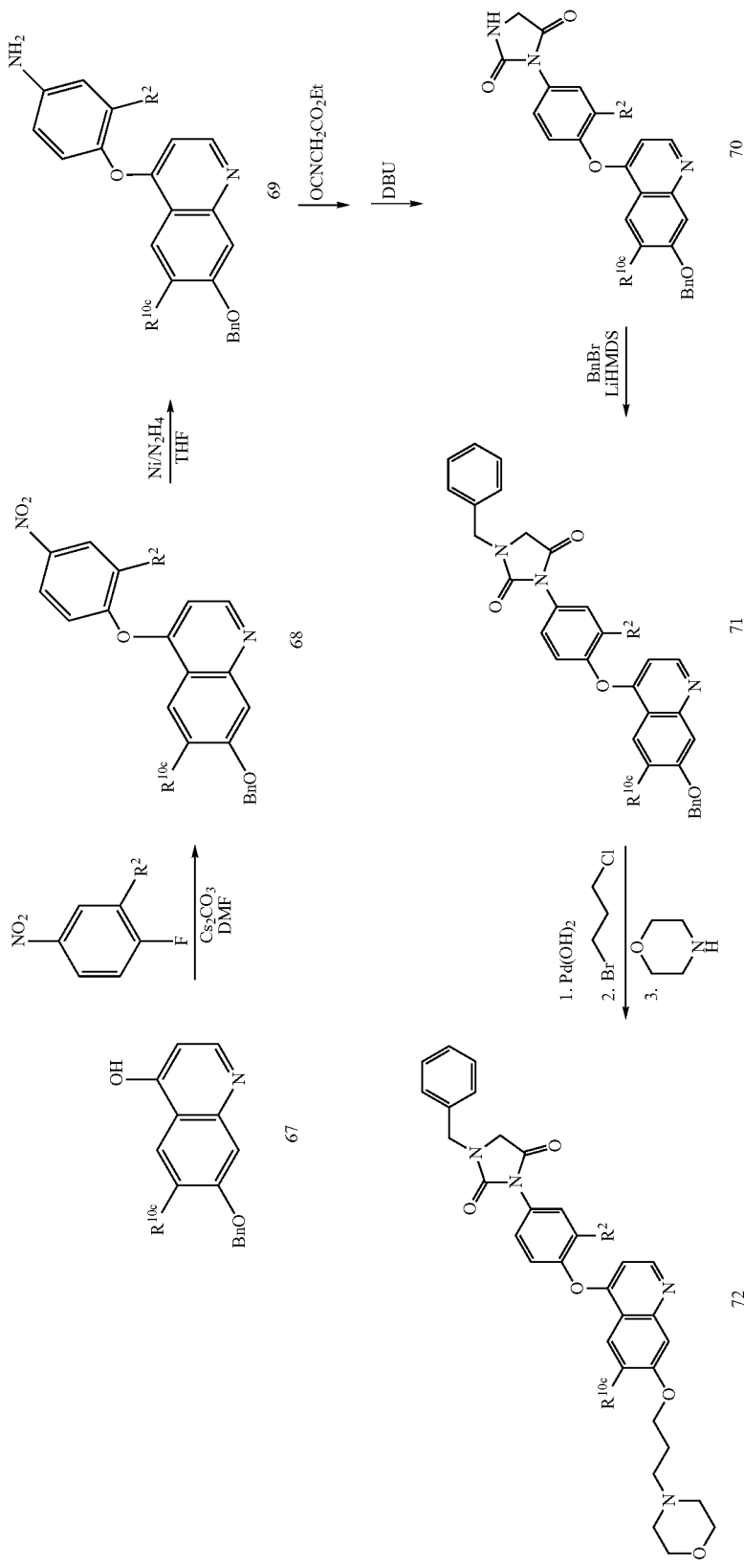

Hydantoin compounds of the invention can be prepared such as by the method described in Scheme 13. Preparation of the quinolinyl ether 68, such as through the $Cs_2CO_3$ mediated reaction of the alcohol 67 with the appropriate halo-benzene compound at a temperature above about RT, preferably at about 40° C., followed by reduction of the nitro group, such as by treatment with hydrazine in the presence of a catalyst (e.g. Raney nickel) provides the amine 69. The hydantoin 70 is formed, such as by addition of ethyl isocyanatoacetate and treatment with DBU. Alkylation to form substituted hydantoins 71 is achieved such as by treatment with an alkyl halide and LiHMDS. Alternative substitution on the quinolines ring can be achieved such as by removal of more labile groups (e.g. benzyl groups) such as by treatment with PdOH/C in an appropriate solvent such as an alcohol (e.g. MeOH) and reaction with base (e.g. $Cs_2CO_3$) and dihaloalkyls, and treatment with the resulting haloalkyl-ether with an amine (cyclic, branched or straight chain) at a temperature above about RT, preferably above about 50° C., more preferably at about 60° C., to provide the desired compound 72.

The starting compounds defined in Schemes 1-13 may also be present with functional groups in protected form if necessary and/or in the form of salts, provided a salt-forming group is present and the reaction in salt form is possible. If so desired, one compound of Formula I can be converted into another compound of Formula I or a N-oxide thereof; a compound of Formula I can be converted into a salt; a salt of a compound of Formula I can be converted into the free compound or another salt; and/or a mixture of isomeric compounds of Formula I can be separated into the individual isomers.

N-Oxides can be obtained in a known matter by reacting a compound of Formula I with hydrogen peroxide, oxone, or a peracid, e.g. mCPBA, in an inert solvent, e.g. $CH_2Cl_2$, or a mixture of $H_2O$ and an alcohol such as MeOH or EtOH, at a temperature between about −10-35° C., such as about 0° C.-RT.

If one or more other functional groups, for example carboxy, hydroxy, amino, or mercapto, are or need to be protected in a compound of Formula I or in the preparation of compounds of Formula I, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York (1973), in T. W. Greene, "Protective Groups in Organic Synthesis", Wiley, New York (1981), in "The Peptides", Volume 3, E. Gross and J. Meienhofer editors, Academic Press, London and New York (1981), in "Methoden der organischen Chemie" (Methods of organic chemistry), Houben Weyl, 4$^{th}$ edition, Volume 15/1, Georg Thieme Verlag, Stuttgart (1974), in H.-D. Jakubke and H. Jescheit, "Aminosauren, Peptide, Proteine" (Amino acids, peptides, proteins), Verlag Chemie, Weinheim, Deerfield Beach, and Basel (1982), and in Jochen Lehmann, "Chemie der Kohlenhydrate: Monosaccharide und Derivate" (Chemistry of carbohydrates: monosaccharides and derivatives), Georg Thieme Verlag, Stuttgart (1974).

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of Formula I with a salt-forming group may be prepared in a manner known per se. Acid addition salts of compounds of Formula I may thus be obtained by treatment with an acid or with a suitable anion exchange reagent. A salt with two acid molecules (for example a dihalogenide of a compound of Formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of Formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the $H^+$ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example $H_2O$, esters, typically lower alkyl-lower alkanoates, e.g., EtOAc, ethers, typically aliphatic ethers, e.g., $Et_2O$, or cyclic ethers, e.g., THF, liquid aromatic hydrocarbons, typically benzene or toluene, alcohols, typically MeOH, EtOH or 1-propanol, IPOH, nitriles, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

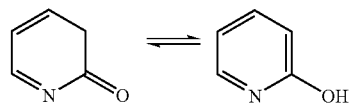

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, "Comprehensive Organic Transformations", VCH Publishers (1989); T. W. Greene and P. G. M. Wuts, "Protective Groups in Organic Synthesis", $3^{rd}$ edition, John Wiley and Sons (1999); L. Fieser and M. Fieser, "Fieser and Fieser's Reagents for Organic Synthesis", John Wiley and Sons (1994); A. Katritzky and A. Pozharski, "Handbook of Heterocyclic Chemistry", $2^{nd}$ edition (2001); M. Bodanszky, A. Bodanszky, "The Practice of Peptide Synthesis", Springer-Verlag, Berlin Heidelberg (1984); J. Seyden-Penne, "Reductions by the Alumino- and Borohydrides in Organic Synthesis", $2^{nd}$ edition, Wiley-VCH, (1997); and L. Paquette, editor, "Encyclopedia of Reagents for Organic Synthesis", John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

These detailed descriptions fall within the scope, and serve to exemplify, the above-described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification. Anhydrous solvents such as DMF, THF, $CH_2Cl_2$ and toluene were obtained from the Aldrich Chemical Company, EMD among others.

EXAMPLE 1

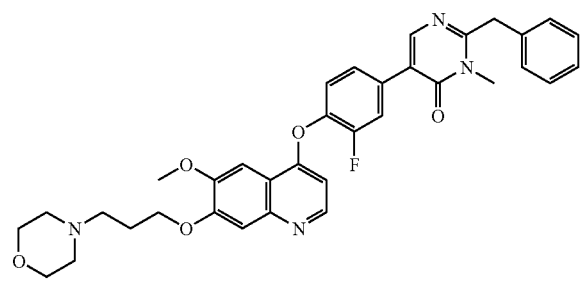

2-Benzyl-5-{3-fluoro-4-[6-methoxy-7-(3-morpholin-4-yl-propoxy)-quinolin-4-yloxy]-phenyl}-3-methyl-3H-pyrimidin-4-one Step 1: Preparation of 2-benzyl-3H-pyrimidin-4-one 2-Benzyl-3H-pyrimidin-4-one was prepared as described in WO 94/26715

Step 2: Preparation of 2-benzyl-3-methyl-3H-pyrimidin-4-one $Cs_2CO_3$ (24.6 g, 75.7 mmol) was added to 2-benzyl-3H-pyrimidin-4-one (Step 1, 12.8 g) in DMF (80 mL) and THF (60 mL) at 0° C. After 10 min, MeI (4.3 mL, 68.8 mmol) was added, and the reaction was warmed to RT. After 3 h, the reaction was decanted, diluted with $CH_2Cl_2$, and washed with $H_2O$, and aq. sat. NaCl solution. The organic layer was dried ($Na_2SO_4$) and concentrated under reduced pressure. $Et_2O$ and Hexane (1:1) were added and the solvent was evaporated to provide a brown solid. The solid was triturated with 30' EtOAc/hexane to afford the title compound as a light brown solid. The filtrate was purified by chromatography with 0-5% MeOH/$CHCl_3$ to afford additional compound. MS (ESI pos. ion) m/z: 201.0. (M+H). Calc'd for $C_{12}H_{12}N_2O$: 200.09.

Step 3: Preparation of 2-benzyl-5-bromo-3-methyl-3H-pyrimidin-4-one $Br_2$ (2.62 mL, 52 mmol) was added to 2-benzyl-3-methyl-3H-pyrimidin-4-one (Step 2, 9.3 g, 47 mmol) in $CHCl_3$ (100 mL) and sat $NaHCO_3$ (100 mL). After 30 min, the organic layer was separated, dried ($Na_2SO_4$) and filtered through a plug of silica. The filtrate was concentrated under reduced pressure, and azeotroped with $CHCl_3$ (2×). The crude compound was dried under high vacuum for 16 h to provide the title compound. MS (ESI pos. ion) m/z: 279.0, 281.1. Calc'd for $C_{12}H_{11}BrN_2O$: 278.01.

Step 4: Preparation of 2-benzyl-5-(3-fluoro-4-methoxyphenyl)-3-methyl-3H-pyrimidin-4-one 2-Benzyl-5-bromo-3-methyl-3H-pyrimidin-4-one (Step 3, 11.1 g, 39.9 mmol), 4-methoxy-3-fluorophenylboronic acid (10.12 g, 59 mmol) and $Pd(PPh_3)_4$ (2.3 g, 1.9 mmol) in 2 M $Na_2CO_3$ (100 mL) and dioxane (150 mL) were heated to 90° C. for 1 h. The reaction was cooled to RT, and diluted with $H_2O$ and $CH_2Cl_2$. The organics were separated and washed with brine, dried ($Na_2SO_4$) and filtered through a plug of silica. The filtrate was concentrated under reduced pressure. $Et_2O$/hexane (1:1) were added and the reaction was concentrated under vacuum to a brown solid. The solid was triturated with 20% $Et_2O$/hexane to afford the title compound as a yellow solid. MS (ESI pos. ion) m/z: 325.2. Calc'd for $C_{19}H_{17}FN_2O_2$: 324.13.

Step 5: Preparation of 2-benzyl-5-(3-fluoro-4-hydroxyphenyl)-3-methyl-3H-pyrimidin-4-one HBr (40%, ACS reagent grade) was added to 2-benzyl-5-(3-fluoro-4-methoxyphenyl)-3-methyl-3H-pyrimidin-4-one (Step 4, 9 g, 26 mmol) in HOAc (90 mL). The reaction was heated to 130° C. and monitored by HPLC. After 3 h, the reaction was cooled to RT and the solid was collected by filtration. The solid was washed with $H_2O$ and $Et_2O$ and dried to afford the title compound as a yellow solid. MS (ESI pos. ion) m/z: 311.1. Calc'd for $C_{18}H_{15}FN_2O_2$: 310.11.

Step 6: Preparation of 2-benzyl-5-{3-fluoro-4-[6-methoxy-7-(3-morpholin-4-yl-propoxy)-quinolin-4-yloxy]-phenyl}-3-methyl-3H-pyrimidin-4-one 2-Benzyl-5-(3-fluoro-4-hydroxyphenyl)-3-methyl-3H-pyrimidin-4-one (Step 5, 200 mg, 0.64 mmol), 4-chloro-6-methoxy-7-(3-morpholinopropoxy)quinoline (217 mg, 0.64 mmol) and DMAP (39 mg, 0.32 mmol) in dioxane (3.5 mL) and NMP (1.2 mL) were heated to 90° C. in a CEM microwave (150 W, 10 min, powermax). The dioxane was evaporated and the crude was purified by Prep HPLC (1-95% $CH_3CN/H_2O$ (0.16 TFA)) to afford the TFA salt of the title compound as a yellow glass. MS (ESI pos. ion) m/z: 611.2. Calc'd for $C_{35}H_{35}FN_4O_5$: 610.26.

The following Examples in Table 1 were prepared similar to the procedures described in Example 1.

TABLE 1

| Ex. | Structure and Name | Mol Formula | Mass | MS (MH+) |
|---|---|---|---|---|
| 2 | 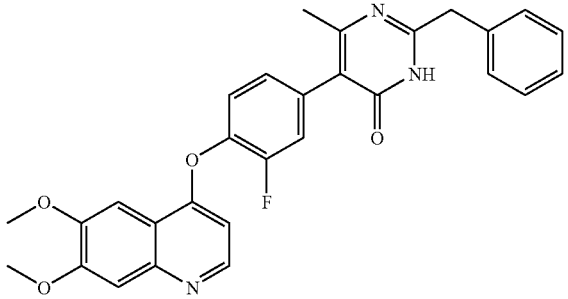<br>5-(4-((6,7-bis(methoxy)-4-quinolinyl)oxy)-3-fluorophenyl)-6-methyl-2-(phenylmethyl)-4(3H)-pyrimidinone | $C_{29}H_{24}FN_3O_4$ | 497.18 | 498.0 |
| 3 | 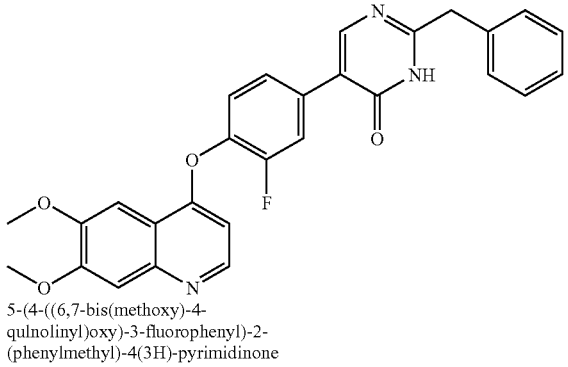<br>5-(4-((6,7-bis(methoxy)-4-quinolinyl)oxy)-3-fluorophenyl)-2-(phenylmethyl)-4(3H)-pyrimidinone | $C_{28}H_{22}FN_3O_4$ | 483.16 | 484.2 |
| 4 | 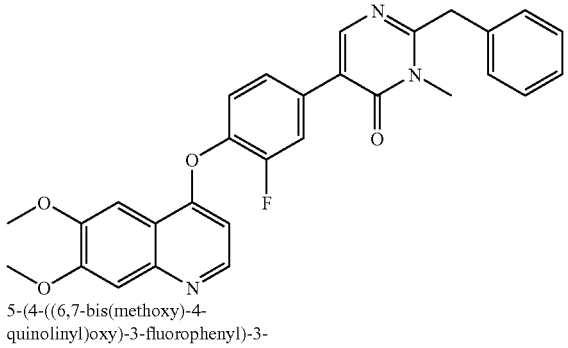<br>5-(4-((6,7-bis(methoxy)-4-quinolinyl)oxy)-3-fluorophenyl)-3-methyl-2-(phenylmethyl)-4(3H)-pyrimidinone | $C_{29}H_{24}FN_3O_4$ | 497.18 | 498.0 |
| 5 | 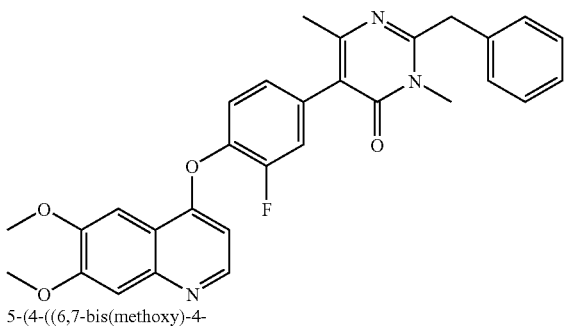<br>5-(4-((6,7-bis(methoxy)-4-quinolinyl)oxy)-3-fluorophenyl)-3,6- | $C_{30}H_{26}FN_3O_4$ | 511.19 | 512.1 |

TABLE 1-continued

| Ex. | Structure and Name | Mol Formula | Mass | MS (MH+) |
|---|---|---|---|---|
| | dimethyl-2-(phenylmethyl)-4(3H)-pyrimidinone | | | |
| 6 | 5-(3-fluoro-4-((6-methoxy-7-(3-(4-morpholinyl)propoxy)-4-quinolinyl)oxy)phenyl)-2-(phenylmethyl)-4(3H)-pyrimidinone | $C_{34}H_{33}FN_4O_5$ | 596.24 | 597.3 |
| 7 | 5-(4-((6,7-bis(methoxy)-4-quinolinyl)oxy)-2-methoxyphenyl)-3-methyl-2-(phenylmethyl)-4(3H)-pyrimidinone | $C_{30}H_{27}N_3O_5$ | 509.20 | 510.0 |
| 8 | 5-(3-fluoro-4-((7-(((2R)-2-hydroxy-3-(4-morpholinyl)-propyl)oxy)-6-methoxy-4-quinolinyl)oxy)phenyl)-3-methyl-2-(phenylmethyl)-4(3H)-pyrimidinone | $C_{35}H_{35}FN_4O_6$ | 626.25 | 627.2 |

TABLE 1-continued

| Ex. | Structure and Name | Mol Formula | Mass | MS (MH+) |
|---|---|---|---|---|
| 9 | 5-(3-fluoro-4-((6-methoxy-7-((3-(1-pyrrolidinyl)propyl)oxy)-4-quinolinyl)oxy)phenyl)-3-methyl-2-(phenylmethyl)-4(3H)-pyrimidinone | $C_{35}H_{35}FN_4O_4$ | 594.26 | 595 |

EXAMPLE 10

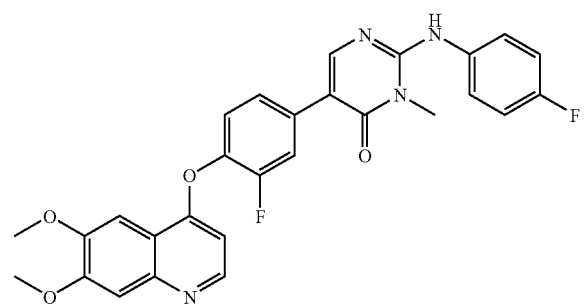

5-[4-(6,7-Dimethoxy-quinolin-4-yloxy)-3-fluoro-phenyl]-2-(4-fluoro-phenylamino)-3-methyl-3H-pyrimidin-4-one

Step 1: Preparation of 2-methylthio-3H-pyrimidin-4-one

This compound was prepared following the procedure of J. Spychala, Syn. Comm., 27(11):1943-1949 (1997).

Step 2: Preparation of 3-methyl-2-methylthio-3H-pyrimidin-4-one

2-Methylthio-3H-pyrimidin-4-one (Step 1, 6.29 g, 44.2 mmol) was suspended in DMF (100 mL), cooled to 0° C., and additional DMF (50 mL) was added. Solid LiHMDS (9.58 g, 57.3 mmol) was added in one portion, and the reaction was stirred at 0° C. MeI (3.6 mL, 57.8 mmol) was added via syringe, and the reaction was warmed to RT and stirred for 20.75 h. At this time, the mixture was poured into 300 mL H$_2$O and extracted exhaustively with EtOAc. The organic extracts were combined, dried over Na$_2$SO$_4$, filtered, concentrated, and purified on silica gel (3:1→3:2→1:1 hexanes/EtOAc) to give the title compound. MS (ESI pos. ion) m/z: 157. Calc'd for $C_6H_8N_2OS$: 156.04.

Step 3: Preparation of 5-bromo-3-methyl-2-methylthio-4(3H)-pyrimidinone

3-Methyl-2-methylthio-3H-pyrimidin-4-one (Step 2, 3.31 g, 21.2 mmol) was dissolved in CHCl$_3$ (50 mL) and cooled to 0° C. under Ar. Br$_2$ (1.25 mL, 25.4 mmol) was added via syringe, and the reaction was stirred at 0° C. for 35 min, at which time TLC analysis indicated complete consumption of starting material. The reaction was quenched with 40 mL saturated NaHCO$_3$, warmed to RT, and stirred overnight. The reaction was extracted with CH$_2$Cl$_2$ (3×25 mL), and the organic extracts were combined, dried over Na$_2$SO$_4$, filtered, and concentrated to give the title compound, which did not require further purification. MS (ESI pos. ion) m/z: 236. Calc'd for $C_6H_7BrN_2OS$: 233.95.

Step 4: Preparation of 5-(3-fluoro-4-methoxyphenyl)-3-methyl-2-methylthio-3H-pyrimidin-4-one 5-Bromo-3-methyl-2-methylthio-4(3H)-pyrimidinone (Step 3, 14.77 g, 62.8 mmol), 3-fluoro-4-methoxyphenylboronic acid (20.11 g, 118.3 mmol), Pd$_2$(dba)$_3$ (1.869 g, 2.04 mmol), S-phos ligand (Strem Chemical, 3.45 g, 8.40 mmol) and K$_3$PO$_4$ (42.27 g, 199.1 mmol) were suspended in toluene (200 mL). Ar was bubbled through the solution for 5 min, and the reaction was placed in an oil bath (100° C.) and stirred for 6.25 h, at which time LCMS analysis indicated a complete reaction. The reaction was cooled to RT and allowed to stand overnight. It was diluted with CH$_2$Cl$_2$ (200 mL) and filtered through a 1-inch plug of silica gel which was washed exhaustively with MeOH, EtOAc, and CH$_2$Cl$_2$. (Some solid material stuck in the flask had to be taken up in water and extracted with EtOAc separately). The filtrate (and EtOAc extracts) were all combined and concentrated, resulting in an orange solid. This was treated with hexanes and filtered, and the resultant light yellow solid was washed repeatedly with hexanes and then put on the high vacuum overnight. The title compound was obtained as a light yellow solid. MS (ESI pos. ion) m/z: 281. Calc'd for $C_{13}H_{13}FN_2O_2S$: 280.07.

Step 5: Preparation of 5-(3-fluoro-4-hydroxyphenyl)-3-methyl-2-methylthio-3H-pyrimidin-4-one 5-(3-Fluoro-4-methoxyphenyl)-3-methyl-2-methylthio-3H-pyrimidin-4-one (Step 4, 10.05 g, 35.85 mmol) was suspended in glacial HOAc (60 mL) and HBr (240 mL, 48%) was added. The reaction was put in an oil bath (110° C.) and stirred for 1.5 h. The reaction was heated to 120° C. and stirred for an additional 1.5 h, and which time LCMS showed very little starting material. The reaction was cooled to 0° C., and EtOAc (300 mL) was added. Saturated NaHCO$_3$ (0.2 L) was added, the reaction was transferred to a 2 L Erlenmeyer flask, and 0.83 L saturated NaHCO$_3$ was added. The reaction was stirred overnight, then more NaHCO$_3$ (300 mL) and 5 N NaOH (100 mL) was added, and the reaction was stirred for 30 min then filtered. The solid was collected while the pH of the filtrate was adjusted to about 5 using 5 N NaOH and filtered again. The solid from both filtrations was combined and dried in vacuo to give title compound. MS (ESI pos. ion) m/z: 267. Calc'd for $C_{12}H_{11}FN_2O_2S$ Mol. Wt.: 266.05.

Step 6: Preparation of 5-(3-fluoro-4-hydroxyphenyl)-2-(4-fluorophenylamino)-3-methyl-3H-pyrimidin-4-one 5-(3-Fluoro-4-hydroxyphenyl)-3-methyl-2-methylthio-3H-pyrimidin-4-one (Step 5, 0.39 g, 1.5 mmol) was suspended in 3.6 mL p-fluoroaniline and concentrated HCl (1 drop) was added. The reaction was heated in a microwave at 120° C. and 100 W for 10 min (using a Powermax feature on a CEM microwave). The reaction was cooled to RT and diluted with EtOAc (100 mL). The organic phase was extracted with 1 N NaOH (3×15 mL), and the aqueous extracts were neutralized with concentrated HCl. The aqueous layer was extracted with EtOAc (3×20 mL), and the organic extracts were combined, dried over Na$_2$SO$_4$, filtered, and concentrated to give desired compound. MS (ESI pos. ion) m/z: 330. Calc'd for $C_{17}H_{13}F_2N_3O_2$: 329.10.

Step 7: Preparation of 5-(4-(6,7-dimethoxyquinolin-4-yloxy)-3-fluorophenyl)-2-(4-fluorophenylamino)-3-methyl-3H-pyrimidin-4-one 5-(3-Fluoro-4-hydroxyphenyl)-2-(4-fluorophenylamino)-3-methyl-3H-pyrimidin-4-one (Step 6, 296.7 mg, 0.901 mmol), 3,4-dimethocyquinoline chloride (313.9 mg, 1.404 mmol), and DMAP (28 mg, 0.23 mmol) were suspended in 1,4-dioxane (3.0 ml) and heated in a microwave at 120° C. and 300 W for 20 min. The reaction was cooled to RT and concentrated. The mixture was purified first using reverse-phase HPLC (10%→95% CH$_3$CN/H$_2$O with 0.1% TFA) and then by filtering 2× through a 0.5 inch-1 inch plug of silica gel with EtOAc. Fractions with pure compound collected and concentrated to give the title compound. MS (ESI pos. ion) m/z: 517. Calc'd for $C_{28}H_{22}F_2N_4O_4$: 516.16.

EXAMPLE 11

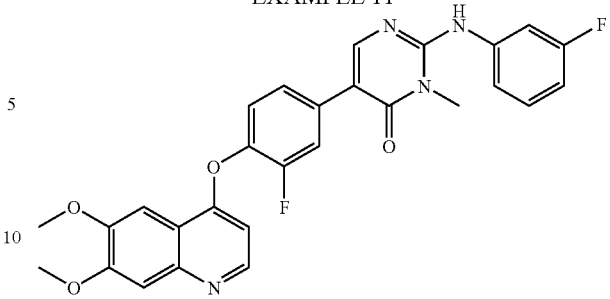

5-[4-(6,7-Dimethoxy-quinolin-4-yloxy)-3-fluorophenyl]-2-(3-fluoro-phenylamino)-3-methyl-3H-pyrimidin-4-one Step 1: Preparation of 5-(4-(6,7-dimethoxyquinolin-4-yloxy)-3-fluorophenyl)-3-methyl-2-methylthio-3H-pyrimidin-4-one 5-(3-Fluoro-4-hydroxyphenyl)-3-methyl-2-methylthio-4(3H)-pyrimidinone (Ex. 12, 522.7 mg, 1.963 mmol), 3,4-dimethocyquinoline chloride (591 mg, 2.64 mmol), and DMAP (72 mg, 0.589 mmol) were suspended in 4.0 mL 1,4-dioxane and heated in a microwave at 300 W and 120° C. for 20 min. This process was repeated 3× using 528 mg, 528 mg, and 536 mg of the starting material. All four reactions were combined, concentrated, and filtered through a plug of silica gel (3:1 EtOAc/hexanes) to give the title compound. MS (ESI pos. ion) m/z: 454. Calc'd for $C_{23}H_{20}FN_3O_4S$: 453.12.

Step 2: Preparation of 5-(4-(6,7-dimethoxyquinolin-4-yloxy)-3-fluorophenyl)-2-hydroxy-3-methyl-3H-pyrimidin-4-one 5-(4-(6,7-Dimethoxyquinolin-4-yloxy)-3-fluorophenyl)-3-methyl-2-methylthio-3H-pyrimidin-4-one (Step 1, 1.048 g, 2.3 mmol) was dissolved in CH$_3$CN (15 mL) and TFA (1.7 mL) and cooled to 0° C. Urea hydrogen peroxide (290 mg, 3.09 mmol) was added, and the reaction was stirred for 5 min. trifluoroacetic anhydride (0.43 mL, 3.09 mmol) was added, and the reaction was warmed to RT and stirred for 40 min. The mixture was quenched with H$_2$O (10 mL) and EtOAc (25 mL) and allowed to stand overnight. Saturated NaHCO$_3$ (10 mL) and EtOAc were added, and the layers were separated. The aqueous layer was extracted with EtOAc, and the organic layers were combined, dried over Na$_2$SO$_4$, filtered, concentrated, and purified on silica gel (EtOAc→1:1 EtOAc/MeOH) to give title compound. MS (ESI pos. ion) m/z: 411. Calc'd for $C_{21}H_{17}FN_3O_5$: 410.39.

Step 3: Preparation of 2-chloro-5-(4-(6,7-dimethoxyquinolin-4-yloxy)-3-fluorophenyl)-3-methylpyrimidin-4(3H)-one 5-(4-(6,7-Dimethoxyquinolin-4-yloxy)-3-fluorophenyl)-2-hydroxy-3-methyl-3H-pyrimidin-4-one (Step 2, 678.8 mg, 1.605 mmol) was dissolved in POCl$_3$ (16 mL) and N,N-dimethylaniline (1.6 ml) and heated at 125° C. for 8.5 h then cooled to RT and stirred overnight. The reaction was concentrated, diluted with CH$_2$Cl$_2$ (125 mL) and washed with saturated NaHCO$_3$ (25 mL, 17 mL). The organic layer was dried over Na$_2$SO$_4$, filtered, and concentrated. Because of the propensity of title compound to hydrolysis, the crude chloride was used for the next reaction.

Step 4: Preparation of 5-(4-(6,7-dimethoxyquinolin-4-yloxy)-3-fluorophenyl)-2-(3-fluorophenylamino)-3-methyl-3H-pyrimidin-4-one The crude 2-chloro-5-(4-(6,7-dimethoxyquinolin-4-yloxy)-3-fluorophenyl)-3-methylpyrimidin-4(3H)-one from Step 3 was dissolved in 15 mL 1,4-dioxane. To 5 mL of this solution was added m-fluoroaniline (0.2 mL) and concentrated HCl (1 drop). The reaction was heated in the microwave at 60° C. and 60 W for 5 min before being cooled to RT. The mixture was concentrated and filtered through a 1 inch plug of silica gel with EtOAc→2:1 EtOAc/MeOH→3:2 MeOH/EtOAc. The filtrate was concentrated and purified using reverse phase HPLC (10%→95% MeCN/H$_2$O with 0.1% TFA). Finally, the compound was filtered again through a 1-inch plug of silica gel in a pipette column with EtOAc to give the title compound. MS (ESI pos. ion) m/z: 517. Calc'd for C$_{28}$H$_{22}$F$_2$N$_4$O$_4$: 516.16.

The following Examples in Table 2 were prepared similar to the procedures described in either Example 10 or Example 11.

TABLE 2

| Ex. | Structure | Mol Formula | Mol Weight | MS (MH+) |
|---|---|---|---|---|
| 12 | 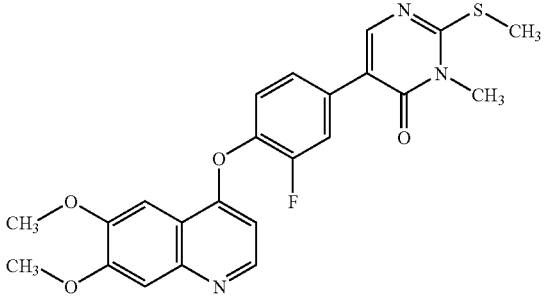<br>5-(4-((6,7-bis(methoxy)-4-quinolinyl)oxy)-3-fluorophenyl)-3-methyl-2-methylthio-4(3H)-pyrimidinone | C$_{23}$H$_{20}$FN$_3$O$_4$S | 453.12 | 454.0 |
| 13 | 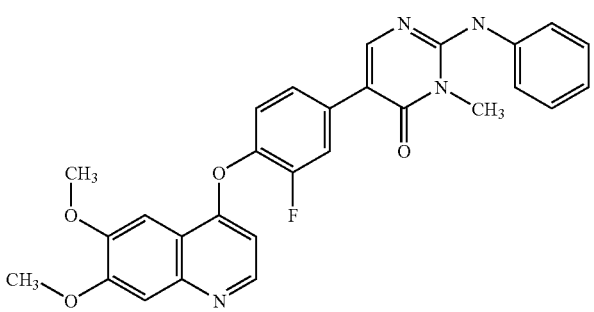<br>5-(4-((6,7-bis(methoxy)-4-quinolinyl)oxy)-3-fluorophenyl)-3-methyl-2-(phenylamino)-4(3H)-pyrimidinone | C$_{28}$H$_{23}$FN$_4$O$_4$ | 498.17 | 499.0 |
| 14 | 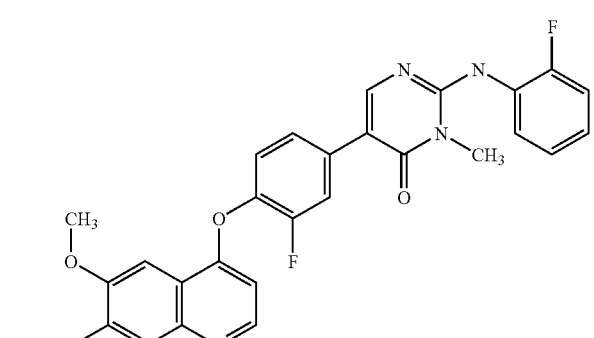<br>5-(4-((6,7-bis(methoxy)-4-quinolinyl)oxy)-3-fluorophenyl)-2-((2-fluorophenyl)amino)-3-methyl-4(3H)-pyrimidinone | C$_{28}$H$_{22}$F$_2$N$_4$O$_4$ | 516.16 | 517.0 |

TABLE 2-continued

| Ex. | Structure | Mol Formula | Mol Weight | MS (MH+) |
|---|---|---|---|---|
| 15 | 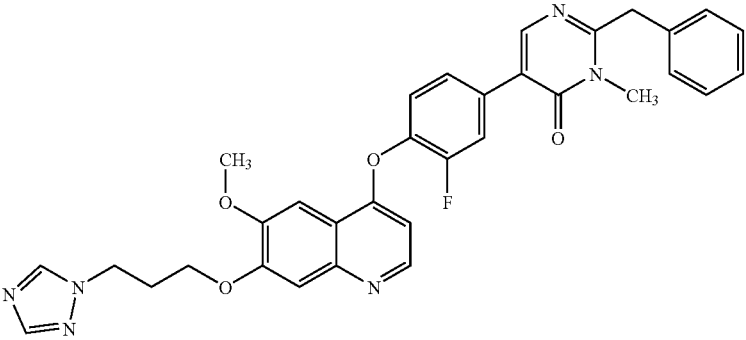 5-(3-fluoro-4-((6-methoxy-7-(3-(1H-1,2,4-triazol-1-yl)propoxy)-4-quinolinyl)oxy)phenyl)-3-methyl-2-(phenylmethyl)-4(3H)-pyrimidinone | $C_{33}H_{29}FN_6O_4$ | 592.22 | |
| 16 | 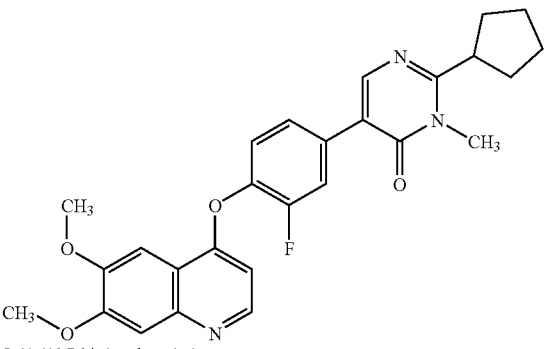 5-(4-((6,7-bis(methoxy)-4-quinolinyl)oxy)-3-fluorophenyl)-2-cyclopentyl-3-methyl-4(3H)-pyrimidinone | $C_{27}H_{26}FN_3O_4$ | 475.19 | |
| 17 | 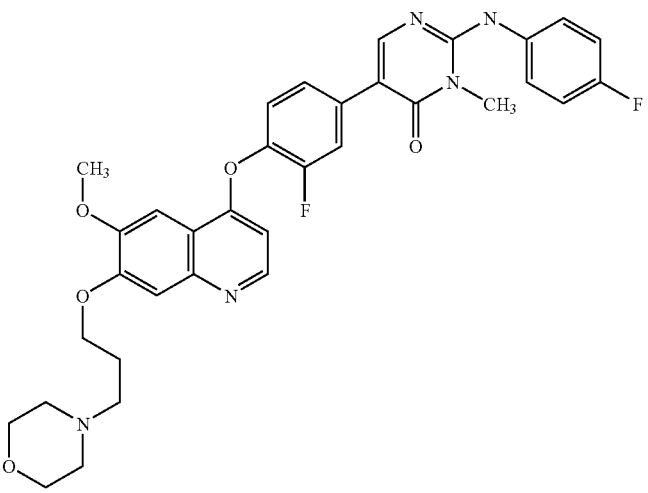 5-(3-fluoro-4-((6-methoxy-7-(3-(4-morpholinyl)propoxy)-4-quinolinyl)oxy)phenyl)-2-((4-fluorophenyl)amino)-3-methyl-4(3H)-pyrimidinone | $C_{34}H_{33}F_2N_5O_5$ | 629.24 | 630.2 |

TABLE 2-continued

| Ex. | Structure | Mol Formula | Mol Weight | MS (MH+) |
| --- | --- | --- | --- | --- |
| 18 | 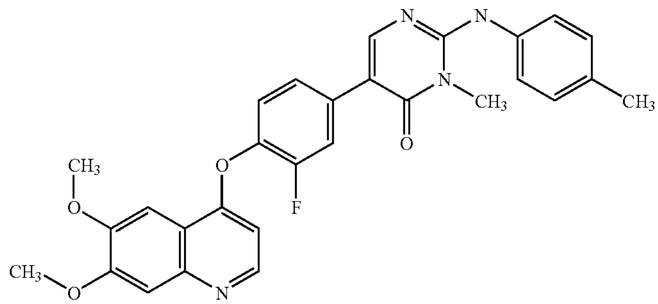 | $C_{29}H_{25}FN_4O_4$ | 512.19 | 513.0 |

5-(4-((6,7-bis(methoxy)-4-quinolinyl)oxy)-3-fluorophenyl)-3-methyl-2-((4-methylphenyl)amino)-4(3H)-pyrimidinone

| 19 | | $C_{29}H_{22}F_4N_4O_4$ | 566.16 | 567.1 |

5-(4-((6,7-bis(methoxy)-4-quinolinyl)oxy)-3-fluorophenyl)-3-methyl-2-((4-(trifluoromethyl)phenyl)amino)-4(3H)-pyrimidinone

| 20 | | $C_{36}H_{39}FN_6O_5$ | 654.30 | 655 |

2-((4-(dimethylamino)phenyl)amino)-5-(3-fluoro-4-((6-methoxy-7-((3-(4-morpholinyl)propyl)oxy)-4-quinolinyl)oxy)phenyl)-3-methyl-4(3H)-pyrimidinone TABLE 2-continued

| Ex. | Structure | Mol Formula | Mol Weight | MS (MH+) |
|---|---|---|---|---|
| 21 | 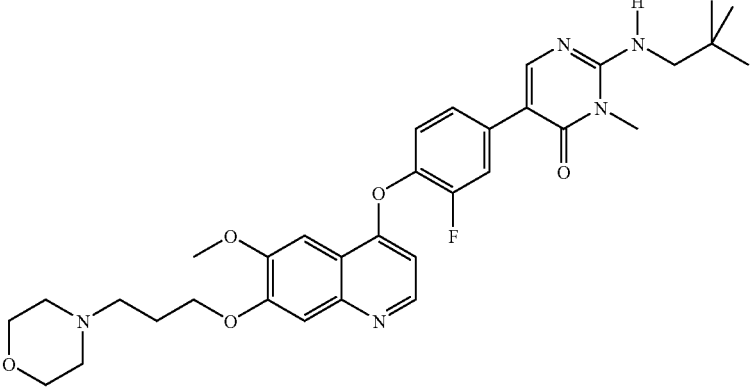<br>2-((2,2-dimethylpropyl)amino)-5-(3-fluoro-4-((6-methoxy-7-(3-(4-morpholinyl)propoxy)-4-quinolinyl)oxy)phenyl)-3-methyl-4(3H)-pyrimidinone | $C_{33}H_{40}FN_5O_5$ | 605.30 | 606 |
| 22 | 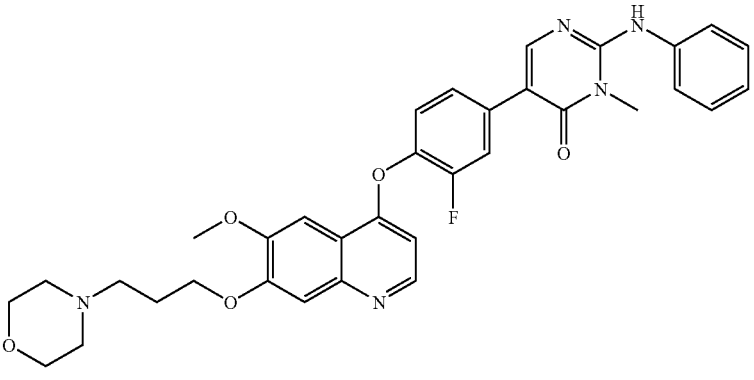<br>5-(3-fluoro-4-((6-methoxy-7-((3-(4-morpholinyl)propyl)oxy)-4-quinolinyl)oxy)phenyl)-3-methyl-2-(phenylamino)-4(3H)-pyrimidinone | $C_{34}H_{34}FN_5O_5$ | 611.25 | 612 |
| 23 | 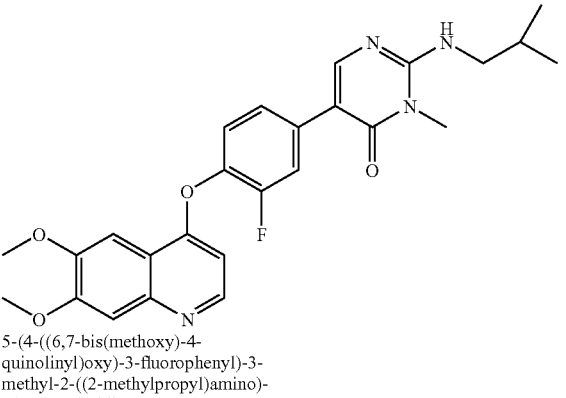<br>5-(4-((6,7-bis(methoxy)-4-quinolinyl)oxy)-3-fluorophenyl)-3-methyl-2-((2-methylpropyl)amino)-4(3H)-pyrimidinone | $C_{26}H_{27}FN_4O_4$ | 478.20 | 479 |

TABLE 2-continued
| Ex. | Structure | Mol Formula | Mol Weight | MS (MH+) |
|---|---|---|---|---|
| 24 | 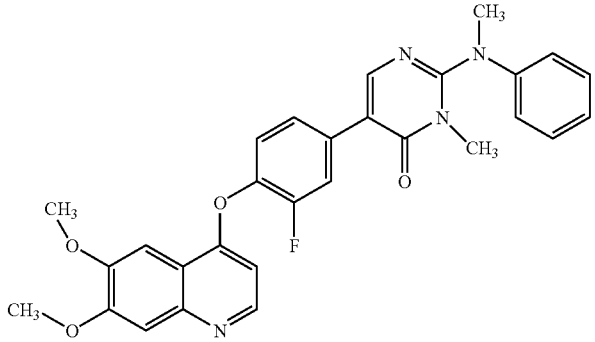 5-(4-(6,7-bis(methoxy)-4-quinolinyloxy)-3-fluorophenyl)-3-methyl-2-(methyl(phenyl)amino)-4(3H)-pyrimidinone | $C_{29}H_{25}FN_4O_4$ | 512.19 | 513 |
| 25 | 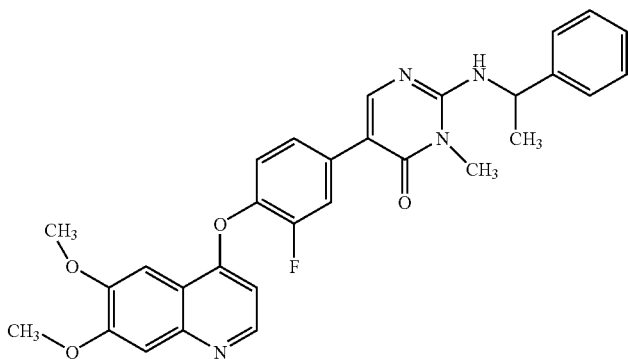 5-(4-(6,7-bis(methoxy)-4-quinolinyloxy)-3-fluorophenyl)-3-methyl-2-((1-phenylethyl)amino)-4(3H)-pyrimidinone | $C_{30}H_{27}FN_4O_4$ | 526.20 | 527 |
| 26 | 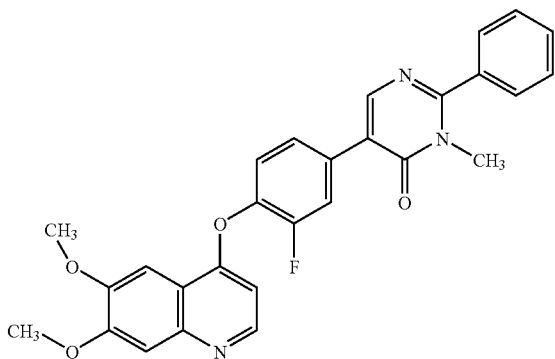 5-(4-(6,7-bis(methoxy)-4-quinolinyloxy)-3-fluorophenyl)-3-methyl-2-phenyl-4(3H)-pyrimidinone | $C_{28}H_{22}FN_3O_4$ | 483.16 | 484 |

TABLE 2-continued

| Ex. | Structure | Mol Formula | Mol Weight | MS (MH+) |
| --- | --- | --- | --- | --- |
| 27 | 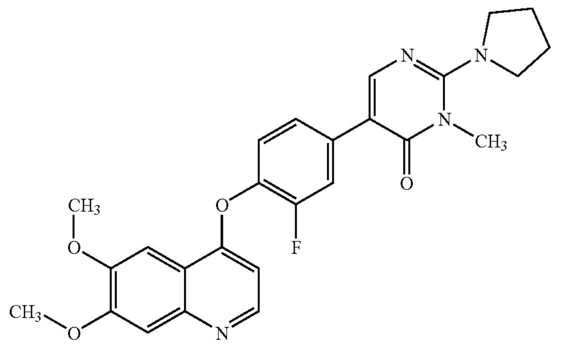 | $C_{26}H_{25}FN_4O_4$ | 476.19 | 477 |

5-(4-((6,7-bis(methoxy)-4-quinolinyl)oxy)-3-fluorophenyl)-3-methyl-2-(1-pyrrolidinyl)-4(3H)-pyrimidinone

| 28 | | $C_{36}H_{38}FN_5O_4$ | 623.29 | 624 |

5-(3-fluoro-4-((6-methoxy-7-(3-(4-methyl-1-piperazinyl)propoxy)-4-quinolinyl)oxy)phenyl)-3-methyl-2-(phenylmethyl)-4(3H)-pyrimidinone

| 29 | | $C_{33}H_{33}FN_4O_4$ | 568.25 | 569 |

5-(4-((6,7-bis(methoxy)-4-quinolinyl)oxy)-3-fluorophenyl)-3-methyl-2-((3-methylbutyl)(phenyl)amino)-4(3H)-pyrimidinone TABLE 2-continued

| Ex. | Structure | Mol Formula | Mol Weight | MS (MH+) |
|---|---|---|---|---|
| 30 | 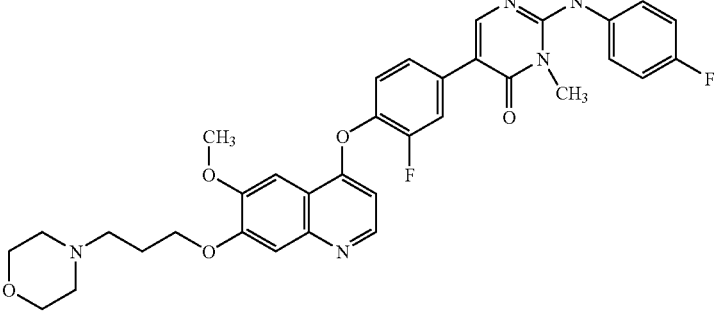 5-(3-fluoro-4-(6-methoxy-7-((3-(4-morpholinyl)propoxy)-4-quinolinyl)oxy)phenyl)-2-((4-fluorophenyl)methyl)-3-methyl-4(3H)-pyrimidinone | $C_{35}H_{34}F_2N_4O_5$ | 628.25 | 629 |
| 31 | 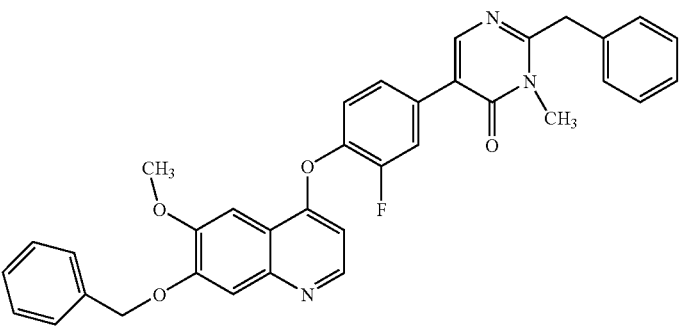 5-(3-fluoro-4-((6-methoxy-7-((phenylmethoxy)-4-quinolinyl)-oxy)phenyl)-3-methyl-2-(phenylmethyl)-4(3H)-pyrimidinone | $C_{35}H_{28}FN_3O_4$ | 573.21 | 574 |
| 32 | 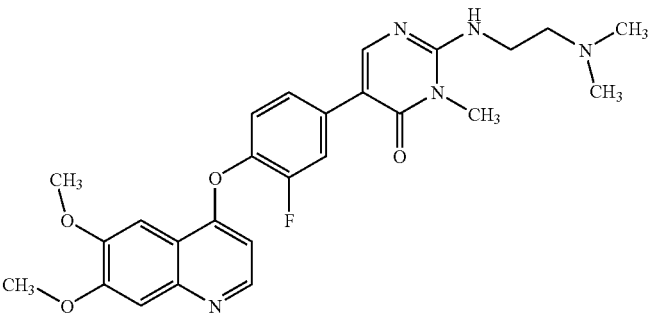 5-(4-((6,7-bis(methoxy)-4-quinolinyl)oxy)-3-fluorophenyl)-2-((2-(dimethylamino)ethyl)amino)-3-methyl-4(3H)-pyrimidinone | $C_{26}H_{28}FN_5O_4$ | 493.21 | 494 |

TABLE 2-continued

| Ex. | Structure | Mol Formula | Mol Weight | MS (MH+) |
|---|---|---|---|---|
| 33 | 5-(4-((6,7-bis(methoxy)-4-quinolinyl)oxy)-3-fluorophenyl)-2-((cyclopropylmethyl)amino)-3-methyl-4(3H)-pyrimidinone | C₂₆H₂₅FN₄O₄ | 476.19 | 477 |
| 34 | 5-(4-((6,7-bis(methoxy)-4-quinolinyl)oxy)-3-fluorophenyl)-3-methyl-2-((phenylmethyl)amino)-4(3H)-pyrimidinone | C₂₉H₂₅FN₄O₄ | 512.19 | 513 |
| 35 | 5-(4-((7-(3-(4-ethyl-1-piperazinyl)propoxy)-6-methoxy-4-quinolinyl)oxy)-3-fluorophenyl)-3-methyl-2-(phenylmethyl)-4(3H)-pyrimidinone | C₃₇H₄₀FN₅O₄ | 637.31 | 638 |

TABLE 2-continued

| Ex. | Structure | Mol Formula | Mol Weight | MS (MH+) |
|---|---|---|---|---|
| 36 | 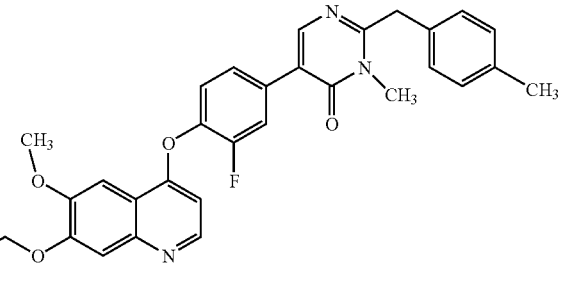 5-(3-fluoro-4-((6-methoxy-7-(3-(4-morpholinyl)propoxy)-4-quinolinyl)oxy)phenyl)-3-methyl-2-((4-methylphenyl)methyl)-4(3H)-pyrimidinone | $C_{36}H_{37}FN_4O_5$ | 624.27 | 625 |
| 37 | 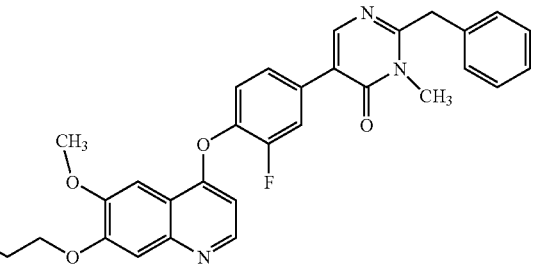 5-(3-fluoro-4-((7-((3-(4-hydroxy-1-piperidinyl)propyl)oxy)-6-methoxy-4-quinolinyl)oxy)phenyl)-3-methyl-2-(phenylmethyl)-4(3H)-pyrimidinone | $C_{36}H_{37}FN_4O_5$ | 624.27 | 625 |

The following Examples in Table 3 were prepared similar to the procedures described in the above Examples.

TABLE 3

| Ex. | Structure | Mol Formula | Mol Weight | MS (MH+) |
|---|---|---|---|---|
| 37a | 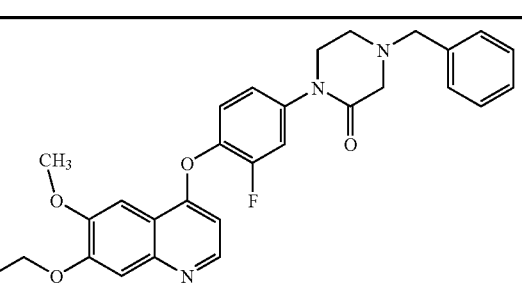 4-Benzyl-1-{3-fluoro-4-[6-methoxy-7-(3-morpholin-4-yl-propoxy)-quinolin-4-yloxy]-phenyl}-piperazin-2-one | $C_{34}H_{37}FN_4O_5$ | 600.27 | 601 |

TABLE 3-continued

| Ex. | Structure | Mol Formula | Mol Weight | MS (MH+) |
|---|---|---|---|---|
| 37b | 1-Benzyl-4-{3-fluoro-4-[6-methoxy-7-(3-morpholin-4-yl-propoxy)-quinolin-4-yloxy]-phenyl}-piperazine-2,5-dione | C₃₄H₃₅FN₄O₆ | 614.25 | 615 |
| 37c | 1-Benzyl-4-[4-(7-benzyloxy-6-methoxy-quinolin-4-yloxy)-3-fluoro-phenyl]-piperazine-2,5-dione | C₃₄H₂₈FN₃O₅ | 577.20 | 578 |
| 37d | 5-[4-(6,7-Dimethoxy-quinolin-4-yloxy)-3-fluoro-phenyl]-3-methyl-2-(pyridin-2-ylamino)-3H-pyrimidin-4-one | C₂₇H₂₂FN₅O₄ | 499.17 | 500 |

TABLE 3-continued

| Ex. | Structure | Mol Formula | Mol Weight | MS (MH+) |
|---|---|---|---|---|
| 37e | 5-[4-(6,7-Dimethoxy-quinolin-4-yloxy)-3-fluoro-phenyl]-2-(2-dipropylamino-cyclohexylamino)-3-methyl-3H-pyrimidin-4-one | $C_{34}H_{42}FN_5O_4$ | 603.32 | 604 |
| 37f | 2-(Amino-phenyl-methyl)-5-(4-(6,7-dimethoxy-quinolin-4-yloxy)-3-fluoro-phenyl]-3-methyl-3H-pyrimidin-4-one | $C_{29}H_{25}FN_4O_4$ | 512.19 | 513 |
| 37g | 5-{3-Fluoro-4-[6-methoxy-7-(3-morpholin-4-yl-propoxy)-quinolin-4-yloxy]-phenyl}-2-phenylamino-3H-pyrimidine-4-thione | $C_{33}H_{32}FN_5O_4S$ | 613.22 | 614 |

TABLE 3-continued

| Ex. | Structure | Mol Formula | Mol Weight | MS (MH+) |
|---|---|---|---|---|
| 37h | 5-[4-(6,7-Dimethoxy-quinolin-4-yloxy)-3-fluoro-phenyl]-3-methyl-2-[1-(2,2,2-trifluoro-acetyl)-piperidin-3-ylamino]-3H-pyrimidin-4-one | $C_{29}H_{27}F_4N_5O_5$ | 601.19 | 602 |
| 37i | 5-[4-(6,7-Dimethoxy-quinolin-4-yloxy)-3-fluoro-phenyl]-3-methyl-2-(1-propyl-piperidin-3-ylamino)-3H-pyrimidin-4-one | $C_{30}H_{34}FN_5O_4$ | 547.26 | 548 |
| 37j | 2-(1-Acetyl-piperidin-3-ylamino)-5-[4-(6,7-dimethoxy-quinolin-4-yloxy)-3-fluoro-phenyl]-3-methyl-3H-pyrimidin-4-one | $C_{29}H_{30}FN_5O_5$ | 547.22 | 548 |
| 37k | 5-(4-((6,7-bis(methoxy)-4-quinolinyl)oxy)-3-fluorophenyl)-3-methyl-2-((2-piperidinylmethyl)amino)-4(3H)-pyrimidinone | $C_{28}H_{30}FN_5O_4$ | 519.23 | 520 |

TABLE 3-continued

| Ex. | Structure | Mol Formula | Mol Weight | MS (MH+) |
|---|---|---|---|---|
| 37l | 5-(4-((6,7-bis(methoxy)-4-quinolinyl)oxy)-3-fluorophenyl)-3-methyl-2-(3-piperidinylamino)-4(3H)-pyrimidinone | C<sub>27</sub>H<sub>28</sub>FN<sub>5</sub>O<sub>4</sub> | 505.21 | 506 |
| 37m | 2-(4-acetyl-1-piperazinyl)-5-(4-((6,7-bis(methoxy)-4-quinolinyl)oxy)-3-fluorophenyl)-3-methyl-4(3H)-pyrimidinone | C<sub>28</sub>H<sub>28</sub>FN<sub>5</sub>O<sub>5</sub> | 533.21 | 534 |
| 37n | 5-(4-((6,7-bis(methoxy)-4-quinolinyl)oxy)-3-fluorophenyl)-2-hydroxy-3-methyl-4(3H)-pyrimidinone | C<sub>22</sub>H<sub>18</sub>FN<sub>3</sub>O<sub>5</sub> | 423.12 | 424 |
| 37o | 3-(4-((6,7-bis(methoxy)-4-quinolinyl)oxy)-3-fluorophenyl)-1-methyl-6-(3-pyridinylamino)-2(1H)-pyridinone | C<sub>28</sub>H<sub>23</sub>FN<sub>4</sub>O<sub>4</sub> | 498.17 | 499 |

TABLE 3-continued
| Ex. | Structure | Mol Formula | Mol Weight | MS (MH+) |
|---|---|---|---|---|
| 37p | 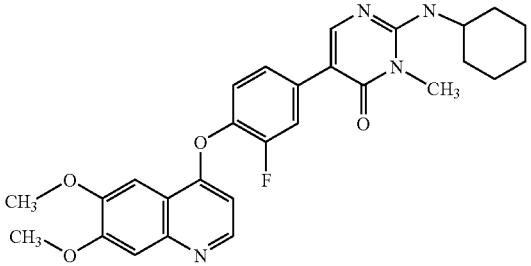 5-(4-((6,7-bis(methoxy)-4-quinolinyl)-oxy)-3-fluorophenyl)-2-(cyclohexylamino)-3-methyl-4(3H)-pyrimidinone | $C_{28}H_{29}FN_4O_4$ | 504.22 | 505 |
| 37q | 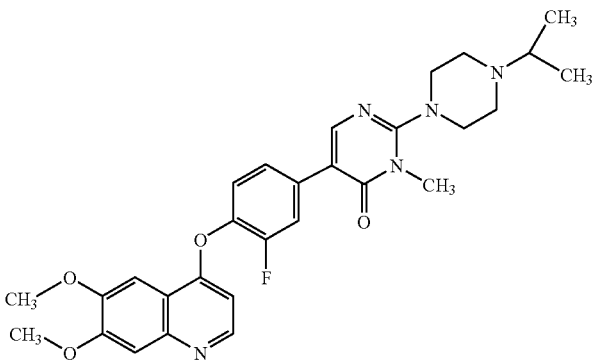 5-(4-((6,7-bis(methoxy)-4-quinolinyl)oxy)-3-fluorophenyl)-3-methyl-2-(4-(1-methylethyl)-1-piperazinyl)-4(3H)-pyrimidinone | $C_{29}H_{32}FN_5O_4$ | 533.24 | 534 |
| 37r | 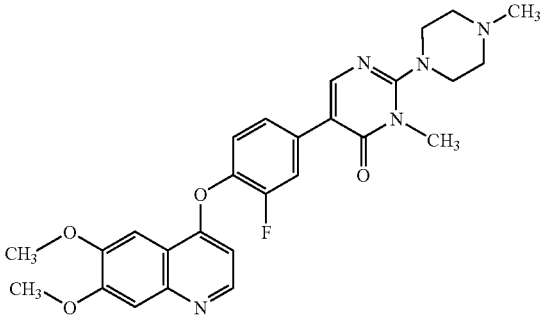 5-(4-((6,7-bis(methoxy)-4-quinolinyl)oxy)-3-fluorophenyl)-3-methyl-2-(4-methyl-1-piperazinyl)-4(3H)-pyrimidinone | $C_{27}H_{28}FN_5O_4$ | 505.21 | 506 |

TABLE 3-continued

| Ex. | Structure | Mol Formula | Mol Weight | MS (MH+) |
|---|---|---|---|---|
| 37s | 5-(3-fluoro-4-((6-methoxy-7-((3-(4-morpholinyl)-propyl)oxy)-4-quinolinyl)oxy)phenyl)-2-(hydroxy(phenyl)methyl)-3-methyl-4(3H)-pyrimidinone | $C_{35}H_{35}FN_4O_6$ | 626.25 | 627 |
| 37t | 5-(4-((6,7-bis(methoxy)-4-quinolinyl)-oxy)-3-fluorophenyl)-2-((4-fluoro-2-methylphenyl)amino)-4(3H)-pyrimidinone | $C_{28}H_{22}F_2N_4O_4$ | 516.16 | 517 |
| 37u | 5-(4-((6,7-bis(methoxy)-4-quinolinyl)-oxy)-3-fluorophenyl)-2-((4-fluoro-2-methylphenyl)amino)-3-methyl-4(3H)-pyrimidinone | $C_{29}H_{24}F_2N_4O_4$ | 530.18 | 531 |

TABLE 3-continued
| Ex. | Structure | Mol Formula | Mol Weight | MS (MH+) |
|---|---|---|---|---|
| 37v | 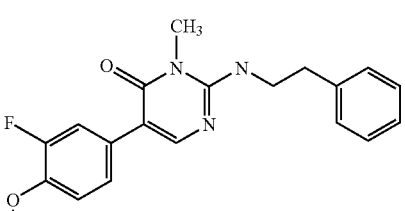<br>5-(4-((6,7-bis(methoxy)-4-quinolinyl)-oxy)-3-fluorophenyl)-3-methyl-2-((2-phenylethyl)amino)-4(3H)-pyrimidinone | $C_{30}H_{27}FN_4O_4$ | 526.20 | 527 |
| 37w | 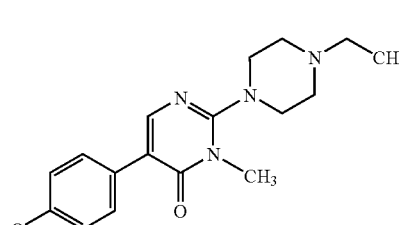<br>5-(4-((6,7-bis(methoxy)-4-quinolinyl)-oxy)-3-fluorophenyl)-2-(4-ethyl-1-piperazinyl)-3-methyl-4(3H)-pyrimidinone | $C_{28}H_{30}FN_5O_4$ | 519.23 | 520 |
| 37x | 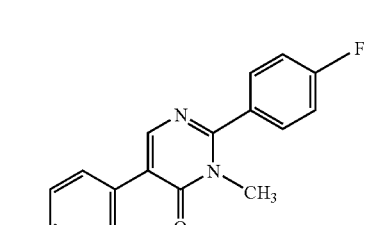<br>5-(4-((6,7-bis(methoxy)-4-quinolinyl)-oxy)-3-fluorophenyl)-2-(4-fluorophenyl)-3-methyl-4(3H)-pyrimidinone | $C_{28}H_{21}F_2N_3O_4$ | 501.15 | 502 |

TABLE 3-continued

| Ex. | Structure | Mol Formula | Mol Weight | MS (MH+) |
|---|---|---|---|---|
| 37y | 5-(3-fluoro-4-((6-methoxy-7-((3-(4-morpholinyl)propyl)oxy)-4-quinolinyl)-oxy)phenyl)-2-(phenylamino)-4(3H)-pyrimidinone | $C_{33}H_{32}FN_5O_5$ | 597.24 | 598 |
| 37z | 5-(4-((6,7-bis(methoxy)-4-quinolinyl)oxy)-3-fluorophenyl)-3-methyl-2-((1R)-1-phenylethyl)-4(3H)-pyrimidinone | $C_{30}H_{26}FN_3O_4$ | 511.19 | 512 |
| 37aa | 5-(4-((6,7-bis(methoxy)-4-quinolinyl)oxy)-3-fluorophenyl)-3-methyl-4(3H)-pyrimidinone | $C_{22}H_{18}FN_3O_4$ | 407.13 | 408 |
| 37ab | 5-(4-((6,7-bis(methoxy)-4-quinolinyl)oxy)-3-fluorophenyl)-2-(phenylamino)-4(3H)-pyrimidinone | $C_{27}H_{21}FN_4O_4$ | 484.15 | 485 |

TABLE 3-continued

| Ex. | Structure | Mol Formula | Mol Weight | MS (MH+) |
|---|---|---|---|---|
| 37ac | 5-(3-fluoro-4-((6-methoxy-7-((3-(4-morpholinyl)propyl)oxy)-4-quinolinyl)oxy)phenyl)-3-methyl-2-((4-methoxy-phenyl)amino)-4(3H)-pyrimidinone | $C_{35}H_{36}FN_5O_6$ | 641.26 | 642 |
| 37ad | 5-(3-fluoro-4-((6-methoxy-7-((3-(4-morpholinyl)propyl)oxy)-4-quinolinyl)oxy)phenyl)-3-methyl-2-((4-methylphenyl)amino)-4(3H)-pyrimidinone | $C_{35}N_{36}FN_5O_5$ | 625.27 | 626 |
| 37ae | 2-((4-chlorophenyl)amino)-5-(3-fluoro-4-((6-methoxy-7-((3-(4-morpholinyl)propyl)oxy)-4-quinolinyl)oxy)phenyl)-3-methyl-4(3H)-pyrimidinone | $C_{34}H_{33}ClFN_5O_5$ | 645.22 | 646 |

TABLE 3-continued

| Ex. | Structure | Mol Formula | Mol Weight | MS (MH+) |
|---|---|---|---|---|
| 37af | 5-(3-fluoro-4-((7-hydroxy-6-methoxy-4-quinolinyl)oxy)phenyl)-3-methyl-2-(phenylmethyl)-4(3H)-pyrimidinone | $C_{28}H_{22}FN_3O_4$ | 483.16 | 484 |
| 37ag | 5-(3-fluoro-4-((6-methoxy-7-((3-(4-morpholinyl)propyl)oxy)-4-quinolinyl)oxy)phenyl)-3-methyl-2-(phenylcarbonyl)-4(3H)-pyrimidinone | $C_{35}H_{33}FN_4O_6$ | 624.24 | 625 |
| 37ah | 5-(4-((6,7-bis(methoxy)-4-quinolinyl)oxy)-3-fluorophenyl)-3-methyl-2-(phenylmethyl)-4(3H)-pyrimidinone | $C_{29}H_{24}FN_4O_3$ | 497.18 | 498 |

EXAMPLE 38

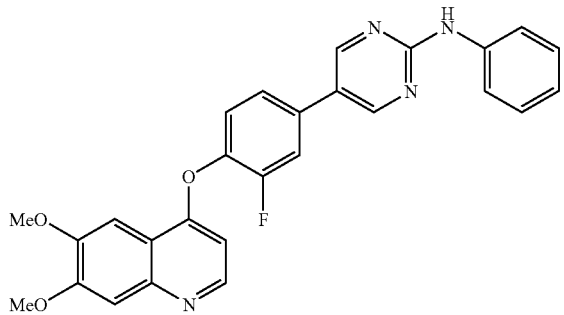

5-(4-(6,7-Dimethoxyquinolin-4-yloxy)-3-fluorophenyl)-N-phenylpyrimidin-2-amine

Step 1: Preparation of 5-(3-fluoro-4-methoxyphenyl)pyrimidin-2-amine

In a 500 mL round bottom flask under $N_2$, 3-fluoro-4-methoxyphenylboronic acid (5.0 g, 29.4 mmol) and 5-iodopyrimidin-2-amine (5.5 g, 24.9 mmol) were mixed. Toluene (100 mL), EtOH (40 mL) and $H_2O$ (20 mL) were added, followed by the addition of $Na_2CO_3$ (3.0 g, 24.2 mmol). A stream of $N_2$ was bubbled through the mixture for 5 min before the catalyst $Pd(PPh)_4$ (0.30 g, 0.26 mmol) was added. The mixture was heated at 80° C. under $N_2$ for 20 h whereby it was cooled to RT. A solution of NaOH (5 N, 10 mL) was added to the mixture and stirring was continued for 10 min. The mixture was filtered and the solid was washed with $H_2O$ (3×10 mL), followed by a mixture of hexanes—EtOAc (1:1, 30 mL). The solid was dried in the air to give the title compound. MS (ESI pos. ion) m/z: 220. Calc'd for $C_{11}H_{10}FN_3O$: 219.08.

Step 2: Preparation of 5-(3-fluoro-4-methoxyphenyl)-N-phenylpyrimidin-2-amine A mixture of 5-(3-fluoro-4-methoxyphenyl)pyrimidin-2-amine (Step 1, 0.44 g, 2.0 mmol) and bromobenzene (0.60 g, 4.0 mmol) in N,N'-dimethylacetamide (1.0 mL) and toluene (1.0 mL) was placed in a microwave tube and was treated with $Pd(OAc)_2$ (0.024 g, 0.1 mmol), 2-biscyclohexyl 1,1-biphenyl phosphine (Strem Chemical, 0.070 g, 0.20 mmol), and $KO^tBu$ (0.44 g, 4.0 mmol). The mixture was degassed with $N_2$ (2×) and was subject to microwave heating at 200° C. for a total of 20 min. After the mixture was cooled to RT, it was filtered through a pad of Celite®. The solid was washed with EtOAc (3×10 mL), and the combined organic phase was washed with $H_2O$, $NH_4Cl$ (sat.), dried with $Na_2SO_4$, and concentrated to an oil. Purification on silica using hexanes-EtOAc (3:1) resulted the desired compound as a yellow solid. MS (ESI pos. ion) m/z: 296. Calc'd for $C_{17}H_{14}FN_3O$: 295.11.

Step 3: Preparation of 2-fluoro-4-(2-(phenylamino)pyrimidin-5-yl)phenol

A mixture of 5-(3-fluoro-4-methoxyphenyl)-N-phenylpyrimidin-2-amine (Step 2, 0.066 g, 0.22 mmol), thiophenol (0.20 g, 1.0 mmol), and $K_2CO_3$ (0.15 g, 1.1 mmol) in NMP (2 mL) was heated at 120° C. for 20 h. The mixture was cooled to RT and diluted with $H_2O$ (4 mL). After stirring for 10 min, the resulting suspension was filtered, and the solid was further washed with $H_2O$. The solid was washed with hexanes to provide the title compound as a brown solid. MS (ESI pos. ion) m/z: 282. Calc'd for $C_{16}H_{12}FN_3O$: 281.10.

Step 4: Preparation of 5-(4-(6,7-dimethoxyquinolin-4-yloxy)-3-fluorophenyl)-N-phenylpyrimidin-2-amine A mixture of 4-chloro-6,7-dimethoxyquinoline (0.064 g, 0.28 mmol) and 2-fluoro-4-(2-(phenylamino)pyrimidin-5-yl)phenol (Step 3, 0.48 g, 0.17 mmol) in dioxane (1.0 mL) and pyridine (0.5 mL) was treated with a catalytic amount of DMAP (0.12 g, 0.1 mmol). The mixture was heated under microwave irradiation at 180° C. for 30 min. After cooling to RT, the mixture was diluted with NaOH (0.2 N, 6 mL), and the suspension was filtered. The resulting solid was further purified on silica with 0-5% ($NH_3$-MeOH in DCM) to afford the title compound as a white solid. MS (ESI pos. ion) m/z: 469. Calc'd for $C_{27}H_{21}FN_4O_3$: 468.16.

EXAMPLE 39

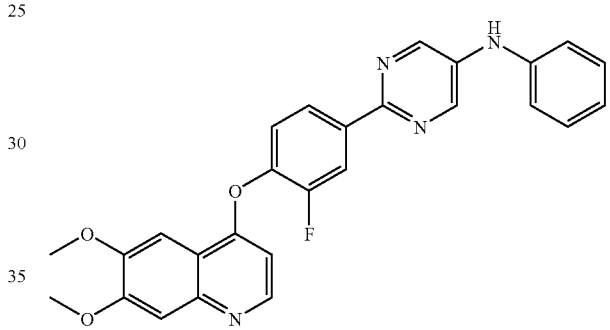

{2-[4-(6,7-Dimethoxy-quinolin-4-yloxy)-3-fluorophenyl]-pyrimidin-5-yl}-phenyl-amine

Step 1: Preparation of 5-bromo-2-(3-fluoro-4-methoxyphenyl)pyrimidine

To a mixture of 5-bromo-2-iodopyrimidine (3.0 g, 10 mmol) and 3-fluoro-4-methoxyphenylboronic acid (2.0 g, 12 mmol) in dioxane (15 mL) and $H_2O$ (5 mL) was added $Pd(dppf)Cl_2$—$CH_2Cl_2$ (0.1 g, 0.12 mmol) and $Na_2CO_3$ (2.0 g, 19 mmol) under argon. The mixture was stirred at RT for 20 h and was further heated at 80° C. for 20 h. The mixture was cooled to RT and was extracted with EtOAc. The organic layer was washed with $H_2O$, $NH_4Cl$ (sat), dried ($Na_2SO_4$), and concentrated. The crude residue was partitioned in 1:1 ether-$CH_2Cl_2$ and filtered to provide the title compound as a flake. The filtrate was concentrated and was triturated with MeOH to provide a second batch of product solid. MS (ESI pos. ion) m/z: 283, 285. Calc'd for $C_{11}H_8BrFN_2O$: 281.98.

Step 2: Preparation of 2-(3-fluoro-4-methoxyphenyl)-N-phenylpyrimidin-5-amine In a 50 mL round bottom flask under nitrogen was charged 5-bromo-2-(3-fluoro-4-methoxyphenyl)pyrimidine (Step 1, 0.40 g, 1.41 mmol), aniline (0.28 g, 3.0 mmol), $Pd(OAc)_2$ (0.015 g, 0.067 mmol), BINAP (0.090 g, 0.064 mmol), and $NaO^tBu$ (0.27 g, 2.8 mmol). Toluene (5.0 mL) was added and the mixture was heated at 100° C. for 24 h. The mixture was cooled to RT and was partitioned between CH$_2$Cl$_2$ and H$_2$O. The organic phase was dried over Na$_2$SO$_4$ and concentrated. Purification on silica with 1% MeOH in CH$_2$Cl$_2$ afforded the title compound as a purple solid. MS (ESI pos. ion) m/z: 296. Calc'd for C$_{17}$H$_{14}$FN$_3$O: 295.11.

Step 3: Preparation of {2-[4-(6,7-dimethoxy-quinolin-4-yloxy)-3-fluoro-phenyl]-pyrimidin-5-yl}-phenyl-amine A mixture of 5-(3-fluoro-4-methoxyphenyl)-N-phenylpyrimidin-2-amine (Step 2, 0.23 g, 0.78 mmol), thiophenol (0.50 g, 4.6 mmol), and K$_2$CO$_3$ (0.50 g, 3.6 mmol) in NMP (1.5 mL) was heated at 120° C. for 20 h. The mixture was cooled to RT and was diluted with H$_2$O (4 mL). Extraction with CH$_2$Cl$_2$ followed by flash chromatography on silica (1% MeOH in EtOAc) afforded the desired phenol as a dark orange film. (M+1/e: 282.) The phenol was mixed with 4-chloro-6,7-dimethoxyquinoline (0.26 g, 1.2 mmol), DMAP (0.030 g, 0.25 mmol) in pyridine (1.0 mL) and dioxane (1.0 mL). The mixture was heated at 110° C. for 14 h, concentrated, and heated further in toluene (5 mL). The residue was purified on silica using MeOH in CHCl$_3$ (0-3%). Part of the product fraction was dissolved in EtOAc and was washed with NaOH (1 N, 2×) to yield the title compound. MS (ESI pos. ion) m/z: 469. Calc'd for C$_{27}$H$_{21}$FN$_4$O$_3$: 468.16.

EXAMPLE 40

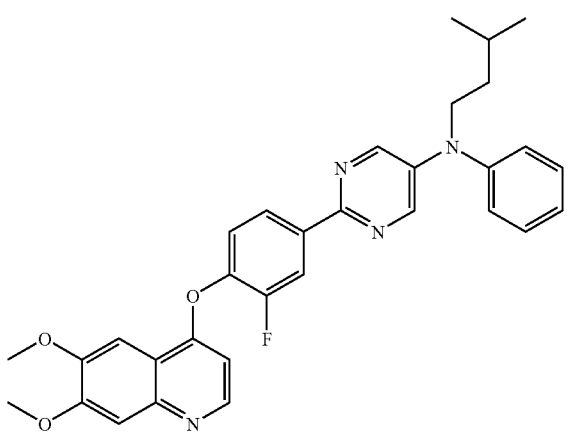

2-(4-(6,7-Dimethoxynaphthalen-1-yloxy)-3-fluorophenyl)-N-isopentyl-N-phenylpyrimidin-5-amine In a 10 mL dry flask with stirring bar was placed {2-[4-(6,7-dimethoxy-quinolin-4-yloxy)-3-fluoro-phenyl]-pyrimidin-5-yl}-phenyl-amine (Example 39, 0.030 g, 0.06 mmol) under N$_2$. Anhydrous THF (1.5 mL) was added, followed by the addition of NaH (60% dispersion, 0.10 g, 2.5 mmol). The resulting yellow mixture was heated at 50° C. for 20 min, then cooled to RT. 1-Bromo-3-methylbutane (0.20 mL) was added, and the resulting yellow mixture was heated at 50° C. for 4.5 h. The reaction was quenched with NH$_4$Cl (half sat.) and the slurry was filtered, then washed with H$_2$O. The brown solid was dissolved in CH$_2$Cl$_2$ and was purified on silica (50%-100% EtOAc in hexanes) to afford the title compound as a yellow solid. MS (ESI pos. ion) m/z: 539. Calc'd for C$_{32}$H$_{31}$FN$_4$O$_3$: 538.24.

EXAMPLE 41

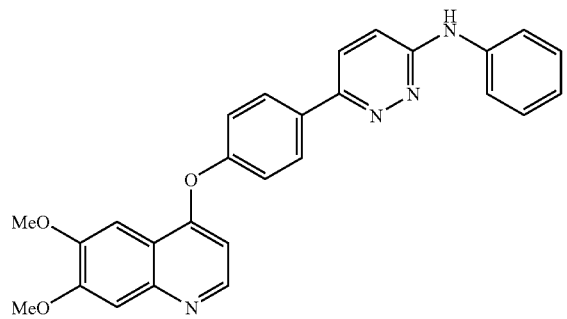

{6-[4-(6,7-Dimethoxy-quinolin-4-yloxy)-phenyl]-pyridazin-3-yl}-phenyl-amine

Step 1: Preparation of 3-Chloro-6-(4-methoxy-phenyl)-pyridazine

A mixture of 4-methoxyphenylboronic acid (3 g, 0.02 mol) and 3,6-dichloro-pyridazine (3.58 g, 0.024 mol) in 2 M Na$_2$CO$_3$/EtOH toluene (40 mL/20 mL/100 mL) was bubbled through N$_2$ for 5 min. Pd(PPh$_3$)$_4$ (1.15 g, 0.001 mol) was added under N$_2$ and the reaction was heated to 80° C. for 16 h. The mixture was diluted with 100 mL of EtOAc and 20 mL of water. The organic phase was separated, washed with 50 mL of brine, dried over Na$_2$SO$_4$ and concentrated in vacuo. The solid obtained was washed with 50% EtOAc/hexane to provide the title compound as off-white solid. MS (ESI pos. ion) m/z: 221.0 (M+H). Calc'd Exact Mass for C$_{11}$H$_9$ClN$_2$O: 220.65.

Step 2: Preparation of 4-(6-Chloro-pyridazin-3-yl)-phenol

A solution of 3-chloro-6-(4-methoxy-phenyl)-pyridazine (Step 1, 2.5 g, 0.0113 mol) in 1 M BBr$_3$/CH$_2$Cl$_2$ (34 mL) was stirred at RT for 16 h. The solution was concentrated in vacuo and the residue was re-dissolved in 100 mL of EtOAc. The organic phase was washed with 40 mL of water followed by 40 mL of brine, dried over Na$_2$SO$_4$ and concentrated in vacuo. The solid was washed with 50% EtOAc/hexane mixture to give the title compound as a yellow solid MS (ESI pos. ion) m/z: 207.2(M+H). Calc'd Exact Mass for C$_{10}$H$_7$ClN$_2$O: 206.63.

Step 3: Preparation of 4-(6-Phenylamino-pyridazin-3-yl)-phenol

To a solution of 4-(6-chloro-pyridazin-3-yl)-phenol (Step 2, 1 g, 4.84 mmol) and aniline (1.35 g, 14.52 mmol) in 20 mL of DMSO was added 5 drops of TFA. The reaction was heated to 80° C. for 16 h. The solution was cooled to RT and diluted with 100 mL of EtOAc. The organic phase was washed with 40 mL of water, 40 mL of brine, dried over Na$_2$SO$_4$ and concentrated in vacuo. The residue was purified by chromatography (50% EtOAc/hexane to EtOAc) to give the title compound as a white solid. MS (ESI pos. ion) m/z: 264.2(M+H). Calc'd Exact Mass for $C_{16}H_{13}N_3O$: 263.29.

Step 4: Preparation of {6-[4-(6,7-Dimethoxy-quinolin-4-yloxy)-phenyl]-pyridazin-3-yl}-phenyl-amine A mixture of 4-(6-phenylamino-pyridazin-3-yl)-phenol (Step 3, 0.25 g, 0.95 mmol), 4-chloro-6,7-dimethoxy-quinoline (0.212 g, 0.95 mmol), Cu powder 0.1 g) and NaOH pellet (0.1 g) in DMF/pyridine (1.5 mL/1.5 mL) was heated in a microwave (CEM Discover, 60 W, 120° C., ramp 12 min, hold 18 min). The reaction mixture was then diluted with 50 mL of EtOAc and washed with 20 mL of water followed by brine (20 mL). The organic phase was dried over $Na_2SO_4$ and concentrated in vacuo. The crude product was purified by column (50% EtOAc/hexane to EtOAc) to afford the title compound as a white solid. MS (ESI pos. ion) m/z: 451.2(M+H). Calc'd Exact Mass for $C_{27}H_{23}N_4O_3$: 450.49.

EXAMPLE 42

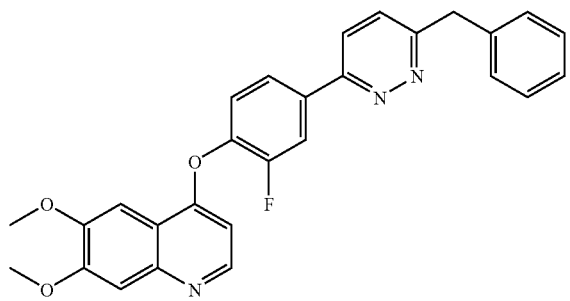

4-[4-(6-Benzyl-pyridazin-3-yl)-2-fluoro-phenoxy]-6,7-dimethoxy-quinoline

Step 1: Preparation of 3-Chloro-6-(3-fluoro-4-methoxy-phenyl)-pyridazine

A mixture of 3-fluoro-4-methoxyphenylboronic acid (10 g, 0.059 mol) and 3,6-dichloro-pyridazine (8.79 g, 0.059 mol) in 2 M $Na_2CO_3$/EtOH/toluene (80 mL/40 mL/200 mL) was bubbled through $N_2$ for 5 min. Cat. $Pd(PPh_3)_4$ (3.47 g, 0.003 mol) was added under $N_2$ and the reaction was heated to 80° C. for 16 h. The mixture was diluted with 200 mL of EtOAc and 40 mL of water. The organic phase was separated, washed with 80 mL of brine, dried over $Na_2SO_4$ and concentrated in vacuo. The solid obtained was washed with 50% EtOAc/hexane to provide off-white solid. MS (ESI pos. ion) m/z: 239.0 (M+H). Calc'd Exact Mass for $C_{11}H_8ClFN_2O$: 238.65.

Step 2: Preparation of 3-Benzyl-6-(3-fluoro-4-methoxy-phenyl)-pyridazine

A solution of 3-chloro-6-(3-fluoro-4-methoxy-phenyl)-pyridazine (Step 1, 2.0 g, 8.38 mmol), B-benzyl-9-BBN (0.5 mL in THF, 20 mL) and $K_2CO_3$ (3.5 g, 25.1 mmol) in 30 mL of DMF was degassed with $N_2$ for 5 min. Cat. $Pd(DPPF)Cl_2$ (731 mg, 1 mmol) was then added and the reaction was heated at 65° C. for 3 h (preheated oil bath). The mixture was poured into ice water and extracted with 50 mL 2×EtOAc. The combined organic phases were washed with 50 mL of brine and dried over $Na_2SO_4$. The solution was concentrated in vacuo and the crude was purified by silica gel column chromatograph (50% EtOAc/Hexane to EtOAc) to give light yellow solid. MS (ESI pos. ion) m/z: 295.3 (M+H). Calc'd Exact Mass for $C_{18}H_{15}FN_2O$: 294.32.

Step 3: Preparation of 4-(6-Benzyl-pyridazin-3-yl)-2-fluoro-phenol

A solution of 3-benzyl-6-(3-fluoro-4-methoxy-phenyl)-pyridazine (Step 2, 1.5 g, 5.1 mmol) in 25 mL of 1 M $BBr_3$/$CH_2Cl_2$ was stirred at RT for 16 h. The solution was then concentrated in vacuo and the residue was re-dissolved in 100 mL of EtOAc. The organic phase was washed with 40 mL of water followed by 40 mL of brine, dried over $Na_2SO_4$ and concentrated in vacuo to give the title compound. The solid has poor solubility in EtOAc and $CH_2Cl_2$ and was washed with 50% EtOAc/hexane and then used in the next step (yellow solid). MS (ESI pos. ion) m/z: 281.3 (M+H). Calc'd Exact Mass for $C_{17}H_{13}FN_2O$: 280.30.

Step 4: Preparation of 4-[4-(6-Benzyl-pyridazin-3-yl)-2-fluoro-phenoxy]-6,7-dimethoxy-quinoline A mixture of 4-Chloro-6,7-dimethoxy-quinoline (0.19 g, 0.85 mmol), 4-(6-benzyl-pyridazin-3-yl)-2-fluoro-phenol (Step 3, 0.2 g, 0.71 mmol) and DMAP (0.1 g, 0.85 mmol) in 6 mL of toluene was heated in a microwave (Personal Chemistry, Emrys Optimizer) at 180° C. for 2 h. The mixture was cooled to RT and diluted with 60 mL of EtOAc. The solution was washed with 20 mL of brine 2×, dried over $Na_2SO_4$ and concentrated in vacuo. The residue was further purified with silica gel column chromatography (50% to 100% EtOAc in hexanes) to provide title compound as a white solid. MS (ESI pos. ion) m/z: 487.3 (M+H). Calc'd Exact Mass for $C_{28}H_{22}FN_3O_3$: 467.49.

EXAMPLE 43

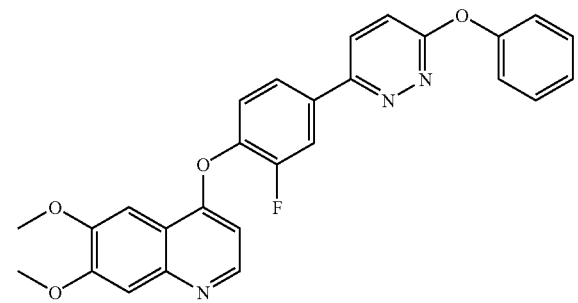

4-[2-Fluoro-4-(6-phenoxy-pyridazin-3-yl)-phenoxy]-6,7-dimethoxy-quinoline

Step 1: Preparation of 3-(3-Fluoro-4-methoxy-phenyl)-6-phenoxy-pyridazine

A mixture of 3-chloro-6-(3-fluoro-4-methoxy-phenyl)-pyridazine (1.0 g, 4019 mmol), phenol (0.26 g, 5.03 mmol) and $Cs_2CO_3$ (1.64 g, 5.03 mmol) in 15 mL of DMF (in microwave tube) was heated in a microwave (Personal Chemistry, Emrys Optimizer) at 150° C. for 15 min. The mixture was cooled to RT and diluted with 60 mL of EtOAc. The solution was washed with 20 mL of satd. NaHCO₃ followed by 20 mL of brine, dried over Na₂SO₄ and concentrated in vacuo. The solid was washed with 50% EtOAc/hexanes to provide the title compound as an off-white solid. MS (ESI pos. ion) m/z: 297.3 (M+H). Calc'd Exact Mass for $C_{17}H_{13}FN_2O_2$: 296.30.

Step 2: Preparation of
2-Fluoro-4-(6-phenoxy-pyridazin-3-yl)-phenol

A mixture of 3-(3-fluoro-4-methoxy-phenyl)-6-phenoxy-pyridazine (Step 1, 0.60 g, 2.0 mmol) and pyridine hydrochloride (3 g) was heated in an oil bath at 170° C. for 8 h. The sublimed pyridine hydrochloride on the top of the reaction flask was removed, and the residue (0.65 g) was used in the next step without further purification. MS (ESI pos. ion) m/z: 283.1 (M+H). Calc'd Exact Mass for $C_{16}H_{11}FN_2O_2$: 282.27.

Step 3: Preparation of 4-[2-Fluoro-4-(6-phenoxy-pyridazin-3-yl)-phenoxy]-6,7-dimethoxy-quinoline A mixture of 4-chloro-6,7-dimethoxy-quinoline (0.4 g, 1.79 mmol), 2-fluoro-4-(6-phenoxy-pyridazin-3-yl)-phenol (Step 2, 0.50 g, 1.79 mmol) and DMAP (0.22 g, 1.79 mmol) in 6 mL of toluene (in microwave tube) was heated in a microwave (Personal Chemistry, Emrys Optimizer) at 180° C. for 1 h.

The following Examples in Table 4 were prepared similar to the procedures described in the above Examples.

TABLE 4

| Ex. | Structure | Mol Formula | Mol Weight | MS (MH+) |
|---|---|---|---|---|
| 43a | 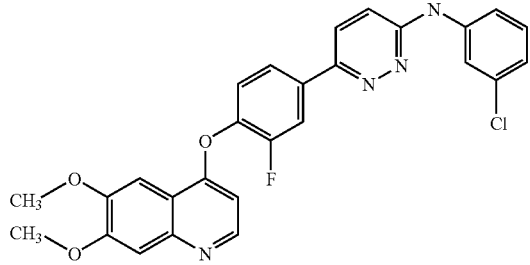 6-(4-((6,7-bis(methoxy)-4-quinolinyl)oxy)-3-fluorophenyl)-N-(3-chlorophenyl)-3-pyridazinamine | $C_{27}H_{20}ClFN_4O_3$ | 502.12 | 503 |
| 43b | 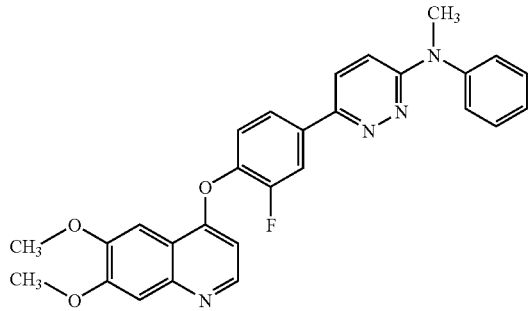 6-(4-((6,7-bis(methoxy)-4-quinolinyl)oxy)-3-fluorophenyl)-N-methyl-N-phenyl-3-pyridazinamine | $C_{28}H_{23}FN_4O_3$ | 482.18 | 483 |
| 43c | 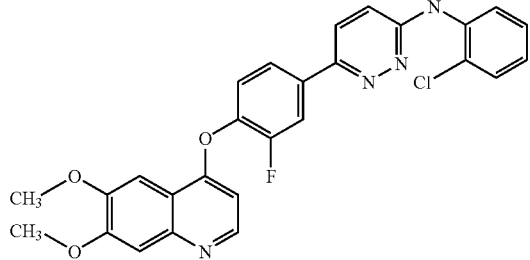 6-(4-((6,7-bis(methoxy)-4-quinolinyl)oxy)-3-fluorophenyl)-N-(2-chlorophenyl)-3-pyridazinamine | $C_{27}H_{20}ClFN_4O_3$ | 502.12 | 503 |

TABLE 4-continued

| Ex. | Structure | Mol Formula | Mol Weight | MS (MH+) |
|---|---|---|---|---|
| 43d | 6-(4-((6,7-bis(methoxy)-4-quinolinyl)oxy)-3-chlorophenyl)-N-phenyl-3-pyridazinamine | C₂₇H₂₁ClN₄O₃ | 484.13 | 485 |
| 43e | 4-((4-(6-(2,3-dihydro-1H-indol-1-yl)-3-pyridazinyl)-2-fluorophenyl)oxy)-6,7-bis(methoxy)quinoline | C₂₉H₂₃FN₄O₃ | 494.18 | 495 |
| 43f | 6-(4-((6,7-bis(methoxy)-4-quinolinyl)oxy)-3-fluorophenyl)-N-(3-fluorophenyl)-3-pyridazinamine | C₂₇H₂₀F₂N₄O₃ | 486.15 | 487 |
| 43g | 6-(4-((6,7-bis(methoxy)-4-quinolinyl)oxy)-3-fluorophenyl)-N-(2-methoxyphenyl)-3-pyridazinamine | C₂₈H₂₃FN₄O₄ | 498.17 | 499 |

TABLE 4-continued

| Ex. | Structure | Mol Formula | Mol Weight | MS (MH+) |
|---|---|---|---|---|
| 43h | 6-(3-fluoro-4-((6-methoxy-7-((3-(4-morpholinyl)propyl)oxy)-4-quinolinyl)oxy)phenyl)-N-phenyl-3-pyridazinamine | $C_{33}H_{32}FN_5O_4$ | 581.24 | 582 |
| 43i | 6-(4-((6,7-bis(methoxy)-4-quinolinyl)oxy)-3-fluorophenyl)-N-phenyl-3-pyridazinamine | $C_{27}H_{21}FN_4O_3$ | 468.16 | 469 |
| 43j | 6-(4-((6,7-bis(methoxy)-4-quinolinyl)oxy)phenyl)-N-(1H-pyrazol-3-yl)-3-pyridazinamine | $C_{24}H_{18}N_6O_3$ | 438.14 | 439 |
| 43k | 6-(4-((6,7-bis(methoxy)-4-quinolinyl)oxy)-3-fluorophenyl)-N-(2,2,2-trifluoroethyl)-3-pyridazinamine | $C_{23}H_{18}F_4N_4O_3$ | 474.13 | 475 |

TABLE 4-continued

| Ex. | Structure | Mol Formula | Mol Weight | MS (MH+) |
|---|---|---|---|---|
| 43l | 6-(4-((6,7-bis(methoxy)-4-quinolinyl)oxy)-3-fluorophenyl)-N-cyclopentyl-3-pyridazinamine | C₂₆H₂₅FN₄O₃ | 460.19 | 461 |
| 43m | 6-(4-((6,7-bis(methoxy)-4-quinolinyl)oxy)-3-fluorophenyl)-N-(2,3-dimethylphenyl)-3-pyridazinamine | C₂₉H₂₅FN₄O₃ | 496.19 | 497 |
| 43n | 6-(4-((6,7-bis(methoxy)-4-quinolinyl)oxy)-3-fluorophenyl)-N-(2-methylphenyl)-3-pyridazinamine | C₂₈H₂₃FN₄O₃ | 482.18 | 483 |
| 43o | 6-(4-((6,7-bis(methoxy)-4-quinolinyl)oxy)-2,5-difluorophenyl)-N-phenyl-3-pyridazinamine | C₂₇H₂₀F₂N₄O₃ | 486.15 | 487 |

EXAMPLE 44

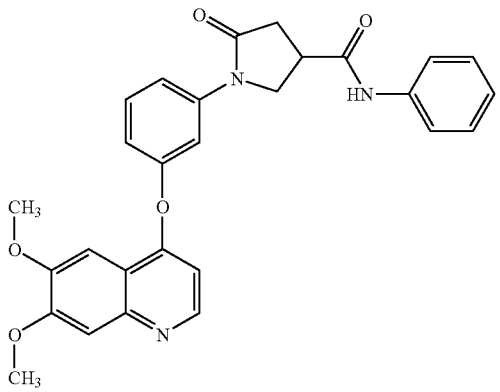

1-(4-(6,7-Dimethoxyquinolin-4-yloxy)phenyl)-5-oxo-N-phenylpyrrolidine-3-carboxamide

Step 1: Preparation of 1-(4-hydroxyphenyl)-5-oxo-pyrrolidine-3-carboxylic acid methyl ester A mixture of 4-amino-phenol (3 g, 0.027 mol) and 2-methylene-succinic acid dimethyl ester (4.35 g, 0.027 mol) was heated to 110° C. for 16 h. The dark brown glass was dissolved in EtOAc and purified by silica gel chromatography (20% EtOAc/hexane to EtOAC) to give the title compound as an orange oil. MS (ESI pos. ion) m/z: 236.2 (M+H). Calc'd Exact Mass for $C_{12}H_{13}NO_4$: 235.24.

Step 2: Preparation of methyl 1-(4-(6,7-dimethoxyquinolin-4-yloxy)phenyl)-5-oxopyrrolidine-3-carboxylate A mixture of 4-chloro-6,7-dimethoxy-quinoline (1.0 g, 4.45 mmol), 1-(4-hydroxyphenyl)-5-oxo-pyrrolidine-3-carboxylic acid methyl ester (Step 1, 1.6 g, 6.7 mmol) and DMAP (0.55 g, 4.45 mmol) in 30 mL of toluene (in 5 microwave tubes) was heated in a microwave (Personal Chemistry, Emrys Optimizer) at 180° C. for 1 h. The mixture was cooled to RT and diluted with 60 mL of EtOAc. The solution was washed with 20 mL of satd. NaHCO₃ followed by 20 mL of brine, dried over Na₂SO₄ and concentrated in vacuo. The residue was further purified with silica gel column chromatography (100% EtOAc to 15% MeOH in EtOAc) to provide the title compound as colorless glass. MS (ESI pos. ion) m/z: 423.2 (M+H). Calc'd Exact Mass for $C_{23}H_{22}N_2O_6$: 422.43.

Step 3: Preparation of 1-(4-(6,7-dimethoxyquinolin-4-yloxy)phenyl)-5-oxopyrrolidine-3-carboxylic acid To a solution of methyl 1-(4-(6,7-dimethoxyquinolin-4-yloxy)phenyl)-5-oxopyrrolidine-3-carboxylate (Step 2, 0.5 ng, 1.18 mmol) in MeOH/THF (2 mL: 2 mL) solution was added 1.77 mL of 1 N NaOH. The reaction was stirred at RT for 8 h. The solution was concentrated in vacuo to dryness and acidified with 1 N HCl. The white precipitate was collected by filtration and washed with 50% EtOAc/hexanes to give the title compound as white solid. MS (ESI pos. ion) m/z: 409.3 (M+H). Calc'd Exact Mass for $C_{22}H_{20}N_2O_6$: 408.4.

Step 4: Preparation of 1-(4-(6,7-dimethoxyquinolin-4-yloxy)phenyl)-5-oxo-N-phenylpyrrolidine-3-carboxamide To a solution of 1-(4-(6,7-dimethoxyquinolin-4-yloxy)phenyl)-5-oxopyrrolidine-3-carboxylic acid (Step 3, 120 mg, 0.29 mmol), aniline (55 mg, 0.59 mmol), HOBt (58 mg, 0.43 mmol) in 6 mL of DMF was added EDC (82 mg, 0.43 mmol) at RT. The reaction was stirred at RT for 16 h. The mixture was diluted with 50 mL of EtOAc, and the resulting solution was washed with 20 mL of satd. NaHCO₃ followed by 20 mL of brine. The organic phase was dried over Na₂SO₄ and concentrated in vacuo. The crude was purified by silica gel column chromatography (30% to 100% EtOAc/hexane then to 5% MeOH/EtOAc) to afford the title compound as a white solid. MS (ESI pos. ion) m/z: 484.5 (M+H). Calc'd Exact Mass for $C_{28}H_{25}N_3O_5$: 483.52.

EXAMPLE 45

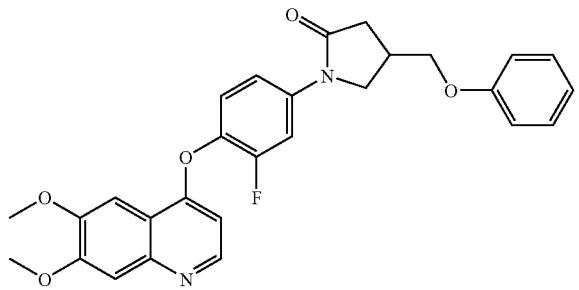

1-(4-(6,7-Dimethoxyquinolin-4-yloxy)-3-fluorophenyl)-4-(phenoxymethyl)pyrrolidin-2-one

Step 1: Preparation of 1-(3-fluoro-4-methoxyphenyl)-5-oxopyrrolidine-3-carboxylic acid A mixture of 3-fluoro-4-methoxybenzenamine (7.5 g, 0.053 mmol) and itaconic acid (6.9 g, 0.053 mmol) was heated to 110° C. for 2 h. The yellow solid was dissolved in 100 mL of MeOH and concentrated in vacuo. The resulting solid was washed with 50% EtOAc/hexanes to give the title compound as a light yellow solid. MS (ESI pos. ion) m/z: 254.2 (M+H). Calc'd Exact Mass for $C_{12}H_{12}FNO_4$: 253.23.

Step 2: Preparation of 1-(3-fluoro-4-methoxyphenyl)-4-(hydroxymethyl)pyrrolidin-2-one To a solution of 1-(3-fluoro-4-methoxyphenyl)-5-oxopyrrolidine-3-carboxylic acid (Step 1, 2 g, 7.9 mmol), Et₃N (1.65 mL, 9.48 mmol) in 30 mL of CH₂Cl₂ at 0° C. was added isobutyl chloroformate (1.23 mL, 9.48 mmol) via a syringe. The reaction was stirred at 0° C. for 1 h. The white precipitate was removed by filtration. The filtrate was cooled to 0° C. and NaBH₄ (0.9 g, 23.7 mmol) in water solution (3 mL) was added to the reaction. After 1 h, the mixture was diluted with 100 mL of EtOAc and 30 mL of satd. NaHCO₃ solution. The organic phase was separated and washed with 30 mL of brine, dried over Na₂SO₄ and concentrated in vacuo. The residue was chromatographed by a silica gel column (5% to 80% EtOAc/hexane) to give the title as a colorless glass. MS (ESI pos. ion) m/z: 240.4 (M+H). Calc'd Exact Mass for $C_{12}H_{14}FNO_3$: 239.24.

Step 3: Preparation of 1-(3-fluoro-4-methoxyphenyl)-4-(phenoxymethyl)pyrrolidin-2-one To a solution of 1-(3-fluoro-4-methoxyphenyl)-4-(hydroxymethyl)pyrrolidin-2-one (Step 2, 1.0 g, 4.18 mmol), phenol (0.786 g, 8.36 mmol) and PPh$_3$ (2.41 g, 9.2 mmol) in 50 mL of CH$_2$Cl$_2$ at 0° C. was added DIAD (1.65 mL, 9.2 mmol) slowly via a syringe. The reaction was warmed to RT and stirred overnight. The mixture was concentrated in vacuo and the residue was purified by chromatography (hexanes to 50% EtOAc/hexanes) to give the title compound as a white solid. MS (ESI pos. ion) m/z: 316.2 (M+H). Calc'd Exact Mass for C$_{18}$H$_{18}$FNO$_3$: 315.34.

Step 4: Preparation of 1-(3-fluoro-4-hydroxyphenyl)-4-(phenoxymethyl)pyrrolidin-2-one A solution of 1-(3-fluoro-4-methoxyphenyl)-4-(phenoxymethyl)pyrrolidin-2-one (Step 3, 1.0 g, 3.17 mmol) in 15.85 mL of 1 M BBr$_3$/CH$_2$Cl$_2$ was stirred at RT for 10 h. The solution was concentrated in vacuo and the residue was diluted with 100 mL of EtOAc. The organic phase was washed with 40 mL of satd. NaHCO$_3$ followed by 40 mL of brine, dried over Na$_2$SO$_4$ and concentrated in vacuo. The residue was purified by chromatography (5% to 60% EtOAc/hexane) to give the title compound as a light yellow foam. MS (ESI pos. ion) m/z: 302.3 (M+H). Calc'd Exact Mass for C$_{17}$H$_{16}$FNO$_3$: 301.31.

Step 5: Preparation of 1-(4-(6,7-dimethoxyquinolin-4-yloxy)-3-fluorophenyl)-4-(phenoxymethyl)pyrrolidin-2-one A mixture of 4-chloro-6,7-dimethoxyquinoline (0.185 g, 0.83 mmol), 1-(3-fluoro-4-hydroxyphenyl)-4-(phenoxymethyl)pyrrolidin-2-one (Step 4, 250 mg, 0.83 mmol) and DMAP (101 mg, 0.83 mmol) in 8 mL of toluene (in a microwave tube) was heated in a microwave (Personal Chemistry, Emrys Optimizer) at 180° C. for 1.5 h. The mixture was cooled to RT and diluted with 50 mL of EtOAc. The solution was washed with 20 mL of satd. NaHCO$_3$ followed by 20 mL of brine, dried over Na$_2$SO$_4$ and concentrated in vacuo. The residue was purified by chromatography (50% to 100% EtOAc/hexane) to provide the product as white solid. MS (ESI pos. ion) m/z: 489.3 (M+H). Calc'd Exact Mass for C$_{28}$H$_{25}$FN$_2$O$_5$: 488.51.

EXAMPLE 46

N-(1-(4-(6,7-Dimethoxyquinolin-4-yloxy)-3-fluorophenyl)-5-oxopyrrolidin-3-yl)benzamide

Step 1: Preparation of benzyl 1-(3-fluoro-4-methoxyphenyl)-5-oxopyrrolidin-3-ylcarbamate A solution of 1-(3-fluoro-4-methoxyphenyl)-5-oxopyrrolidine-3-carboxylic acid (1.5 g, 5.92 mmol), BnOH (1.92 g, 17.76 mmol), Et$_3$N (1.24 mL, 8.88 mmol) and DPPA (1.84 g, 7.12 mmol) in 100 mL of toluene was heated to 120° C. for 6 h. The reaction was cooled to RT and concentrated in vacuo. The residue was purified by chromatography on a silica gel column (10% to 70% EtOAC/hexane) to give the title compound as colorless crystal. MS (ESI pos. ion) m/z: 359.4 (M+H). Calc'd Exact Mass for C$_{19}$H$_{19}$FN$_2$O$_4$: 358.36.

Step 2: Preparation of 4-amino-1-(3-fluoro-4-methoxyphenyl)pyrrolidin-2-one

In a round-bottomed flask containing a mixture of benzyl 1-(3-fluoro-4-methoxyphenyl)-5-oxopyrrolidin-3-ylcarbamate (Step 1, 1.5 g, 4.2 mmol) and 200 mg of Pd/C in 100 mL of EtOAc was applied with a H$_2$ balloon. The reaction was stirred at RT for 8 h, and filtered with the aid of Celite®. The filtrate was concentrated in vacuo to give the title compound as a white solid. MS (ESI pos. ion) m/z: 225.3 (M+H). Calc'd Exact Mass for C$_{11}$H$_{13}$FN$_2$O$_2$: 224.23.

Step 3: Preparation of N-(1-(3-fluoro-4-methoxyphenyl)-5-oxopyrrolidin-3-yl)benzamide To a mixture of 4-amino-1-(3-fluoro-4-methoxyphenyl)pyrrolidin-2-one (Step 2, 0.8 g, 3.57 mmol) and K$_2$CO$_3$ (0.99 g, 7.14 mmol) in 20 mL of CH$_2$Cl$_2$ was added benzoyl chloride (0.75 g, 5.35 mmol). The reaction was stirred at RT for 16 h. The solid in the reaction was removed by filtration and the filtrate was diluted with 20 mL of CH$_2$Cl$_2$. The resulted solution was washed with 20 mL of satd. NaHCO$_3$ followed by 20 mL of brine, dried over Na$_2$SO$_4$ and concentrated in vacuo. The residue was purified by chromatography (30% to 100% EtOAc/hexane) to provide the title compound as a white solid. MS (ESI pos. ion) m/z: 329.4 (M+H). Calc'd Exact Mass for C$_{18}$H$_{17}$FN$_2$O$_3$: 328.34.

Step 4: Preparation of N-(1-(3-fluoro-4-hydroxyphenyl)-5-oxopyrrolidin-3-yl)benzamide A mixture of N-(1-(3-fluoro-4-methoxyphenyl)-5-oxopyrrolidin-3-yl)benzamide (Step 3, 0.9 g, 2.74 mmol) in 14 mL of 1 M BBr$_3$/CH$_2$Cl$_2$ was stirred at RT for 16 h. The solution was concentrated in vacuo and the residue was diluted with 50 mL of MeOH and concentrated in vacuo again. The resulting yellow solid was washed with 50% EtOAc/hexane to give a yellow solid. MS (ESI pos. ion) m/z: 315.3 (M+H). Calc'd Exact Mass for C$_{17}$H$_{15}$FN$_2$O$_3$: 314.31.

Step 5: Preparation of N-(1-(4-(6,7-dimethoxyquinolin-4-yloxy)-3-fluorophenyl)-5-oxopyrrolidin-3-yl)benzamide A mixture of 4-chloro-6,7-dimethoxyquinoline (0.14 g, 0.6 mmol), N-(1-(3-fluoro-4-hydroxyphenyl)-5-oxopyrrolidin-3-yl)benzamide (Step 4, 0.20 g, 0.6 mmol) and DMAP (78 mg, 0.6 mmol) in 2 mL of dioxane (in a microwave tube) was heated in a microwave (Personal Chemistry, Emrys Optimizer) at 160° C. for 1 h. The mixture was cooled to RT and diluted with 50 mL of EtOAc. The solution was washed with

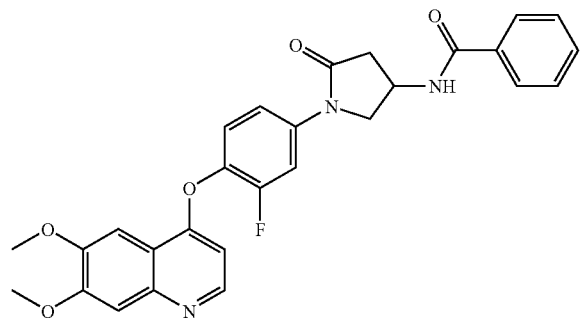

20 mL of satd. NaHCO$_3$ followed by 20 mL of brine, dried over Na$_2$SO$_4$ and concentrated in vacuo. The residue was purified by chromatography (50% to 100% EtOAc in hexanes then to 5% MeOH/EtOAc) to provide a white solid. MS (ESI pos. ion) m/z: 502.3 (M+H). Calc'd Exact Mass for C$_{28}$H$_{24}$FN$_3$O$_5$: 501.51.

EXAMPLE 47

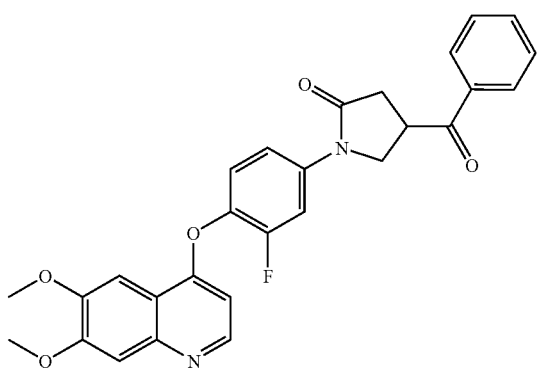

4-Benzoyl-1-(4-(6,7-dimethoxyquinolin-4-yloxy)-3 fluorophenyl)pyrrolidin-2-one

Step 1: Preparation of 1-(3-fluoro-4-methoxyphenyl)-N-methoxy-N-methyl-5-oxopyrrolidine-3-carboxamide To a solution of 1-(3-fluoro-4-methoxyphenyl)-5-oxopyrrolidine-3-carboxylic acid (5 g, 19.7 mmol), N-methoxymethanamine hydrochloride (2.18 g, 22.4 mmol), HOBt (4.0 g, 29.7 mmol) and Et$_3$N (4.2 mL, 29.7 mmol) in 60 mL of DMF was added EDC (5.7 g, 29.7 mmol) at 0° C. The reaction was warmed to RT in 1 h and stirred at RT for 16 h. The mixture was diluted with 100 mL of EtOAc, and the resulted solution was washed with 50 mL of satd. NaHCO$_3$ followed by 50 mL of brine. The organic phase was dried over Na$_2$SO$_4$ and concentrated in vacuo. The crude residue was re-crystallized in 80% EtOAc/hexane to afford white solid. MS (ESI pos. ion) m/z: 297.3 (M+H). Calc'd Exact Mass for C$_{14}$H$_{17}$FN$_2$O$_4$: 296.29.

Step 2: Preparation of 4-benzoyl-1-(3-fluoro-4-methoxyphenyl)pyrrolidin-2-one

To a solution of 1-(3-fluoro-4-methoxyphenyl)-N-methoxy-N-methyl-5-oxopyrrolidine-3-carboxamide (Step 1, 2 g, 6.75 mmol) in 30 mL of THF was added 2 M phenylmagnesium chloride in THF (6.75 mL) via syringe at RT. The solution was heated to 50° C. for 2 h. The solution was poured to 50 mL of satd. NH$_4$Cl aq. soln. The resulting mixture was extracted with 100 mL of EtOAc. The organic phase was washed with 50 mL of brine, dried over Na$_2$SO$_4$ and concentrated in vacuo. The crude was purified by a silica gel column chromatography (10% to 80% EtOAc/hexane) to give white solid. MS (ESI pos. ion) m/z: 314.2 (M+H). Calc'd Exact Mass for C$_{18}$H$_{16}$FNO$_3$: 313.32.

Step 3: Preparation of 4-benzoyl-1-(3-fluoro-4-hydroxyphenyl)pyrrolidin-2-one

A mixture of 4-benzoyl-1-(3-fluoro-4-methoxyphenyl) pyrrolidin-2-one (Step 2, 1.0 g, 3.2 mmol) in 20 mL of 1 M BBr$_3$/CH$_2$Cl$_2$ was stirred at RT for 16 h. The solution was concentrated in vacuo and the residue was diluted with 50 mL of MeOH and concentrated in vacuo again. The resulting white solid was washed with 50% EtOAc/hexane to give the title compound. MS (ESI pos. ion) m/z: 300.4 (M+H). Calc'd Exact Mass for C$_{17}$H$_{14}$FNO$_3$: 299.3.

Step 4: Preparation of 4-benzoyl-1-(4-(6,7-dimethoxyquinolin-4-yloxy)-3 fluorophenyl)pyrrolidin-2-one A mixture of 4-chloro-6,7-dimethoxyquinoline (0.38 g, 1.67 mmol), 4-benzoyl-1-(3-fluoro-4-hydroxyphenyl)pyrrolidin-2-one (Step 3, 0.40 g, 1.67 mmol) and DMAP (0.204 g, 1.67 mmol) in 4 mL of dioxane (in a microwave tube) was heated in a microwave (Personal Chemistry, Emrys Optimizer) at 160° C. for 1 h. The mixture was cooled to RT and diluted with 50 mL of EtOAc. The solution was washed with 20 mL of satd. NaHCO$_3$ followed by 20 mL of brine, dried over Na$_2$SO$_4$ and concentrated in vacuo. The residue was purified by chromatography (50% to 100% EtOAc in hexanes then to 5% MeOH/EtOAc) to provide a white solid. MS (ESI pos. ion) m/z: 487.4 (M+H). Calc'd Exact Mass for C$_{28}$H$_{23}$FN$_2$O$_5$: 486.49.

EXAMPLE 48

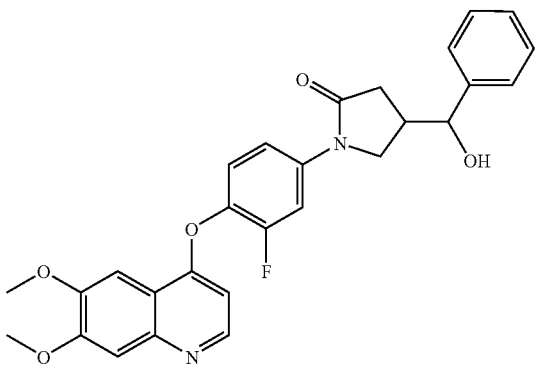

1-(4-(6,7-Dimethoxyquinolin-4-yloxy)-3-fluorophenyl)-4-(hydroxy(phenyl)methyl)pyrrolidin-2-one To a solution of 4-benzoyl-1-(4-(6,7-dimethoxyquinolin-4-yloxy)-3-fluorophenyl)pyrrolidin-2-one (Example 47, 0.2 g, 0.41 mmol) in 15 mL of MeOH was slowly added solid NaBH$_4$ (50 mg, 1.32 mmol). The reaction was stirred at RT for 1 h. The reaction was quenched with 10 mL of satd. NH$_4$Cl solution. The solution was diluted with 100 mL of EtOAc and was washed with 30 mL of satd. NH$_4$Cl followed by 30 mL of brine, dried over Na$_2$SO$_4$ and concentrated in vacuo. The crude solid was purified by chromatography (EtOAc to 5% MeOH/EtOAc) to give a colorless film. MS (ESI pos. ion) m/z: 489.3 (M+H). Calc'd Exact Mass for C$_{28}$H$_{25}$FN$_2$O$_5$: 488.51.

EXAMPLE 49

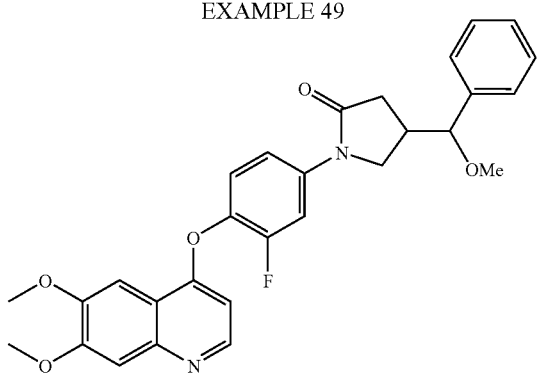

1-(4-(6,7-Dimethoxyquinolin-4-yloxy)-3-fluorophenyl)-4-(methoxy(phenyl)methyl)pyrrolidin-2-one To a solution of 1-(4-(6,7-dimethoxyquinolin-4-yloxy)-3-fluorophenyl)-4-(hydroxy(phenyl)methyl)pyrrolidin-2-one (Example 48, 0.1 g, 0.2 mmol) in THF/DMF (1 mL:1 mL) was added NaH (0.1 g, 2.5 mmol) solid. The reaction was stirred at RT for 1 h. MeI (0.1 mL, 1.6 mmol) was added via a syringe and the reaction was stirred for 1 h. The reaction was quenched with 10 mL of satd. NH$_4$Cl solution and 10 mL of water. The solution was diluted with 50 mL of EtOAc. The organic phase was separated and was washed with 30 mL of brine, dried over Na$_2$SO$_4$ and concentrated in vacuo. The crude oil was purified by chromatography (10% EtOAc/hexanes to EtOAc) to give colorless film. MS (ESI pos. ion) m/z: 503.5 (M+H). Calc'd Exact Mass for C$_{29}$H$_{27}$FN$_2$O$_5$: 502.53.

EXAMPLE 50

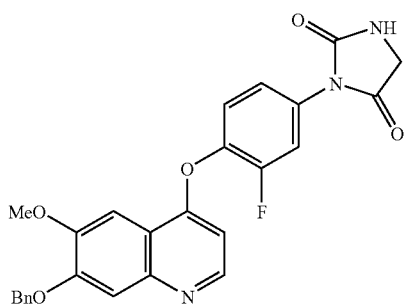

3-(4-(7-(Benzyloxy)-6-methoxyquinolin-4-yloxy)-3-fluorophenyl)imidazolidine-2,4-dione Step 1: Preparation of 7-(benzyloxy)-4-(2-fluoro-4-nitrophenoxy)-6-methoxyquinoline To a stirred suspension of 7-(benzyloxy)-6-methoxyquinolin-4-ol (4.0 g, 14.2 mmol) and Cs$_2$CO$_3$ (11.5 g, 35.5 mmol) in DMF (40 mL) at 40° C. under N$_2$ was added 3,4-difluoronitrobenzene (1.6 mL, 14.2 mmol). The suspension stirred at 40° C. for 45 min. Solvent was removed under reduced pressure and the residue was partitioned between CH$_2$Cl$_2$ (150 mL) and 1 N NaOH (50 mL). The organic layer was washed with water (50 mL) and brine (25 mL) and purified on silica gel yielding the title compound. Calc'd Mass for C$_{23}$H$_{17}$FN$_2$O$_5$, 420, MS (M+1) 421.

Step 2: Preparation of 4-(7-(benzyloxy)-6-methoxyquinolin-4-yloxy)-3-fluorobenzenamine To a stirring solution of 7-(benzyloxy)-4-(2-fluoro-4-nitrophenoxy)-6-methoxyquinoline (Step 1, 4.5 g, 10.7 mmol) and hydrazine (2 mL, 61 mmol) in THF (200 mL) was added Raney 2400 nickel (1 mL slurry in water). The suspension was stirred for 30 min. The mixture was filtered through a bed of Celite®, then solvents were removed under reduced pressure to afford the title compound. Calc'd Mass for C$_{23}$H$_{19}$FN$_2$O$_3$, 390, MS (M+1) 391.

Step 3: Preparation of 3-(4-(7-(benzyloxy)-6-methoxyquinolin-4-yloxy)-3-fluorophenyl)imidazolidine-2,4-dione To a stirring solution of 4-(7-(benzyloxy)-6-methoxyquinolin-4-yloxy)-3-fluorobenzenamine (Step 2, 1.0 g, 2.6 mmol) in THF (15 mL) was added ethyl isocyanotoacetate (1 mL, 6 mmol). After 3 h at RT, solvent was removed under reduced pressure and the resulting residue was purified on silica gel, yielding a white solid. (M+1)=520.

To the white solid (700 mg, 1.3 mmol) in dioxane (100 mL) was added DBU (0.3 mL, 2.0 mmol). The reaction was stirred at RT overnight. The solvent was removed under reduced pressure to afford the title compound. Calc'd Mass for C$_{26}$H$_{20}$FN$_3$O$_5$, 473, MS (M+1) 474.

EXAMPLE 51

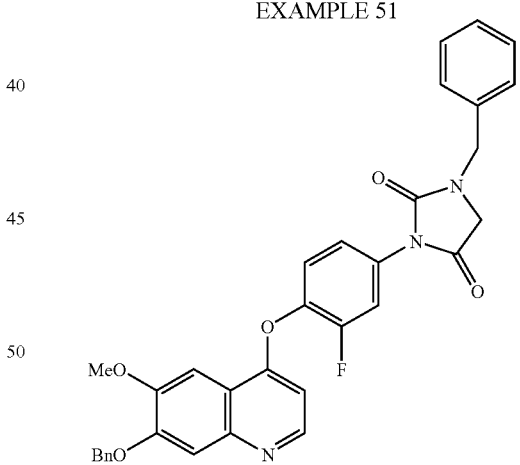

1-Benzyl-3-(4-(7-(benzyloxy)-6-methoxyquinolin-4-yloxy)-3-fluorophenyl)imidazolidine-2,4-dione To a stirring suspension of 3-(4-(7-(benzyloxy)-6-methoxyquinolin-4-yloxy)-3-fluorophenyl)imidazolidine-2,4-dione (Example 50, 200 mg, 0.42 mmol) and benzyl bromide (0.06 mL, 0.51 mmol) in THF (2 mL) and DMF (1 mL) was added 1 M LiHMDS in THF (0.51 mL). After 3 h at RT, the solvents were removed under reduced pressure and the residue was purified on a silica gel to afford the title compound. Calc'd Mass for C$_{33}$H$_{26}$FN$_3$O$_5$, 563, MS (M+1) 564.

EXAMPLE 52

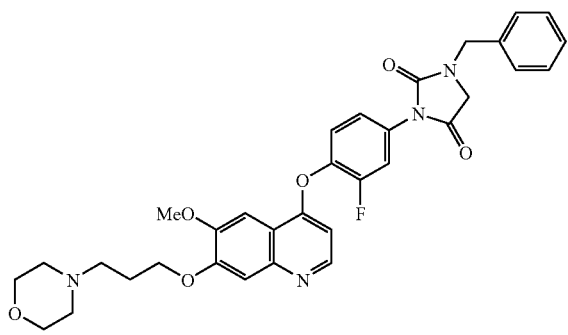

1-Benzyl-3-(3-fluoro-4-(6-methoxy-7-(3-morpholino-propoxy)quinolin-4-yloxy)phenyl)imidazolidine-2,4-dione To a stirring solution of 1-benzyl-3-(4-(7-(benzyloxy)-6-methoxyquinolin-4-yloxy)-3-fluorophenyl)imidazolidine-2,4-dione (Example 51, 0.25 mg, 0.22 mmol) in THF (5 mL) and MeOH (1 mL) over an argon atmosphere was added 20% palladium hydroxide on carbon (20 mg). The suspension was stirred for 3 h at RT then filtered through a bed of Celite®. The filtrate was concentrated, and to the residue (75 mg, 0.16 mmol) and $Cs_2CO_3$ (67 mg, 0.21 mmol) in THF (0.5 mL) and DMF (0.5 mL) was added 1-bromo-3-chloropropane (0.02 mL, 0.21 mmol). After 2 h at RT, solvents were removed under reduced pressure. The resulting residue was purified on silica gel to provide a colorless film.

To the film (60 mg, 0.11 mmol) and NaI (25 mg, 0.16 mmol) in DMF (0.5 mL) was added morpholine (0.05 mL, 0.55 mmol). The suspension was stirred at 60° C. overnight. Solvent was removed under reduced pressure and the resulting residue was purified on silica gel to afford the title compound. Calc'd Mass for $C_{33}H_{33}FN_4O_6$, 600, MS (M+1) 601.

EXAMPLE 53

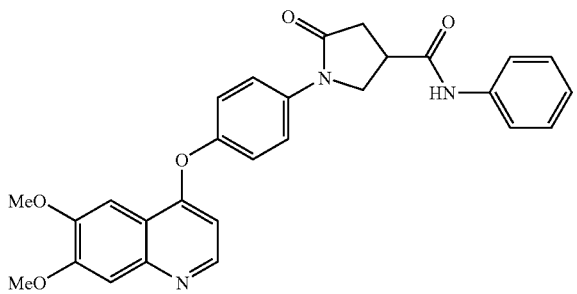

1-(4-(6,7-dimethoxyquinolin-4-yloxy)phenyl)-5-oxo-N-phenylpyrrolidine-3-carboxamide Step 1: Preparation of 1-(4-Hydroxy-phenyl)-5-oxopyrrolidine-3-carboxylic acid methyl ester A mixture of 4-amino-phenol (3 g, 0.027 mol) and 2-methylene-succinic acid dimethyl ester (4.35 g, 0.027 mol) was heated to 110° C. for 16 h. The dark brown glass was dissolved in EtOAc and purified by silica gel chromatography (20% EtOAc/hexane to EtOAc) to give an orange oil. MS (ESI pos. ion) m/z: 236.2 (M+H). Calc'd Exact Mass for $C_{12}H_{13}NO_4$: 235.24.

Step 2: Preparation of Methyl 1-(4-(6,7-dimethoxyquinolin-4-yloxy)phenyl)-5-oxopyrrolidine-3-carboxylate A mixture of 4-chloro-6,7-dimethoxy-quinoline (1.0 g, 4.45 mmol), 1-(4-hydroxy-phenyl)-5-oxo-pyrrolidine-3-carboxylic acid methyl ester (1.6 g, 6.7 mmol) and DMAP (0.55 g, 4.45 mmol) in 30 mL of toluene (in 5 microwave tubes) was heated in a microwave (Personal Chemistry, Emrys Optimizer) at 180° C. for 1 h. The reaction mixture was cooled to RT and diluted with 60 mL of EtOAc. The solution was washed with 20 mL of satd. $NaHCO_3$ followed by 20 mL of brine, dried over $Na_2SO_4$ and concentrated in vacuo. The residue was further purified with silica gel column chromatography (100% EtOAc to 15% MeOH in EtOAc) to provide colorless glass. MS (ESI pos. ion) m/z: 423.2 (M+H). Calc'd Exact Mass for $C_{23}H_{22}N_2O_6$: 422.43.

Step 3: Preparation of 1-(4-(6,7-dimethoxyquinolin-4-yloxy) phenyl)-5-oxopyrrolidine-3-carboxylic acid To a solution of methyl 1-(4-(6,7-dimethoxyquinolin-4-yloxy)phenyl)-5-oxopyrrolidine-3-carboxylate (Step 2, 0.5 g, 1.18 mmol) in MeOH/THF (2 mL: 2 mL) solution was added 1.77 mL of 1 N NaOH. The reaction was stirred at RT for 8 h. The solution was concentrated in vacuo to dryness and was acidified with 1 N HCl. The white precipitate was collected by filtration and was washed with 50% EtOAc/hexanes to give the title compound as a white solid. MS (ESI pos. ion) m/z: 409.3 (M+H). Calc'd Exact Mass for $C_{22}H_{20}N_2O_6$: 408.4.

Step 4: Preparation of 1-(4-(6,7-dimethoxyquinolin-4-yloxy) phenyl)-5-oxo-N-phenylpyrrolidine-3-carboxamide To a solution of 1-(4-(6,7-dimethoxyquinolin-4-yloxy) phenyl)-5-oxopyrrolidine-3-carboxylic acid (Step 3, 120 mg, 0.29 mmol), aniline (55 mg, 0.59 mmol), HOBt (58 mg, 0.43 mmol) in 6 mL of DMF was added EDCI (82 mg, 0.43 mmol) at RT. The reaction was stirred at RT for 16 h. The mixture was diluted with 50 mL of EtOAc, and the resulting solution was washed with 20 mL of satd. NaHCO$_3$ followed by 20 mL of brine. The organic phase was dried over Na$_2$SO$_4$ and concentrated in vacuo. The residue was purified by silica gel column chromatography (30% to 100% EtOAc/hexane then to 5% MeOH/EtOAc) to afford the title compound as a white solid. MS (ESI pos. ion) m/z: 484.5 (M+H). Calc'd Exact Mass for C$_{28}$H$_{25}$N$_3$O$_5$: 483.52.

EXAMPLE 54

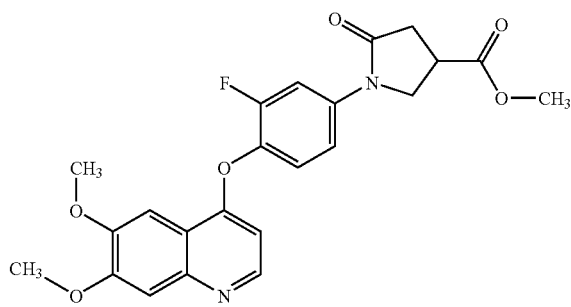

Methyl (3R)-1-(4-((6,7-bis(methoxy)-4-quinolinyl)oxy)-3-fluorophenyl)-5-oxo-3-pyrrolidinecarboxylate

EXAMPLE 55

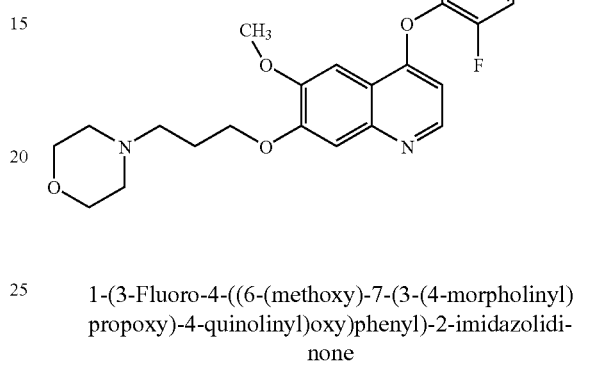

1-(3-Fluoro-4-((6-(methoxy)-7-(3-(4-morpholinyl)propoxy)-4-quinolinyl)oxy)phenyl)-2-imidazolidinone The following Examples in Table 5 were prepared similar to the procedures described in the above Examples.

TABLE 5

| Ex. | Structures | Mol Formula | Mol Weight | MS (MH+) |
|---|---|---|---|---|
| 56 | 1-(4-((6,7-bis(methoxy)-4-quinolinyl)oxy)-3-fluorophenyl)-4-((ethoxy)(phenyl)methyl)-2-pyrrolidinone | C$_{30}$H$_{29}$FN$_2$O$_5$ | 516.57 | 517.4 |
| 57 | 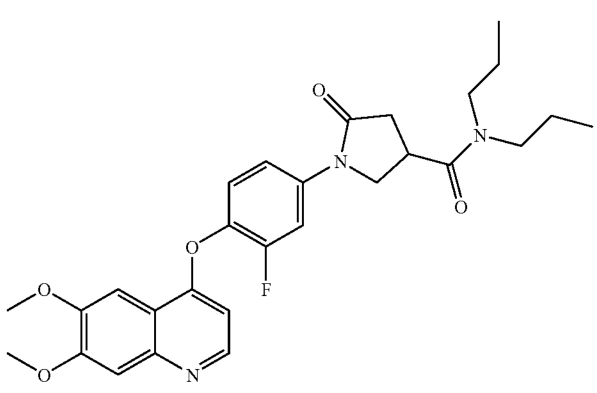 | C$_{28}$H$_{32}$FN$_3$O$_5$ | 509.57 | 510.6 |

TABLE 5-continued

| Ex. | Structures | Mol Formula | Mol Weight | MS (MH+) |
|---|---|---|---|---|
| | 1-(4-((6,7-bis (methoxy)-4-quinolinyl)oxy)-3-fluorophenyl)-5-oxo-N,N-dipropyl-3-pyrrolidinecarboxamide | | | |
| 58 | 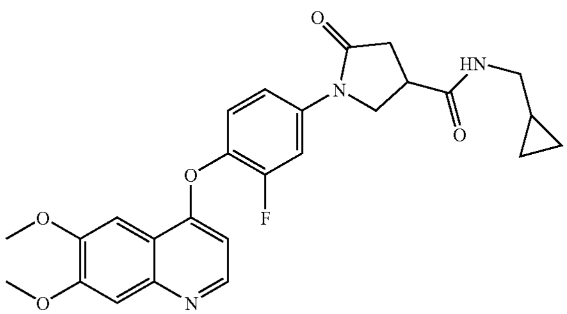 | $C_{26}H_{26}FN_3O_5$ | 479.51 | 480.4 |
| | 1-(4-((6,7-bis (methoxy)-4-quinolinyl)oxy)-3-fluorophenyl)-N-(cyclopropylmethyl)-5-oxo-3-pyrrolidinecarboxamide | | | |
| 59 | 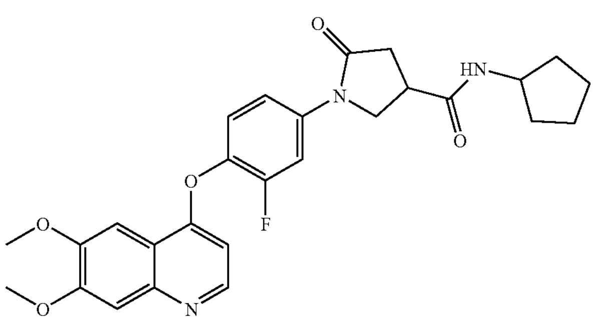 | $C_{27}H_{28}FN_3O_5$ | | 494.1 |
| | 1-(4-((6,7-bis(methoxy)-4-quinolinyl)oxy)-3-fluorophenyl)-N-cyclopentyl-5-oxo-3-pyrrolidinecarboxamide | | | |
| 60 | 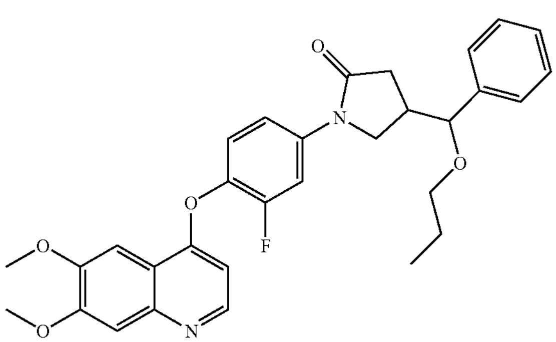 | $C_{31}H_{31}FN_2O_5$ | 530.59 | 531.2 |

TABLE 5-continued

| Ex. | Structures | Mol Formula | Mol Weight | MS (MH+) |
|---|---|---|---|---|
| | 1-(4-((6,7-bis(methoxy)-4-quinolinyl)oxy)-3-fluorophenyl)-4-(phenyl(propoxy)methyl)-2-pyrrolidinone | | | |
| 61 | 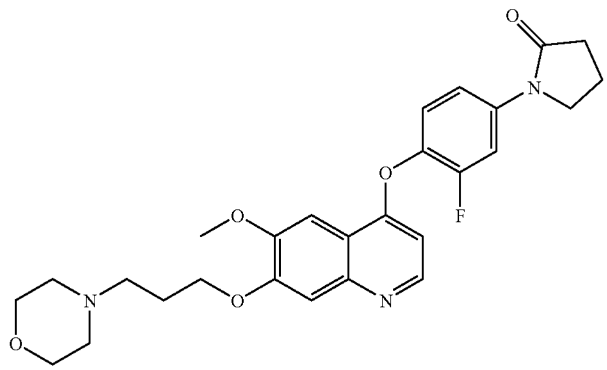 | $C_{27}H_{30}FN_3O_5$ | 495.54 | 496.4 |
| | 1-(3-fluoro-4-((6-(methoxy)-7-((3-(4-morpholinyl)propyl)oxy)-4-quinolinyl)oxy)phenyl)-2-pyrrolidinone | | | |
| 62 | 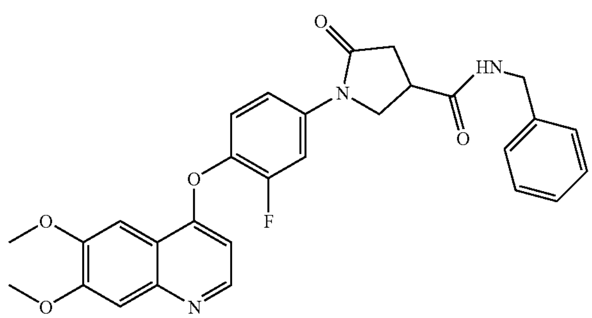 | $C_{29}H_{27}FN_3O_5$ | 497.54 | 498.3 |
| | 1-(4-((6,7-bis(methoxy)-4-quinolinyl)oxy)phenyl)-5-oxo-N-(phenylmethyl)-3-pyrrolidinecarboxamide | | | |
| 63 | 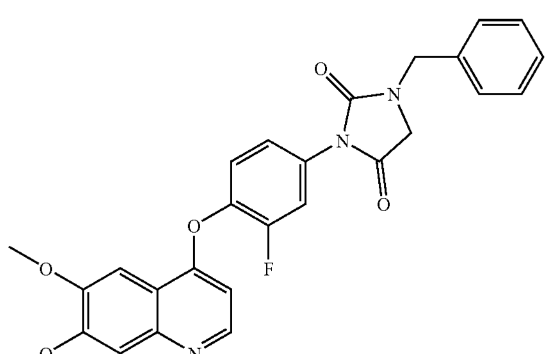 | $C_{27}H_{22}FN_3O_5$ | 487 | 488 |
| | 3-(4-((6,7-bis(methoxy)-4-quinolinyl)oxy)-3-fluorophenyl)-1-(phenylmethyl)-2,4-imidazolidinedione | | | |

TABLE 5-continued

| Ex. | Structures | Mol Formula | Mol Weight | MS (MH+) |
|---|---|---|---|---|
| 64 | 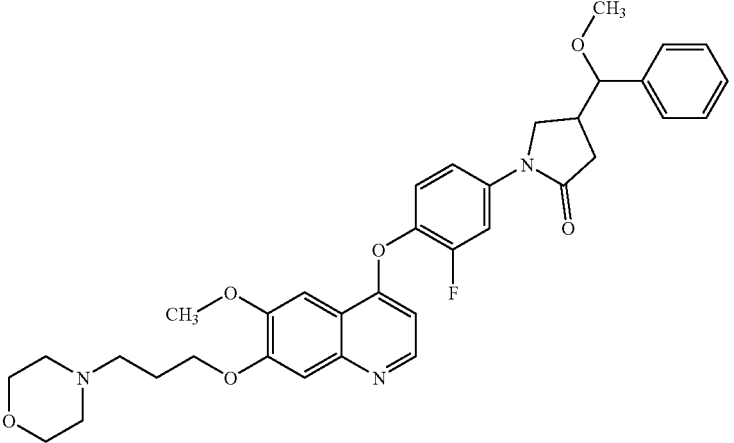<br>1-{3-Fluoro-4-[6-methoxy-7-(3-morpholin-4-yl-propoxy)-quinolin-4-yloxy]-phenyl}-4-(methoxy-phenyl-methyl)-pyrrolidin-2-one | C₃₅H₃₈FN₃O₆ | 615.27 | 616 |
| 65 | 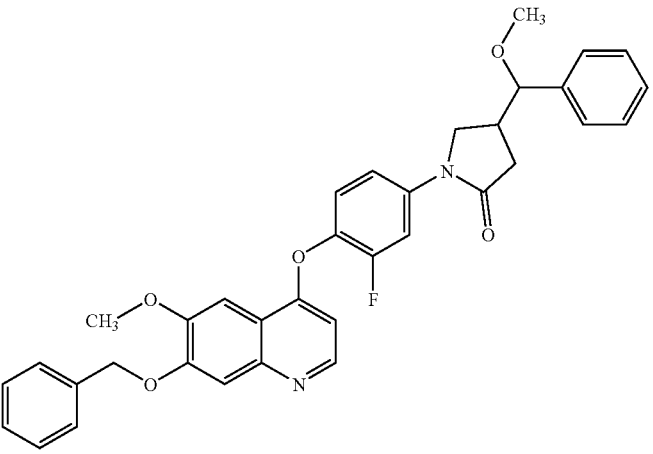<br>1-[4-(7-Benzyloxy-6-methoxy-quinolin-4-yloxy)-3-fluoro-phenyl]-4-(methoxy-phenyl-methyl)-pyrrolidin-2-one | C₃₅H₃₁FN₂O₅ | 578.22 | 579 |
| 66 | 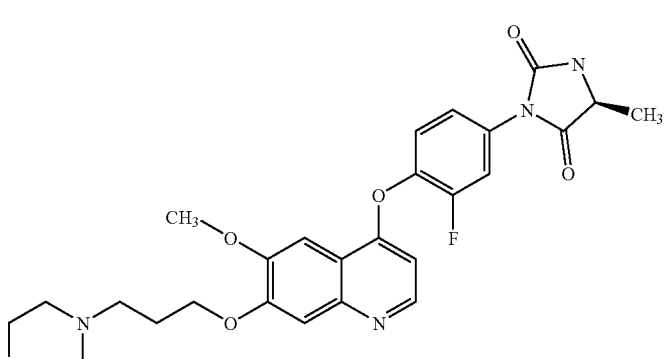<br>3-{3-Fluoro-4-[6-methoxy-7-(3-morpholin-4-yl-propoxy)-quinolin-4-yloxy]-phenyl}-5-methyl-imidazolidine-2,4-dione | C₂₇H₂₉FN₄O₆ | 524.21 | 525 |

TABLE 5-continued
| Ex. | Structures | Mol Formula | Mol Weight | MS (MH+) |
|---|---|---|---|---|
| 67 | 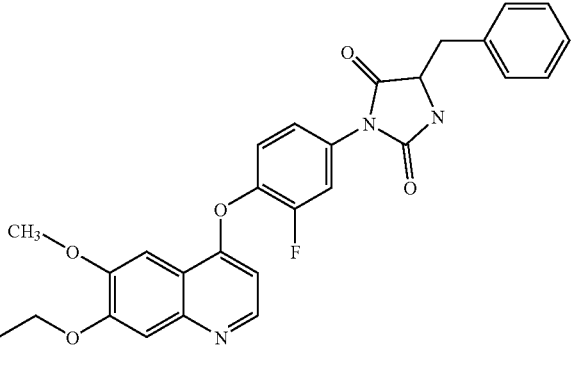 5-Benzyl-3-{3-fluoro-4-[6-methoxy-7-(3-morpholin-4-yl-propoxy)-quinolin-4-yloxy]-phenyl}-imidazolidine-2,4-dione | $C_{33}H_{33}FN_4O_6$ | 600.24 | 601 |
| 68 | 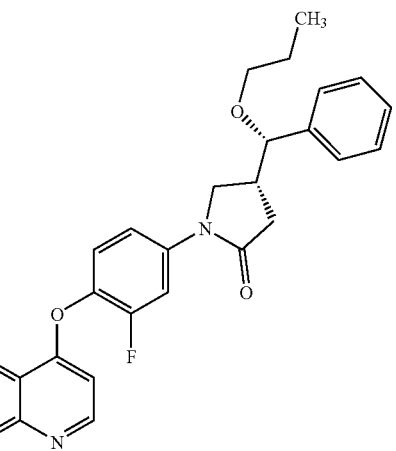 1-[4-(6,7-Dimethoxy-quinolin-4-yloxy)-3-fluoro-phenyl]-4-(phenyl propoxy-methyl)-pyrrolidin-2-one | $C_{31}H_{31}FN_2O_5$ | 530.22 | 531 |
| 69 | 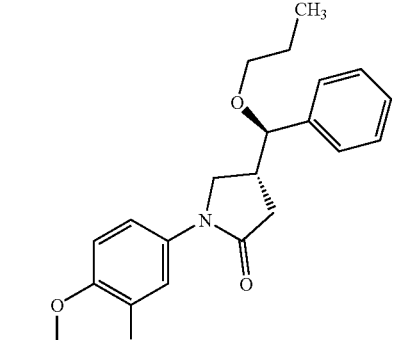 1-[4-(6,7-Dimethoxy-quinolin-4-yloxy)-3-fluoro-phenyl]-4-(phenyl-propoxy-methyl)-pyrrolidin-2-one | $C_{31}H_{31}FN_2O_5$ | 530.22 | 531 |

TABLE 5-continued

| Ex. | Structures | Mol Formula | Mol Weight | MS (MH+) |
|---|---|---|---|---|
| 70 | 4-Benzoyl-1-[4-(7-benzyloxy-6-methoxy-quinolin-4-yloxy)-3-fluoro-phenyl]-pyrrolidin-2-one | $C_{34}H_{27}FN_2O_5$ | 562.19 | 563 |
| 71 | 3-[4-(7-Benzyloxy-6-methoxy-quinolin-4-yloxy)-3-fluoro-phenyl)-1-phenyl-imidazolidine-2,4-dione | $C_{32}H_{24}FN_3O_5$ | 549.17 | 550 |
| 72 | 3-{3-Fluoro-4-[6-methoxy-7-(3-morpholin-4-yl-propoxy)-quinolin-4-yloxy]-phenyl}-1-isobutyl-imidazolidine-2,4-dione | $C_{30}H_{35}FN_4O_6$ | 566.25 | 567 |

TABLE 5-continued

| Ex. | Structures | Mol Formula | Mol Weight | MS (MH+) |
|---|---|---|---|---|
| 73 | 5-Benzyl-3-{3-fluoro-4-[6-methoxy-7-(3-morpholin-4-yl-propoxy)-quinolin-4-yloxy]-phenyl}-1-methyl-imidazolidine-2,4-dione | $C_{34}H_{35}FN_4O_6$ | 614.25 | 615 |
| 74 | 5-Benzyl-3-[4-(7-benzyloxy-6-methoxy-quinolin-4-yloxy)-3-fluoro-phenyl]-imidazolidine-2,4-dione | $C_{33}H_{26}FN_3O_5$ | 563.19 | 564 |
| 75 | 3-{3-Fluoro-4-[6-methoxy-7-(3-morpholin-4-yl-propoxy)-quinolin-4-yloxy]-phenyl}-1-phenethyl-imidazolidine-2,4-dione | $C_{34}H_{35}FN_4O_6$ | 614.25 | 615 |

TABLE 5-continued
| Ex. | Structures | Mol Formula | Mol Weight | MS (MH+) |
|---|---|---|---|---|
| 76 | 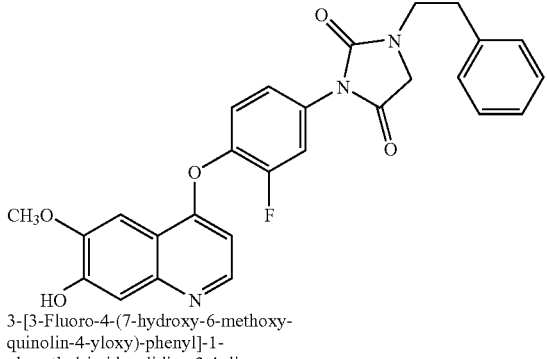 3-[3-Fluoro-4-(7-hydroxy-6-methoxy-quinolin-4-yloxy)-phenyl]-1-phenethyl-imidazolidine-2,4-dione | $C_{27}H_{22}FN_3O_5$ | 487.15 | 488 |
| 77 | 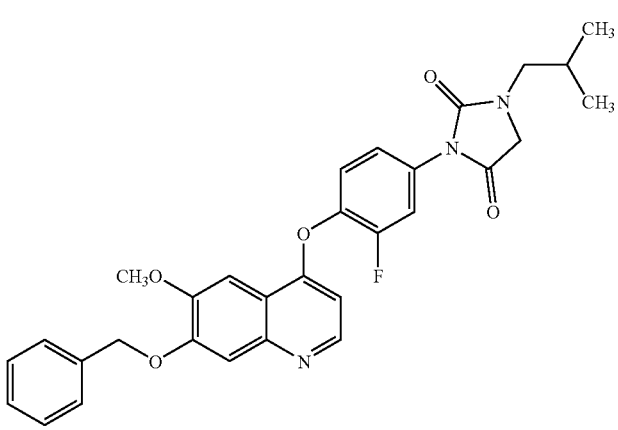 3-[4-(7-Benzyloxy-6-methoxy-quinolin-4-yloxy)-3-fluoro-phenyl)-1-isobutyl-imidazolidine-2,4-dione | $C_{30}H_{28}FN_3O_5$ | 529.20 | 530 |
| 78 | 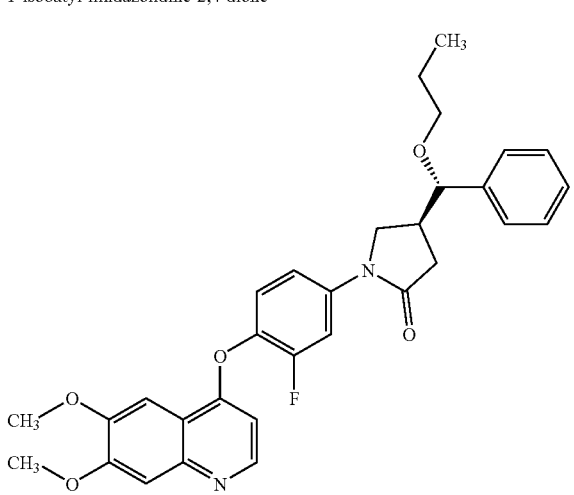 1-[4-(6,7-Dimethoxy-quinolin-4-yloxy)-3-fluoro-phenyl)-4-(phenyl-propoxy-methyl)-pyrrolidin-2-one | $C_{31}H_{31}FN_2O_5$ | 530.22 | 531 |

TABLE 5-continued

| Ex. | Structures | Mol Formula | Mol Weight | MS (MH+) |
|---|---|---|---|---|
| 79 | 1-[4-(6,7-Dimethoxy-quinolin-4-yloxy)-3-fluoro-phenyl]-4-(phenyl-propoxy-methyl)-pyrrolidin-2-one | C₃₁H₃₁FN₂O₅ | 530.22 | 531 |
| 80 | 4-Benzyl-1-{3-fluoro-4-[6-methoxy-7-(3-morpholin-4-yl-propoxy)-quinolin-4-yloxy]-phenyl}-pyrrolidin-2-one | C₃₄H₃₆FN₃O₅ | 585.26 | 586 |
| 81 | 4-Benzyl-1-[4-(6,7-dimethoxy-quinolin-4-yloxy)-3-fluoro-phenyl]-pyrrolidin-2-one | C₂₈H₂₅FN₂O₄ | 472.18 | 473 |

TABLE 5-continued
| Ex. | Structures | Mol Formula | Mol Weight | MS (MH+) |
|---|---|---|---|---|
| 82 | 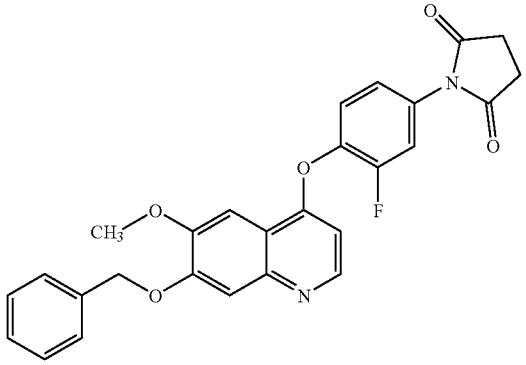<br>1-[4-(7-Benzyloxy-6-methoxy-quinolin-4-yloxy)-3-fluoro-phenyl]-pyrrolidine-2,5-dione | $C_{27}H_{21}FN_2O_5$ | 472.14 | 473 |
| 83 | 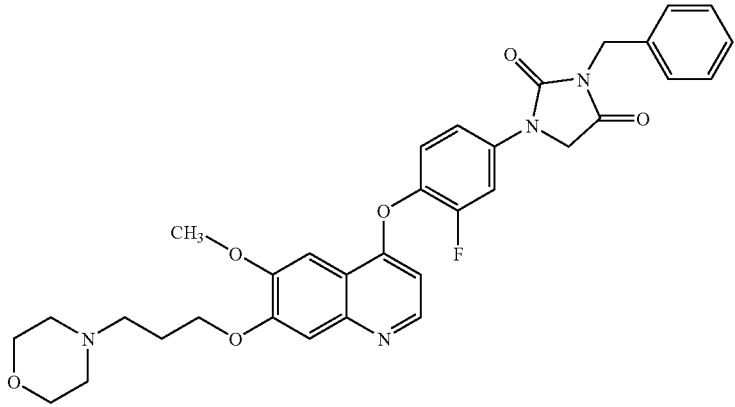<br>3-Benzyl-1-{3-fluoro-4-[6-methoxy-7-(3-morpholin-4-yl-propoxy)-quinolin-4-yloxy]-phenyl}-imidazolidine-2,4-dione | $C_{33}H_{33}FN_4O_6$ | 600.24 | 601 |
| 84 | 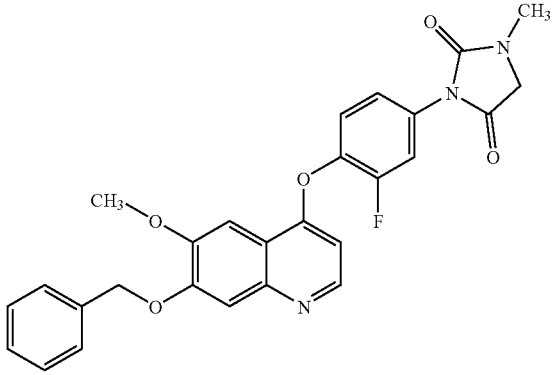<br>3-[4-(7-Benzyloxy-6-methoxy-quinolin-4-yloxy)-3-fluoro-phenyl]-1-methyl-imidazolidine-2,4-dione | $C_{27}H_{22}FN_3O_5$ | 487.15 | 488 |

TABLE 5-continued

| Ex. | Structures | Mol Formula | Mol Weight | MS (MH+) |
|---|---|---|---|---|
| 85 | 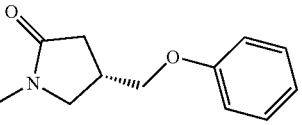<br>1-[4-(6,7-Dimethoxy-quinolin-4-yloxy)-3-fluoro-phenyl]-4-phenoxymethyl-pyrrolidin-2-one | $C_{28}H_{25}FN_2O_5$ | 488.17 | 489 |
| 86 | 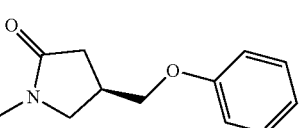<br>1-[4-(6,7-Dimethoxy-quinolin-4-yloxy)-3-fluoro-phenyl]-4-phenoxymethyl-pyrrolidin-2-one | $C_{28}H_{25}FN_2O_5$ | 488.17 | 489 |
| 88 | 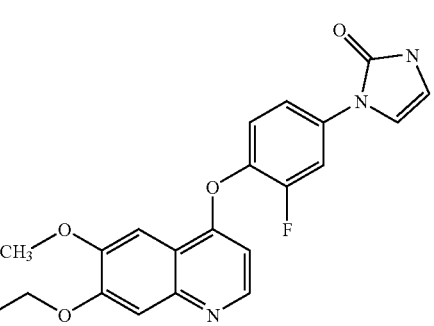<br>1-{3-Fluoro-4-[6-methoxy-7-(3-morpholin-4-yl-propoxy)-quinolin-4-yloxy]-phenyl}-1,3-dihydro-imidazol-2-one | $C_{26}H_{27}FN_4O_5$ | 494.20 | 495 |
| 89 | 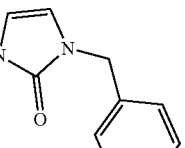<br>1-Benzyl-3-[4-(6,7-dimethoxy-quinolin-4-yloxy)-phenyl]-1,3-dihydro-imidazol-2-one | $C_{27}H_{23}N_3O_4$ | 453.17 | 454 |

TABLE 5-continued
| Ex. | Structures | Mol Formula | Mol Weight | MS (MH+) |
|---|---|---|---|---|
| 90 | 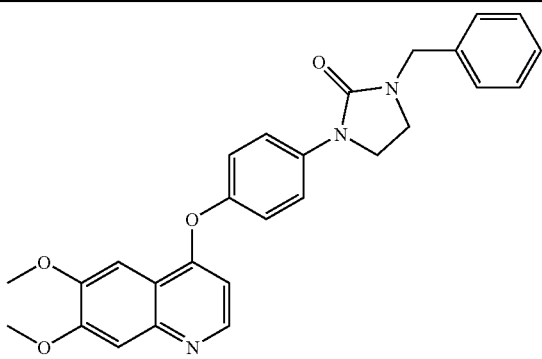<br>1-(4-((6,7-bis(methoxy)-4-quinolinyl)oxy)phenyl)-3-(phenylmethyl)-2-imidazolidinone | $C_{27}H_{25}N_3O_4$ | 455.18 | 456 |
Other compounds included in this invention are set forth in Tables 6-8 below.
TABLE 6
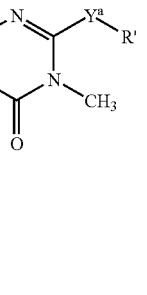
| # | $R^{10}$ | $Y^a$ | R' |
|---|---|---|---|
| 91. | methoxy | NH | 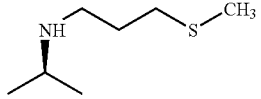 |
| 92. | methoxy | 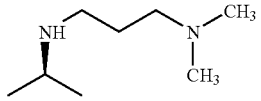 | phenyl |
| 93. | methoxy | 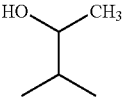 | phenyl |
| 94. | methoxy |  | phenyl |

TABLE 6-continued

| # | R¹⁰ | Yᵃ | R' |
|---|---|---|---|
| 95. | methoxy | NH | (structure: N-methyl cyclopentane carboxamide with ethyl-NHCH₃) |
| 96. | methoxy | NH | (structure: N-methyl cyclohexane carboxamide with propyl-N(CH₃)₂) |
| 97. | methoxy | NH | (structure: isobutyramide with ethyl-N(CH₃)₂) |

TABLE 7

| # | R¹⁰ | Yᵃ | R' |
|---|---|---|---|
| 98. | methoxy | NH | phenyl |
| 99. | methoxy | CH(CH₂OH) | phenyl |

TABLE 8

| # | R¹⁰ | W | A | Y | R |
|---|---|---|---|---|---|
| 100. | methoxy | 2,5-dimethylphenyl | 1,4-dimethyl-pyrazol-5(1H)-one | CH₂ | phenyl |
| 101. | methoxy | 2,5-dimethylpyridinyl | 2,5-dimethyl-3-methyl-pyrimidin-4(3H)-one | NH | phenyl |
| 102. | methoxy | 2,5-dimethylpyridinyl | 2,5-dimethyl-3-methyl-pyrimidin-4(3H)-one | CH₂ | phenyl |

TABLE 9

| Ex. | Structure | Mol Formula | Mol Weight | MS (MH+) |
|---|---|---|---|---|
| 103 | 5-(4-((6,7-bis(methyloxy)-4-quinolinyl)oxy)-3-fluorophenyl)-2-(((3-hydroxypropyl)amino)(phenyl)-methyl)-3-methyl-4(3H)-pyrimidinone | C₃₂H₃₁FN₄O₅ | 570 | 571 |

TABLE 9-continued

| Ex. | Structure | Mol Formula | Mol Weight | MS (MH+) |
|---|---|---|---|---|
| 104 | 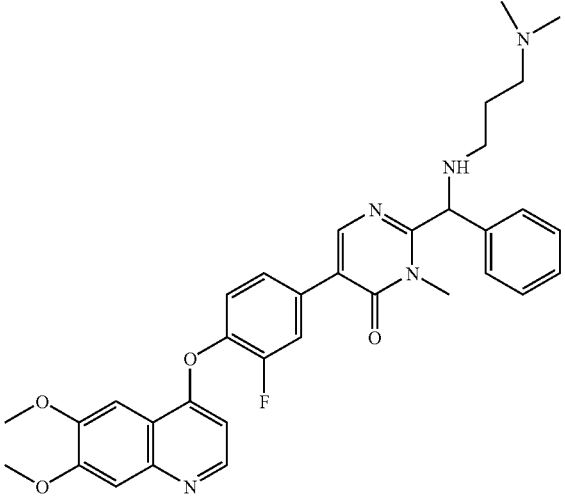  5-(4-((6,7-bis(methyloxy)-4-quinolinyl)oxy)-3-fluorophenyl)-2-(((3-(dimethylamino)propyl)amino)-(phenyl)methyl)-3-methyl-4(3H)-pyrimidinone | $C_{34}H_{36}FN_5O_4$ | 597 | 598 |
| 105 | 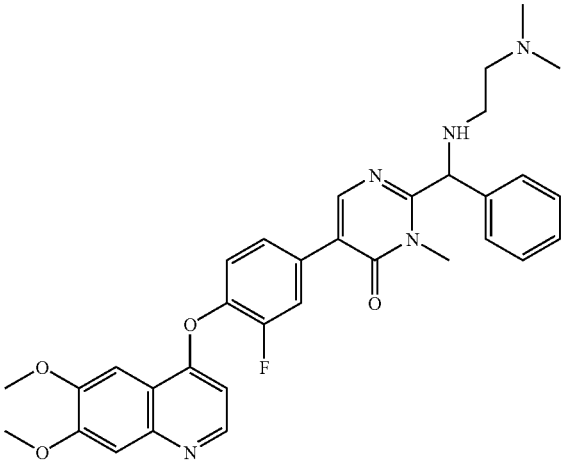  5-(4-((6,7-bis(methyloxy)-4-quinolinyl)oxy)-3-fluorophenyl)-2-(((2-(dimethylamino)ethyl)amino)-(phenyl)methyl)-3-methyl-4(3H)-pyrimidinone | $C_{33}H_{34}FN_5O_4$ | 583 | 584 |
| 106 | 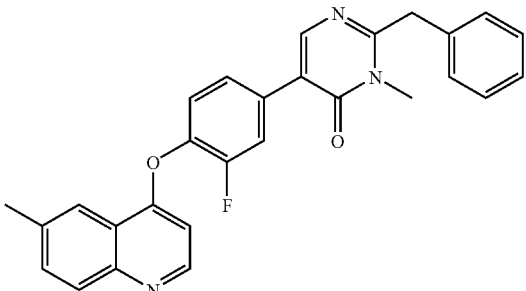  5-(3-fluoro-4-((6-methyl-4-quinolinyl)oxy)phenyl)-3-methyl-2-(phenylmethyl)-4(3H)-pyrimidinone | $C_{28}H_{22}FN_3O_2$ | 451 | 452 |

TABLE 9-continued
| Ex. | Structure | Mol Formula | Mol Weight | MS (MH+) |
|---|---|---|---|---|
| 107 | 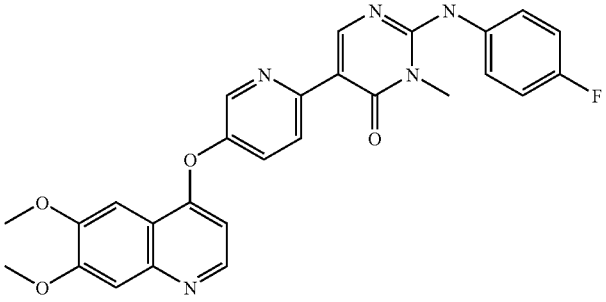<br>5-(5-((6,7-bis(methyloxy)-4-quinolinyl)oxy)-2-pyridinyl)-2-((4-fluorophenyl)amino)-3-methyl-4(3H)-pyrimidinone | $C_{27}H_{22}FN_5O_4$ | 499 | 500 |
| 108 | 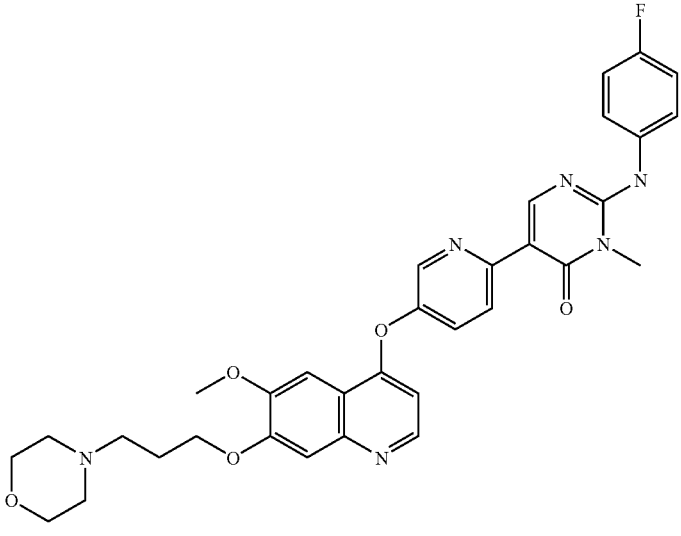<br>2-((4-fluorophenyl)amino)-3-methyl-5-(5-((6-(methyloxy)-7-((3-(4-morpholinyl)propyl)oxy)-4-quinolinyl)oxy)-2-pyridinyl)-4(3H)-pyrimidinone | $C_{33}H_{33}FN_6O_5$ | 612 | 613 |

TABLE 9-continued
| Ex. | Structure | Mol Formula | Mol Weight | MS (MH+) |
|---|---|---|---|---|
| 109 | 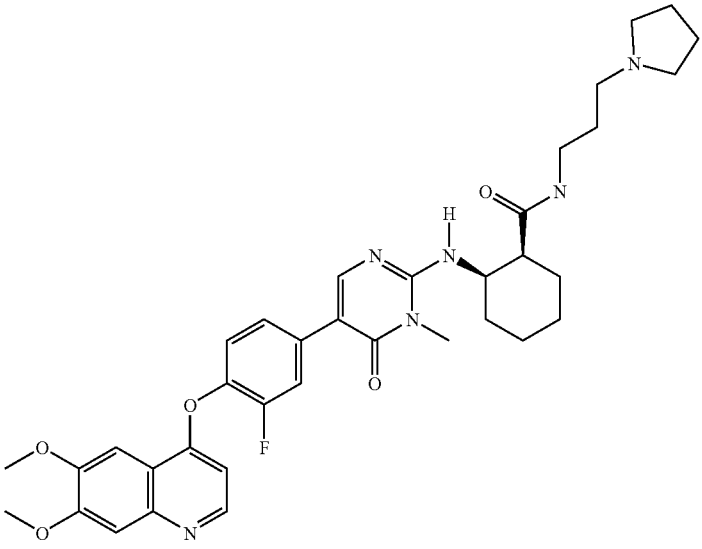 (1S,2R)-2-((5-(4-((6,7-bis(methyloxy)-4-quinolinyl)oxy)-3-fluorophenyl)-1-methyl-6-oxo-1,6-dihydro-2-pyrimidinyl)amino)-N-(3-(1-pyrrolidinyl)propyl)cyclohexanecarboxamide | $C_{36}H_{43}FN_6O_5$ | 658 | 659 |
| 110 | 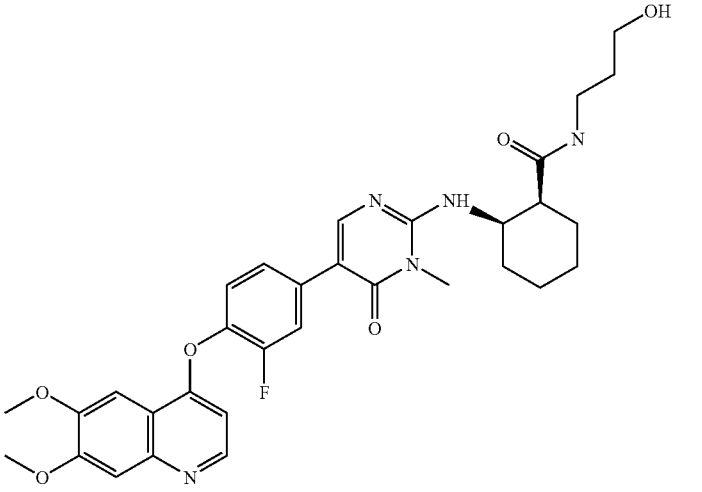 (1S,2R)-2-((5-(4-((6,7-bis(methyloxy)-4-quinolinyl)oxy)-3-fluorophenyl)-1-methyl-6-oxo-1,6-dihydro-2-pyrimidinyl)amino)-N-(3-hydroxypropyl)cyclohexanecarboxamide | $C_{32}H_{36}FN_5O_6$ | 605 | 606 |

TABLE 9-continued
| Ex. | Structure | Mol Formula | Mol Weight | MS (MH+) |
|---|---|---|---|---|
| 111 | 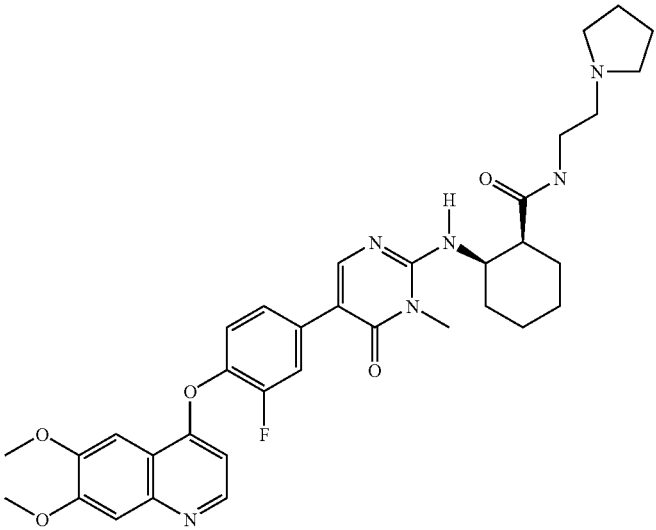<br>(1S,2R)-2-((5-(4-((6,7-bis(methyloxy)-4-quinolinyl)oxy)-3-fluorophenyl)-1-methyl-6-oxo-1,6-dihydro-2-pyrimidinyl)amino)-N-(2-(1-pyrrolidinyl)ethyl)-cyclohexanecarboxamide | $C_{35}H_{41}FN_6O_5$ | 644 | 645 |
| 112 | 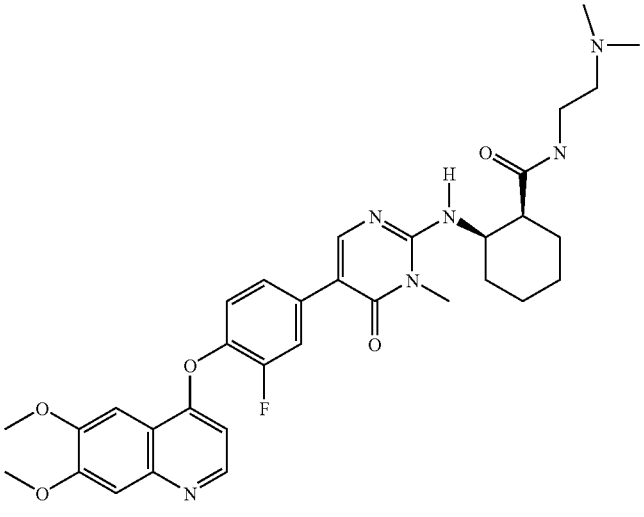<br>(1S,2R)-2-((5-(4-((6,7-bis(methyloxy)-4-quinolinyl)oxy)-3-fluorophenyl)-1-methyl-6-oxo-1,6-dihydro-2-pyrimidinyl)amino)-N-(2-(dimethylamino)ethyl)cyclohexane carboxamide | $C_{33}H_{39}FN_6O_5$ | 618 | 619 |

TABLE 9-continued

| Ex. | Structure | Mol Formula | Mol Weight | MS (MH+) |
|---|---|---|---|---|
| 113 | 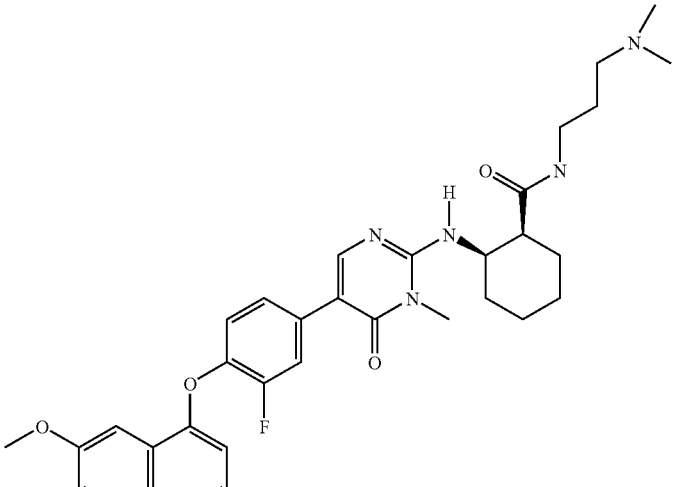<br>(1S,2R)-2-((5-(4-((6,7-bis(methyloxy)-4-quinolinyl)oxy)-3-fluorophenyl)-1-methyl-6-oxo-1,6-dihydro-2-pyrimidinyl)amino)-N-(3-(dimethylamino)propyl)cyclohexane carboxamide | $C_{34}H_{41}FN_6O_5$ | 632 | 633 |
| 114 | 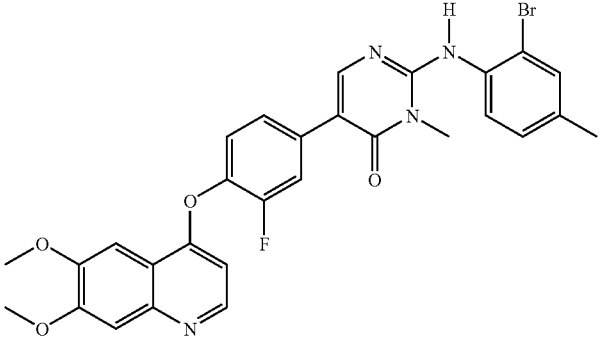<br>5-(4-((6,7-bis(methyloxy)-4-quinolinyl)oxy)-3-fluorophenyl)-2-((2-bromo-4-methylphenyl)amino)-3-methyl-4(3H)-pyrimidinone | $C_{29}H_{24}BrFN_4O_4$ | 591 | 592 |
| 115 | 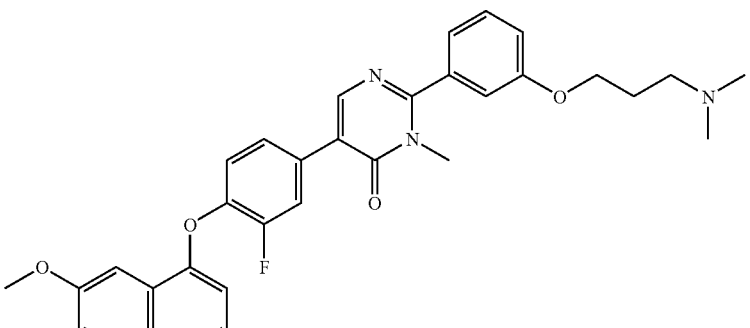<br>5-(4-((6,7-bis(methyloxy)-4-quinolinyl)oxy)-3-fluorophenyl)-2-(3-((3-(dimethylamino)propyl)oxy)phenyl)-3-methyl-4(3H)-pyrimidinone | $C_{33}H_{33}FN_4O_5$ | 584 | 585 |

TABLE 9-continued

| Ex. | Structure | Mol Formula | Mol Weight | MS (MH+) |
|---|---|---|---|---|
| 116 | 1-((3,4-dimethylphenyl)methyl)-3-(3-fluoro-4-((6-(methyloxy)-7-((3-(4-morpholinyl)propyl)oxy)-4-quinolinyl)oxy)phenyl)-2,4-imidazolidinedione | $C_{35}H_{37}FN_4O_6$ | 628 | 629 |
| 117 | 3-(3-fluoro-4-((6-(methyloxy)-7-((3-(4-morpholinyl)propyl)oxy)-4-quinolinyl)oxy)phenyl)-1-((4-(methyloxy)phenyl)methyl-2,4-imidazolidinedione | $C_{34}H_{35}FN_4O_7$ | 630 | 631 |
| 118 | 1-((3-bromophenyl)methyl)-3-(3-fluoro-4-((6-(methyloxy)-7-((3-(4- | $C_{33}H_{32}BrFN_4O_6$ | 679 | 680 |

TABLE 9-continued

| Ex. | Structure | Mol Formula | Mol Weight | MS (MH+) |
|---|---|---|---|---|
| | morpholinyl)propyl)oxy)-4-quinolinyl)oxy)phenyl)-2,4-imidazolidinedione | | | |
| 119 | 1-((2-chlorophenyl)methyl)-3-(3-fluoro-4-((6-(methyloxy)-7-((3-(4-morpholinyl)propyl)oxy)-4-quinolinyl)oxy)phenyl)-2,4-imidazolidinedione | $C_{32}H_{32}ClFN_4O_5$ | 634 | 635 |
| 120 | 3-(3-fluoro-4-((6-(methyloxy)-7-((3-(4-morpholinyl)propyl)oxy)-4-quinolinyl)oxy)phenyl)-1-((3-(methyloxy)phenyl)methyl)-2,4-imidazolidinedione | $C_{34}H_{35}FN_4O_7$ | 630 | 631 |
| 121 | 3-(3-fluoro-4-((6-(methyloxy)-7-((3-(4-morpholinyl)propyl)oxy)-4-quinolinyl)oxy)phenyl)-1-((3- | $C_{34}H_{35}FN_4O_6$ | 614 | 615 |

TABLE 9-continued

| Ex. | Structure | Mol Formula | Mol Weight | MS (MH+) |
|---|---|---|---|---|
| | methylphenyl)methyl)-2,4-imidazolidinedione | | | |
| 122 | 1-((3,4-dichlorophenyl)methyl)-3-(3-fluoro-4-((6-(methyloxy)-7-((3-(4-morpholinyl)propyl)oxy)-4-quinolinyl)oxy)phenyl)-2,4-imidazolidinedione | C₃₃H₃₁Cl₂FN₄O₆ | 669 | 670 |
| 123 | 3-(3-fluoro-4-((6-(methyloxy)-7-((3-(4-morpholinyl)propyl)oxy)-4-quinolinyl)oxy)phenyl)-1-((3-(trifluoromethyl)phenyl)methyl)-2,4-imidazolidinedione | C₃₄H₃₂F₄N₄O₆ | 668 | 669 |
| 124 | 5-(5-((6,7-bis(methyloxy)-4-quinolinyl)oxy)-2-pyridinyl)-3- | C₂₇H₂₃N₅O₄ | 481 | 482 |

TABLE 9-continued

| Ex. | Structure | Mol Formula | Mol Weight | MS (MH+) |
|---|---|---|---|---|
| | methyl-2-(phenylamino)-4(3H)-pyrimidinone | | | |
| 125 | N-((S)-(5-(4-((6,7-bis(methyloxy)-4-quinolinyl)oxy)-3-fluorophenyl)-1-methyl-6-oxo-1,6-dihydro-2-pyrimidinyl)(phenyl)methyl)-3-(methylthio)propanamide | $C_{33}H_{31}FN_4O_5S$ | 614 | 615 |
| 126 | 1-(1,1'-biphenyl-3-ylmethyl)-3-(3-fluoro-4-((6-(methyloxy)-7-((3-(4-morpholinyl)propyl)oxy)-4-quinolinyl)oxy)phenyl)-2,4-imidazolidinedione | $C_{39}H_{37}FN_4O_6$ | 676 | 677 |
| 127 | 3-(3-fluoro-4-((6-(methyloxy)-7-((3-(4-morpholinyl)propyl)oxy)-4-quinolinyl)oxy)phenyl)-1-(1-naphthalenylmethyl)-2,4-imidazolidinedione | $C_{37}H_{35}FN_4O_6$ | 650 | 651 |

TABLE 9-continued

| Ex. | Structure | Mol Formula | Mol Weight | MS (MH+) |
|---|---|---|---|---|
| 128 | (5R)-3-(3-fluoro-4-((6-(methyloxy)-7-((3-(4-morpholinyl)propyl)oxy)-4-quinolinyl)oxy)phenyl)-5-phenyl-2,4-imidazolidinedione | $C_{32}H_{31}FN_4O_6$ | 586 | 587 |
| 129 | (5S)-3-(3-fluoro-4-((6-(methyloxy)-7-((3-(4-morpholinyl)propyl)oxy)-4-quinolinyl)oxy)phenyl)-5-phenyl-2,4-imidazolidinedione | $C_{32}H_{31}FN_4O_6$ | 586 | 587 |
| 130 | (4R)-3-(4-((6,7-bis(methyloxy)-4-quinolinyl)oxy)-3-fluorophenyl)-4-(phenylmethyl)-1,3-oxazolidin-2-one | $C_{27}H_{23}FN_2O_5$ | 473 | 474 |

TABLE 9-continued

| Ex. | Structure | Mol Formula | Mol Weight | MS (MH+) |
|---|---|---|---|---|
| 131 | 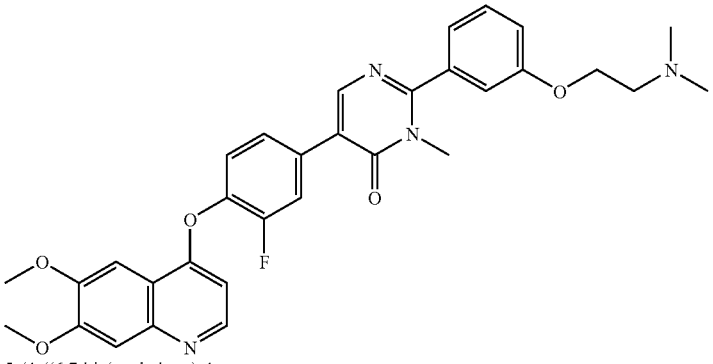<br>5-(4-((6,7-bis(methyloxy)-4-quinolinyl)oxy)-3-fluorophenyl)-2-(3-((2-(dimethylamino)ethyl)oxy)phenyl)-3-methyl-4(3H)-pyrimidinone | $C_{32}H_{31}FN_4O_5$ | 570 | 571 |
| 132 | 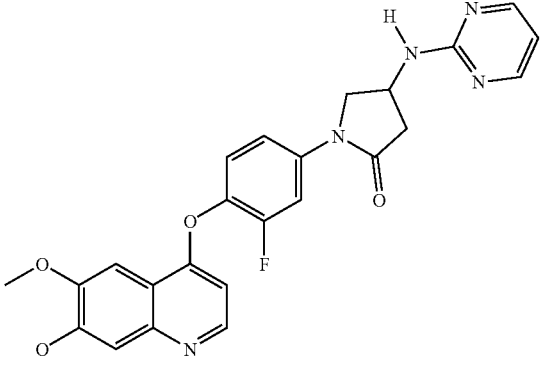<br>1-(4-((6,7-bis(methyloxy)-4-quinolinyl)oxy)-3-fluorophenyl)-4-(2-pyrimidinylamino)-2-pyrrolidinone | $C_{25}H_{22}FN_5O_4$ | 475 | 476 |
| 133 | 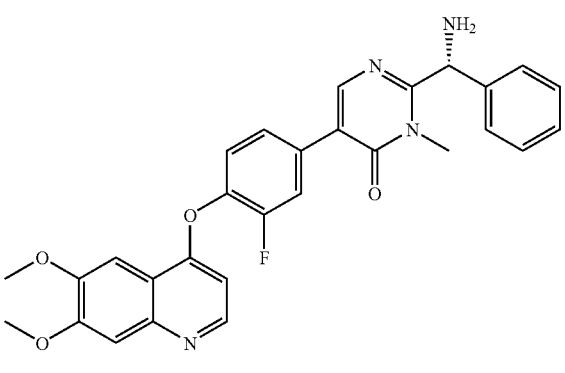<br>2-((R)-amino(phenyl)methyl)-5-(4-((6,7-bis(methyloxy)-4-quinolinyl)oxy)-3-fluorophenyl)-3-methyl-4(3H)-pyrimidinone | $C_{29}H_{25}FN_4O_4$ | 512 | 513 |

TABLE 9-continued

| Ex. | Structure | Mol Formula | Mol Weight | MS (MH+) |
|---|---|---|---|---|
| 134 | 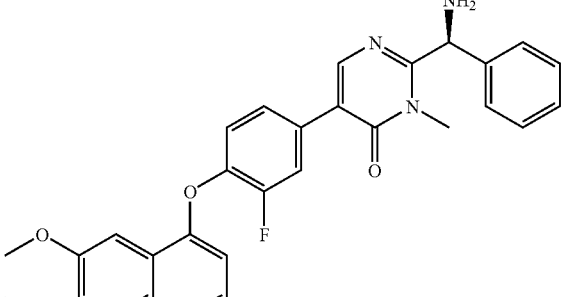 2-((S)-amino(phenyl)methyl)-5-(4-((6,7-bis(methyloxy)-4-quinolinyl)oxy)-3-fluorophenyl)-3-methyl-4(3H)-pyrimidinone | $C_{29}H_{25}FN_4O_4$ | 512 | 513 |
| 135 | 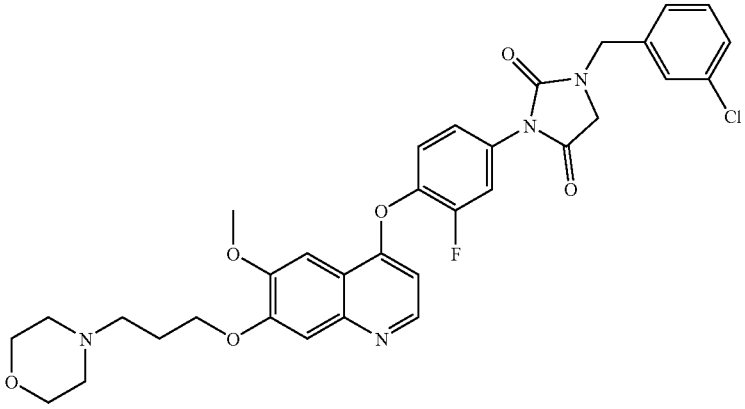 1-((3-chlorophenyl)methyl)-3-(3-fluoro-4-((6-(methyloxy)-7-((3-(4-morpholinyl)propyl)oxy)-4-quinolinyl)oxy)phenyl)-2,4-imidazolidinedione | $C_{33}H_{32}ClFN_4O_6$ | 634 | 635 |
| 136 | 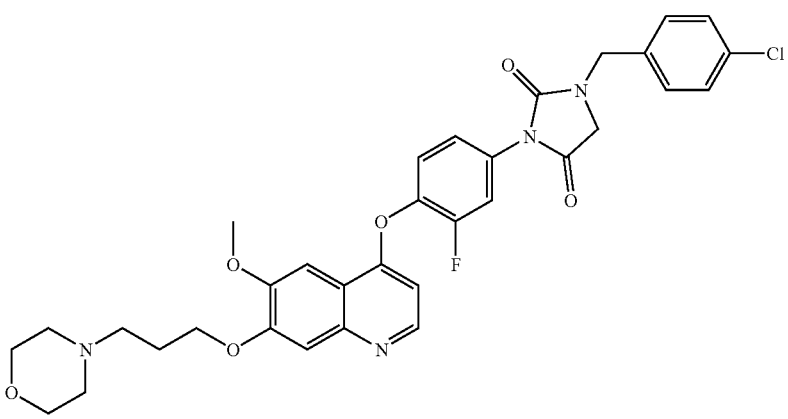 1-((4-chlorophenyl)methyl)-3-(3-fluoro-4-((6-(methyloxy)-7-((3-(4-morpholinyl)propyl)oxy)-4-quinolinyl)oxy)phenyl)-2,4-imidazolidinedione | $C_{33}H_{32}ClFN_4O_6$ | 634 | 635 |

TABLE 9-continued

| Ex. | Structure | Mol Formula | Mol Weight | MS (MH+) |
|---|---|---|---|---|
| 137 | 5-(4-((6,7-bis(methyloxy)-4-quinolinyl)oxy)-3-fluorophenyl)-2-(3-hydroxyphenyl)-3-methyl-4(3H)-pyrimidinone | $C_{28}H_{22}FN_3O_5$ | 499 | 500 |
| 138 | N-(5-(4-((6,7-bis(methyloxy)-4-quinolinyl)oxy)-3-fluorophenyl)-1-methyl-6-oxo-1,6-dihydro-2-pyrimidinyl)(phenyl)methyl)-4-methyl-1-piperazinecarboxamide | $C_{35}H_{35}FN_6O_5$ | 638 | 639 |
| 139 | 5-(5-((6,7-bis(methyloxy)-4-quinolinyl)oxy)-2-pyridinyl)-3-methyl-2-(phenylmethyl)-4(3H)-pyrimidinone | $C_{28}H_{24}N_4O_4$ | 480 | 481 |

TABLE 9-continued

| Ex. | Structure | Mol Formula | Mol Weight | MS (MH+) |
|---|---|---|---|---|
| 140 | 3-(3-fluoro-4-((6-(methyloxy)-7-((3-(4-morpholinyl)propyl)oxy)-4-quinolinyl)oxy)phenyl)-1-((4-fluorophenyl)methyl)-2,4-imidazolidinedione | $C_{33}H_{32}F_2N_4O_6$ | 618 | 619 |
| 141 | N'-((5-(4-((6,7-bis(methyloxy)-4-quinolinyl)oxy)-3-fluorophenyl)-1-methyl-6-oxo-1,6-dihydro-2-pyrimidinyl)(phenyl)methyl)-N,N-dimethylurea | $C_{32}H_{30}FN_5O_5$ | 583 | 584 |
| 142 | 5-(4-((6,7-bis(methyloxy)-4-quinolinyl)oxy)phenyl)-1-(phenylmethyl)-2(1H)-pyrimidinone | $C_{28}H_{23}N_3O_4$ | 465 | 466 |

TABLE 9-continued

| Ex. | Structure | Mol Formula | Mol Weight | MS (MH+) |
|---|---|---|---|---|
| 143 | N-((5-(4-((6,7-bis(methyloxy)-4-quinolinyl)oxy)-3-fluorophenyl)-1-methyl-6-oxo-1,6-dihydro-2-pyrimidinyl)(phenyl)methyl)-3-(methylthio)propanamide | $C_{33}H_{31}FN_4O_5S$ | 614 | 615 |
| 144 | N-((5-(4-((6,7-bis(methyloxy)-4-quinolinyl)oxy)-3-fluorophenyl)-1-methyl-6-oxo-1,6-dihydro-2-pyrimidinyl)(phenyl)methyl)propanamide | $C_{32}H_{29}FN_4O_5$ | 568 | 569 |
| 145 | 1-(4-((6,7-bis(methyloxy)-4-quinolinyl)oxy)phenyl)-3-(phenylmethyl)-1H-pyrazol-5-ol | $C_{27}H_{23}N_3O_4$ | 453 | 454 |

TABLE 9-continued
| Ex. | Structure | Mol Formula | Mol Weight | MS (MH+) |
|---|---|---|---|---|
| 146 | 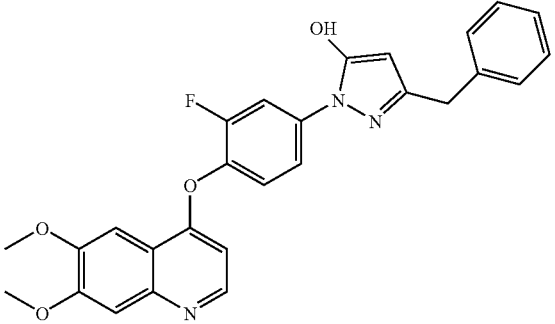<br>1-(4-((6,7-bis(methyloxy)-4-quinolinyl)oxy)-3-fluorophenyl)-3-(phenylmethyl)-1H-pyrazol-5-ol | $C_{27}H_{22}FN_3O_4$ | 471 | 472 |
| 147 | 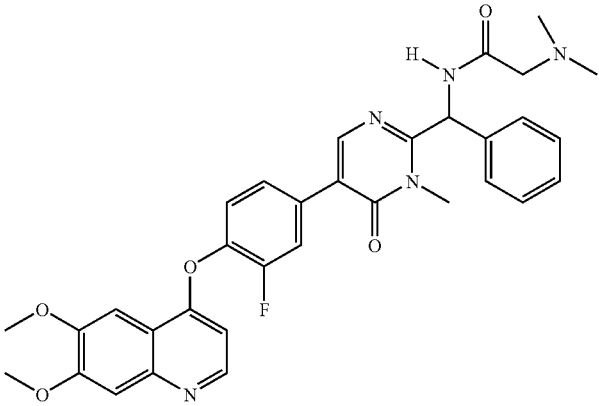<br>N-1-((5-(4-((6,7-bis(methyloxy)-4-quinolinyl)oxy)-3-fluorophenyl)-1-methyl-6-oxo-1,6-dihydro-2-pyrimidinyl)(phenyl)methyl)-N-2-N-2-dimethylglycinamide | $C_{33}H_{32}FN_5O_5$ | 597 | 598 |

The following additional compounds can be synthesized using procedures known to those skilled in the art.
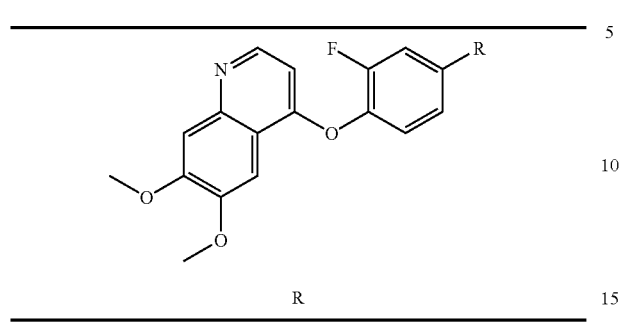
| R |
|---|
| 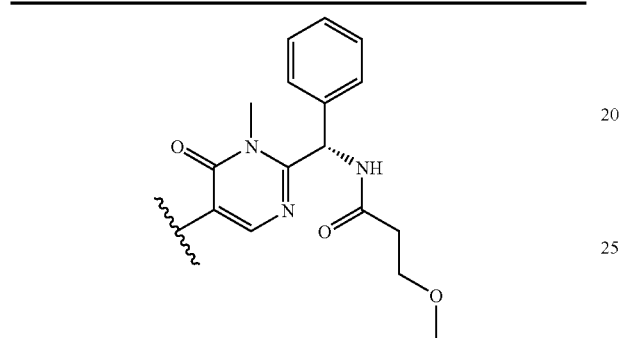 |
| 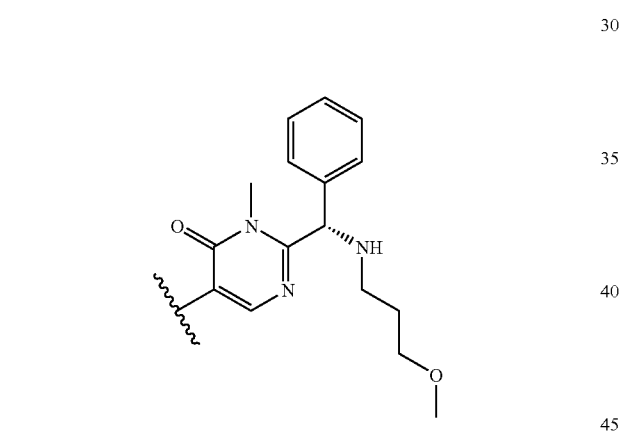 |
| 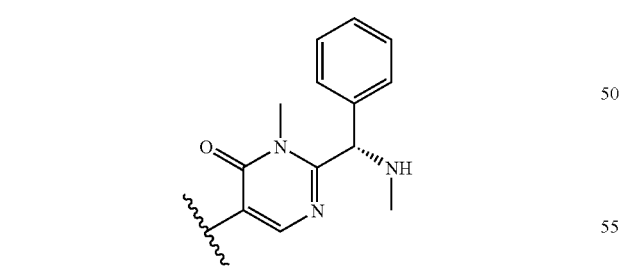 |
| 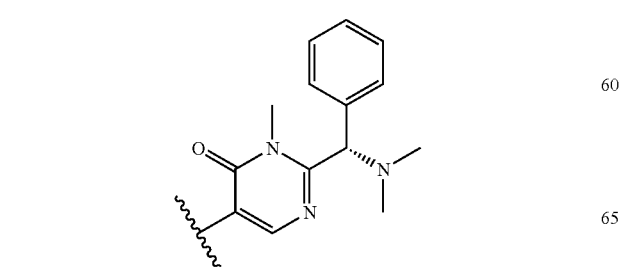 |
-continued
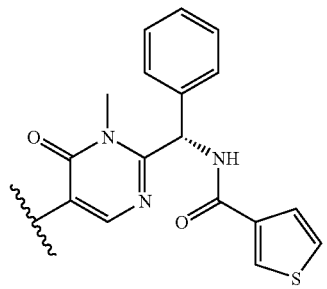
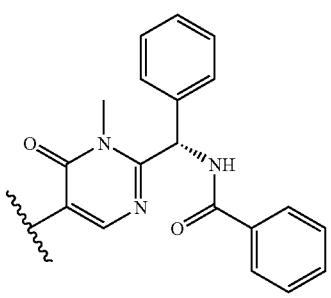
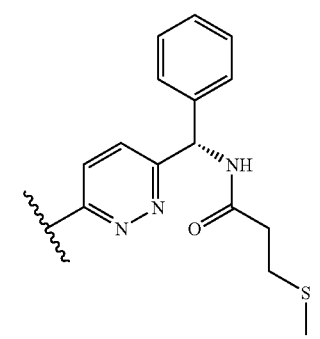
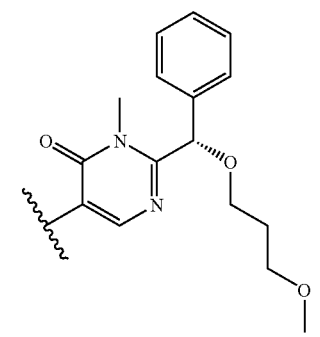
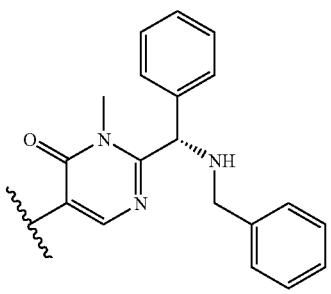

| 205 | 206 |
|---|---|
| -continued | -continued |
| 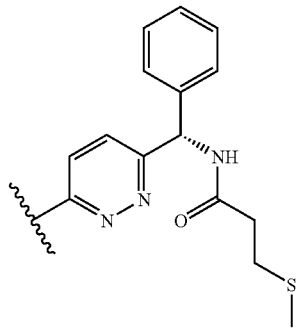 | 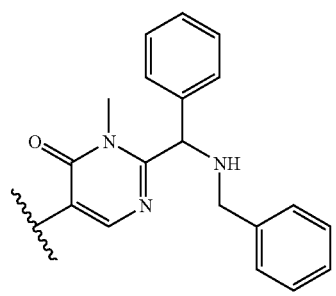 |
| 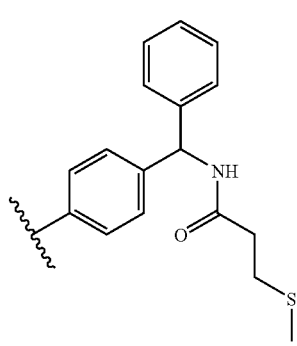 | 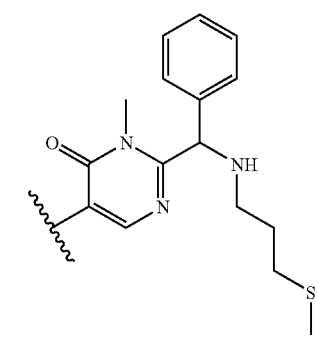 |
| 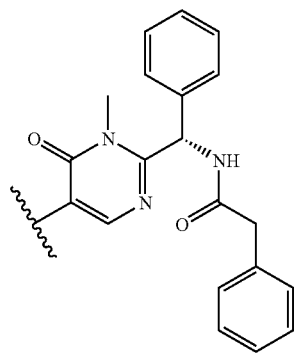 | 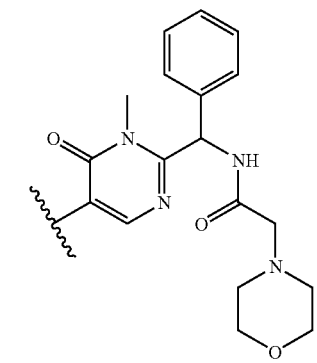 |
| 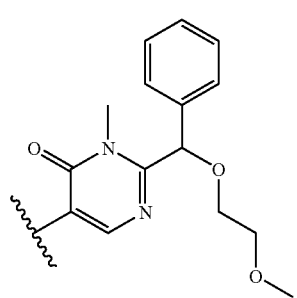 | 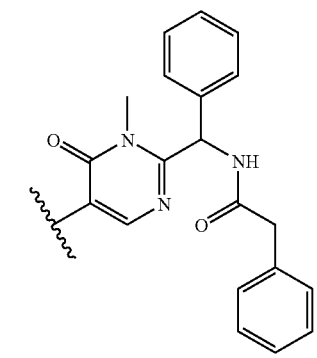 |

-continued

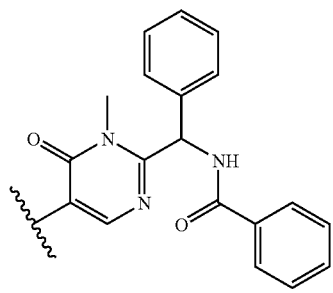

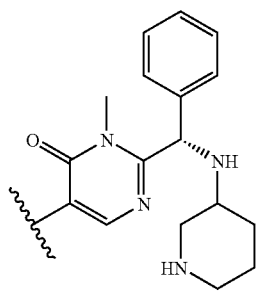

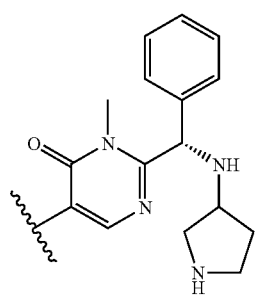

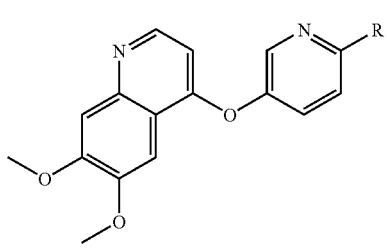

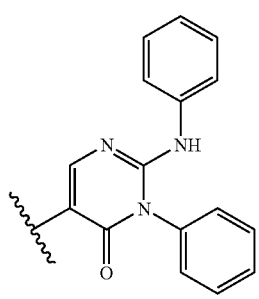

-continued

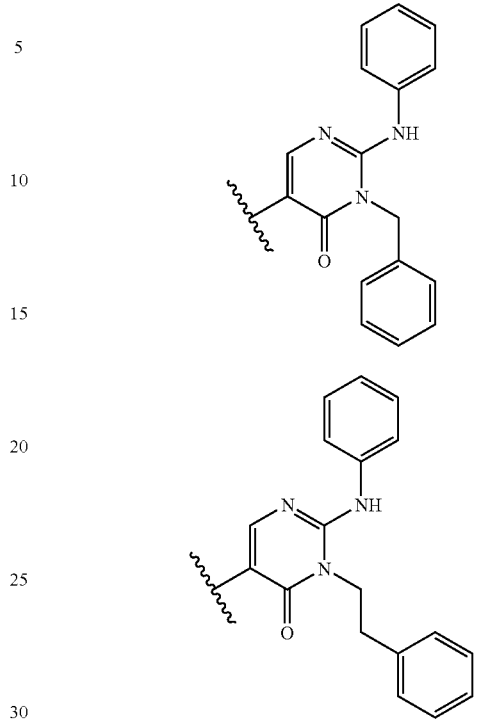

Although the pharmacological properties of the compounds of Formulas I-V vary with structural change, in general, activity possessed by compounds of Formulas I-V may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed inhibition of c-Met kinase at doses less than 2 µM.

Biological Testing

The efficacy of the compounds of the invention as inhibitors of HGF related activity is demonstrated as follows.

c-Met Receptor Assay

Cloning, Expression and Purification of c-Met Kinase Domain

A PCR product covering residues 1058-1365 of c-Met (c-Met kinase domain) is generated from Human Liver QuickClone™ cDNA (Invitrogen) using forward primer 5'-ATTGACGGATCCATGCTAAATCCA-GAGCTGGTCCAGGCA-3' (SEQ ID NO. 1) and reverse primer 5'-ACAACAGAATTCAATACGGAGCGACA-CATTTTACGTT-3' (SEQ ID NO. 2). The PCR product is cloned into a modified pFastBac1 expression vector (harboring the gene for *S. japonicum* glutathione S-transferase immediately upstream of the multiple cloning site) using standard molecular biological techniques. The GST-c-Met kinase domain fusion (GST-Met) gene is transposed into full-length baculovirus DNA using the BacToBac™ system (Invitrogen). High5 cells are infected with the recombinant baculovirus for 72 h at 27° C. The infected cells are harvested by centrifugation and the pellet is stored at −80° C. The pellet is resuspended in buffer A (50 mM HEPES, pH 8.0, 0.25 M NaCl, 10 mM 2-mercaptoethanol, 10% (w/v) glycerol, 0.5% (v/v) protease inhibitor cocktail (Sigma P8340), stirred at 4° C. to homogeneity, and the cells are disrupted by microfluidization (Microfluidics) at 10,000 psi. The resulting lysate is centrifuged at 50,000×g for 90 min at 4° C., and the supernatant is adsorbed onto 10 mL of glutathione Sepharose™ 4B (Amersham) by batch method. The slurry is rocked gently overnight at 4° C. The glutathione resin is harvested by centrifugation and washed three times with 40 mL buffer A by batch method. The resin is washed three times with buffer B (buffer A adjusted to 0.1 M NaCl, less protease inhibitors). The protein is eluted with buffer B containing 25 mM reduced glutathione. Eluted fractions are analyzed by SDS-PAGE and concentrated to <10 mL (~10 mg/mL total protein). The concentrated protein is separated by Superdex™ 200 (Amersham) size exclusion chromatography in buffer C (25 mM Tris, pH 7.5, 0.1 M NaCl, 10 mM 2-mercaptoethanol, 10% glycerol). The fractions are analyzed by SDS-PAGE and the appropriate fractions are pooled and concentrated to ~1 mg/mL. The protein is aliquotted and stored at −80° C.

Alternative Purification of human GST-cMET from Baculovirus Cells

Baculovirus cells are broken in 5× (volume/weight) of Lysis Buffer (50 mM HEPES, pH 8.0, 0.25 M NaCl, 5 mM mercaptoethanol, 10% glycerol plus Complete Protease Inhibitors (Roche (#10019600), 1 tablet per 50 mL buffer). The lysed cell suspension is centrifuged at 100,000×g (29,300 rpm) in a Beckman ultracentrifuge Ti45 rotor for 1 h. The supernatant is incubated with 10 ml of Glutathione Sepharose 4B from Amersham Biosciences (#27-4574-01). Incubation is carried out overnight in a cold room (approximately 8° C.). The resin and supernatant is poured into an appropriately sized disposable column and the flow through supernatant was collected. The resin is washed with 10 column volumes (100 mL) of Lysis Buffer. The GST-cMET is eluted with 45 mL of 10 mM Glutathione (Sigma #G-4251) in Lysis Buffer. The elution is collected as 15 mL fractions. Aliquots of the elution fractions are run on SDS PAGE (12% Tris Glycine gel, Invitrogen, #EC6005BOX). The gel is stained with 0.25% Coomassie Blue stain. Fractions with GST-cMET are concentrated with a Vivaspin 20 mL Concentrator (#VS2002; 10,00 MW cutoff) to a final volume less than 2.0 ml. The concentrated GST-cMET solution is applied to a Superdex 75 16/60 column (Amersham Biosciences #17-1068-01) equilibrated with 25 mM Tris, pH 7.5, 100 mM NaCl, 10 mM mercaptoethanol, 10% glycerol. The GST-cMET is eluted with an isocratic run of the above buffer, with the eluent collected in 1.0 mL fractions. Fractions with significant $OD_{280}$ readings are run on another 12% Tris Glycine gel. The peak tubes with GST-cMET are pooled and the $OD_{280}$ is read with the column buffer listed above as the blank buffer.

Phosphorylation of the purified GST-cMET is performed by incubating the protein for 3 h at RT with the following:

| | Final concentration |
|---|---|
| a) 100 mM ATP (Sigma #A7699) | 25 mM |
| b) 1.0 M $MgCl_2$ (Sigma #M-0250) | 100 mM |
| c) 200 mM Sodium Orthovanadate (Sigma #S-6508) | 15 mM |

-continued

| | Final concentration |
|---|---|
| d) 1.0 M Tris-HCl, pH 7.00 (in house) | 50 mM |
| e) $H_2O$ | |
| f) GST-cMET | 0.2-0.5 mg/mL |

After incubation, the solution is concentrated in a Vivaspin 20 mL Concentrator to a volume less than 2.00 mL. The solution is applied to the same Superdex 75 16/60 column used above after re-equilibration. The GST-cMET is eluted as described above. The elution fractions corresponding to the first eluted peak on the chromatogram are run on a 12% Tris Glycine gel, as above, to identify the fractions with GST-cMET. Fractions are pooled and the $OD_{280}$ is read with the column buffer used as the blank.

A Kinase reaction Buffer is prepared as follows:

| | | | Per 1 L |
|---|---|---|---|
| 60 mN HEPES $p$H 7.4 | 1 M stock | 16.7 X | 60 mL |
| 50 mM NaCl | 5 M stock | 100 X | 10 mL |
| 20 mM $MgCl_2$ | 1 M stock | 50 X | 20 mL |
| 5 mM $MnCl_2$ | 1 M stock | 200 X | 5 mL |

When the assay is carried out, freshly add:

| | | |
|---|---|---|
| 2 mM DTT | 1 M stock | 500 X |
| 0.05% BSA | 5% stock | 100 X |
| 0.1 mM $Na_3OV_4$ | 0.1 M stock | 1000 X |

The HTRF buffer contains:

50 mM Tris-HCl (pH 7.5), 100 mM NaCl, 0.1% BSA, 0.05% Tween 20.5 mM EDTA

Fresh add SA-APC (PJ25S Phycolink Streptavidin-Allophycocyanin Conjugate, Prozyme Inc.) and Eu-PT66 (Eu-W1024 labeled anti-phosphorotyrosine antibody PT66, AD0069, Lot 168465, Perkin-Elmer Inc.) to reach the final concentration:

0.1 nM final Eu-PT66

11 nM final SA-APC

Methods:

1. Dilute GST-cMet (P) enzyme in kinase buffer as follows: Prepare 8 nM GST-cMet (P) working solution (7.32 μM to 8 nM, 915×, 10 μL to 9.15 mL). In a 96 well clear plate [Costar # 3365] add 100 μL in eleven columns, in one column add 100 μL kinase reaction buffer alone.

2. Assay plate preparation:

Use Biomek FX to transfer 10 μL 8 nM GST-cMet (P) enzyme, 48.4 μL kinase reaction buffer, 1.6 μL compound (in DMSO) (Start concentration at 10 mM, 1 mM and 0.1 mM, sequential dilution 1:3 to reach 10 test points) in a 96 well costar clear plate [Costar # 3365], mix several times. Then incubate the plate at RT for 30 min.

3. Prepare Gastrin and ATP working solution in kinase reaction buffer as follows:

Prepare 4 µM Gastrin and 16 µM ATP working solution

|  |  | Per 10 mL |
| --- | --- | --- |
| Gastrin 4 µM stock | (500 µM to 4 µM, 125 X) | 80 µL |
| ATP 16 µM stock | (1000 µM to 16 µM, 62.5 X) | 160 µL |

Use Biomek FX to add 20 µl ATP and Gastrin working solution to the assay plate to start reaction, incubate the plate at RT for 1 h.

4. Transfer 5 µL reaction product at the end of 1 h into 80 µL HTRF buffer in black plate [Costar # 3356], read on Discover after 30 min incubation.

Assay Condition Summary:

| $K_M$ ATP * | 6 µM |
| --- | --- |
| [ATP] | 4 µM |
| $K_M$ Gastrin/p(EY) | 3.8 µM |
| [gastrin] | 1 µM |
| [enzyme] | 1 nM |

$K_M$ ATP, $K_M$ gastrin for various enzymes were determined by HTRF/$^{33}$P labeling and HTRF methods.

Examples 1-3, 6, 8-31, 33-37, 37b, 37d, 37f, 37h-37j, 37o-37p, 37s-37v, 37x-37z, 37ab-37ah, 39-43, 43a-43i, 43k-43n, 45-47, 49, 51-52, 55-56, 60, 63-64, 66-69, 71-73, 75, 78-81, 83 and 86 exhibited activity with IC$_{50}$ values less than 0.5 µM.

c-Met Cell-Based Autophosphorylation Assay

Human PC3 and mouse CT26 cells are available obtained from ATCC. The cells were cultured in a growth medium containing RPMI 1640, penicillin/streptomycin/glutamine (1x) and 5% FBS. $2 \times 10^4$ cells in medium were plated per well in a 96 well plate and incubated at 37° C. overnight. The cells were serum-starved by replacing the growth media with basic medium (DMEM low glucose+0.1 BSA, 120 µL per well) at 37° C. for 16 h. Compounds (either 1 mM and 0.2 mM) in 100% DMSO were serially diluted (1:3) 3333 fold on a 96 well plate, diluting 1:3 with DMSO from column 1 to 11 (columns 6 and 12 receive no compound). Compound samples (2.4 µL per well) were diluted with basic medium (240 µL) in a 96 well plate. The cells were washed once with basic medium (GIBCO, DMEM 11885-076) then compound solution was added (100 µL). The cells were incubated at 37° C. for 1 h. A (2 mg/mL) solution of CHO-HGF (7.5 µL) was diluted with 30 mL basic medium to provide a final concentration of 500 ng/mL. This HGF-containing media (120 µL) was transferred to a 96 well plate. Compounds (1.2 µL) was added to the HGF-containing media and mixed well. The mixture of media/HGF/compound (100 µL) was added to the cells (final HGF concentration –250 ng/mL) then incubated at 37° C. for 10 min. A cell lysate buffer (20 mL) was prepared containing 1% Triton X-100, 50 mM Tris pH 8.0, 100 mM NaCl, Protease inhibitor (Sigma, #P-8340) 200 µL, Roche Protease inhibitor (Complete, # 1-697-498) 2 tablets, Phosphatase Inhibitor II (Sigma, #P-5726) 200 µL, and a sodium vanadate solution (containing 900 µL PBS, 100 µL 300 mM NaVO$_3$, 6 µL H$_2$O$_2$ (30% stock) and stirred at RT for 15 min)(90 µL). The cells were washed once with ice cold 1xPBS (GIBCO, #14190-136), then lysis buffer (60 µL) was added and the cells were incubated on ice for 20 min.

The IGEN assay was performed as follows: Dynabeads M-280 streptavidin beads were pre-incubated with biotinylated anti-human HGFR (240 µL anti-human-HGFR (R&D system, BAF527 or BAF328) @ 100 µg/mL+360 µL Beads (IGEN #10029+5.4 µL buffer—PBS/1% BSA/0.1% Tween20) by rotating for 30 min at RT. Antibody beads (25 µL) were transferred to a 96 well plate. Cell lysate solution (25 µL) was transferred added and the plate was shaken at RT for 1 h. Anti-phosphotyrosine 4G10 (Upstate 05-321) (19.7 µL antibody+6 mL 1xPBS) (12.5 µL) was added to each well, then incubated for 1 h at RT. Anti-mouse IgG OR$^1$-Tag (ORIGEN #110087) (24 µL Antibody+6 mL buffer) (12.5 µL) was added to each well, then incubated at RT for 30 min. 1xPBS (175 µL) was added to each well and the electrochemiluminescence was read by an IGEN M8. Raw data was analyzed using a 4-parameter fit equation in XLFit. IC$_{50}$ values are then determined using Grafit software. Examples 1, 6, 8-10, 13, 15, 17, 20-22, 28, 30, 35-37, 37s, 37u, 37y, 37ab, 37ac-37ae, 37ah, 43c, 43f, 64, 67, 73, 75, 78 and 80 exhibited activity in PC3 cells with IC$_{50}$ values less than 1.0 µM. Examples 1, 6, 9-10, 13, 15, 17, 20-22, 28, 30, 35-37, 37s, 37u, 37y, 37ac-37ae, 37ah, 43c, 43f, 64, 67, 73, 75 and 80 exhibited activity in CT26 cells with IC$_{50}$ values less than 1.0 µM.

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+antibiotics, and spun at 1000 rpm for 10 min. Prior to centrifugation of the cells, a small amount is collected for a cell count. After centrifugation, the medium is discarded, and the cells are resuspended in the appropriate volume of DMEM+10% FBS+antibiotics to achieve a concentration of $3 \times 10^5$ cells/mL. Another cell count is performed to confirm the cell concentration. The cells are diluted to $3 \times 10^4$ cells/mL in DMEM+10% FBS+antibiotics, and 100 µL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 µL of each compound dilution are diluted further in a total of 1 mL DMEM+10% FBS+antibiotics (400x dilution). Medium containing 0.25% DMSO is also prepared for the 0 µM compound sample. At the 22 h timepoint, the medium is removed from the cells, and 100 µL of each compound dilution is added. The cells are incubated at 37° C. for 2-3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 µL of each will be added to the cells (110 µL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. $IC_{50}$ values are then determined.

Rat Corneal Neovascularization Micropocket Model

In Life Aspects: Female Sprague Dawley rats weighing approximately 250 g were randomized into one of five treatment groups. Pretreatment with the vehicle or compound was administered orally, 24 h prior to surgery and continued once a day for seven additional days. On the day of surgery, the rats were temporarily anesthetized in an Isofluorane gas chamber (delivering 2.5 L/min oxygen+5% Isofluorane). An otoscope was then placed inside the mouth of the animal to visualize the vocal cords. A tip-blunted wire was advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) was connected to the endotracheal tube to deliver a mixture of oxygen and 3% Isofluorane. Upon achieving deep anesthesia, the whiskers were cut short and the eye areas and eyes gently washed with Betadine soap and rinsed with sterile saline. The corneas were irrigated with one to two drops of Proparacaine HCl ophthalmic topical anesthetic solution (0.5%) (Bausch and Lomb Pharmaceuticals, Tampa Fla.). The rat was then positioned under the dissecting microscope and the corneal surface brought into focus. A vertical incision was made on the midline of the cornea using a diamond blade knife. A pocket was created by using fine scissors to separate the connective tissue layers of the stroma, tunneling towards the limbus of the eye. The distance between the apex of the pocket and the limbus was approximately 1.5 mm. After the pocket had been made, the soaked nitrocellulose disk filter (Gelman Sciences, Ann Arbor Mich.) was inserted under the lip of the pocket. This surgical procedure was performed on both eyes. rHu-bFGF soaked disks were placed into the right eye, and the rHu-VEGF soaked disks were placed into the left eye. Vehicle soaked disks were placed in both eyes. The disk was pushed into position at the desired distance from the limbal vessels. Ophthalmic antibiotic ointment was applied to the eye to prevent drying and infection. After seven days, the rats were euthanized by $CO_2$ asphyxiation, and the eyes enucleated. The retinal hemisphere of the eye was windowed to facilitate fixation, and the eye placed into formalin overnight.

Post Mortem Aspects: After 24 h in fixative, the corneal region of interest was dissected out from the eye, using fine forceps and a razorblade. The retinal hemisphere was trimmed off and the lens extracted and discarded. The corneal dome was bisected and the superfluous cornea trimmed off. The iris, conjunctiva and associated limbal glands were then carefully teased away. Final cuts were made to generate a square 3×3 mm containing the disk, the limbus, and the entire zone of neovascularization.

Gross Image Recording: The corneal specimens were digitally photographed using a Sony CatsEye DKC5000 camera (A.G. Heinz, Irvine Calif.) mounted on a Nikon SMZ-U stereo microscope (A.G. Heinz). The corneas were submerged in distilled water and photographed via trans-illumination at approximately 5.0 diameters magnification.

Image analysis: Numerical endpoints were generated using digital micrographs collected from the whole mount corneas after trimming and were used for image analysis on the Metamorph image analysis system (Universal Imaging Corporation, West Chester Pa.). Three measurements were taken: Disk placement distance from the limbus, number of vessels intersecting a 2.0 mm perpendicular line at the midpoint of the disk placement distance, and percent blood vessel area of the diffusion determined by thresholding.

General Formulations:

0.1% BSA in PBS vehicle: 0.025 g of BSA was added to 25.0 mL of sterile 1× phosphate buffered saline, gently shaken until fully dissolved, and filtered at 0.2 µM. Individual 1.0 mL samples were aliquoted into 25 single-use vials, and stored at −20° C. until use. For the rHu-bFGF disks, a vial of this 0.1% BSA solution was allowed to thaw at room temperature. Once thawed, 10 µL of a 100 mM stock solution of DTT was added to the 1 ml BSA vial to yield a final concentration of 1 mM DTT in 0.1% BSA.

rHu-VEGF Dilutions: Prior to the disk implant surgery, 23.8 µL of the 0.1% BSA vehicle above was added to a 10 µg rHu-VEGF lyophilized vial yielding a final concentration of 10 µM.

rHu-bFGF: Stock concentration of 180 ng/µL: R&D rHu-bFGF: Added 139 µL of the appropriate vehicle above to the 25 µg vial lyophilized vial. 13.3 µL of the [180 ng/µL] stock vial and added 26.6 µL of vehicle to yield a final concentration of 3.75 µM concentration.

Nitro-cellulose disk preparation: The tip of a 20-gauge needle was cut off square and beveled with emery paper to create a punch. This tip was then used to cut out≅0.5 mm diameter disks from a nitrocellulose filter paper sheet (Gelman Sciences). Prepared disks were then placed into Eppendorf microfuge tubes containing solutions of either 0.1% BSA in PBS vehicle, 10 µM rHu-VEGF (R&D Systems, Minneapolis, Minn.), or 3.75 µM rHu-bFGF (R&D Systems, Minneapolis, Minn.) and allowed to soak for 45-60 min before use. Each nitrocellulose filter disk absorbs approximately 0.1 µL of solution.

In the rat micropocket assay, compounds of the present invention will inhibit angiogenesis at a dose of less than 50 mg/kg/day.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention will be active at doses less than 150 mpk.

Tumor Models

Human glioma tumor cells (U87MG cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control. Compounds of the present invention will be active at 150 mpk.

Human gastric adenocarcinoma tumor cells (MKN45 cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control. Compounds of the present invention will be active at 150 mpk.

Formulations

Also embraced within this invention is a class of pharmaceutical compositions comprising the active compounds of Formula I-V in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.01 and about 50 mg/kg, and more preferably about 0.01 and about 30 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxological effects are expected when compounds of the present invention are administered in accordance with the present invention.

All mentioned references, patents, applications and publications, are hereby incorporated by reference in their entirety, as if here written.

What is claimed is:

1. A compound of Formula I $$R^1-X-W-A-Y-R \qquad (I)$$

wherein R is selected from substituted or unsubstituted phenyl, substituted or unsubstituted cycloalkyl, substituted or unsubstituted cycloalkenyl, H, —OH, alkylamino, substituted or unsubstituted alkyl, and substituted or unsubstituted alkenyl and substituted or unsubstituted alkynyl;

wherein $R^1$ is

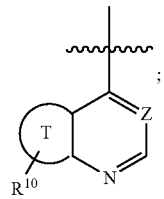

wherein ring T is phenyl; wherein Z is CH; wherein $R^{10}$ is one or more substituents selected from $C_{1-6}$-alkoxy, $C_{1-6}$-haloalkoxy, $C_{1-6}$-alkylamino-$C_{1-6}$-alkoxy, aryl-$C_{1-6}$-alkoxy, heterocyclyl-$C_{1-6}$-alkoxy, cycloalkyl-$C_{1-6}$-alkoxy, heterocyclyl-$C_{1-6}$-(hydroxyalkoxy), cycloalkyl-$C_{1-6}$-(hydroxyalkoxy), aryl-$C_{1-6}$-(hydroxyalkoxy), $C_{1-6}$-alkoxyalkoxy, aryloxy-$C_{1-6}$-alkoxy, heterocyclyloxy-$C_{1-6}$-alkoxy, cycloalkyloxy-$C_{1-6}$-alkoxy, aryloxy, heterocyclyloxy, and cycloalkyloxy;

wherein W is an substituted or unsubstituted phenyl;
wherein A is an substituted or unsubstituted pyrimidine or pyridazine ring;
wherein X is selected from O, S, $NR^2$ and $CR^3R^4$;
wherein Y is a direct bond;
wherein $R^a$ is selected from H, alkyl, heterocyclyl, aryl, arylalkyl, heterocyclylalkyl, cycloalkyl, cycloalkylalkyl, alkenyl, alkynyl, $R^5R^5N$—(C=O)—, and $R^5$—(=O)—; wherein $R^a$ is optionally substituted;
wherein $R^2$ is selected from H, alkyl, haloalkyl, aryl, heterocyclyl, arylalkyl, heterocyclylalkyl, cycloalkyl, cycloalkylalkyl, hydroxyalkyl, alkoxyalkyl, alkylaminoalkyl, alkylthioalkyl, alkenyl, alkynyl and $R^5$-carbonyl;
wherein $R^3$ and $R^4$ is each independently selected from H, alkyl, aryl, heterocyclyl, arylalkyl, heterocyclylalkyl, haloalkyl, cycloalkyl, cycloalkylalkyl, $R^6$ and alkyl substituted with $R^6$;
wherein $R^5$ is selected from H, alkyl, haloalkyl, hydroxyalkyl, alkoxyalkyl, alkylaminoalkyl, alkylthioalkyl, arylalkyl, heterocyclylalkyl, cycloalkylalkyl, aryl, heterocyclyl, alkenyl, alkynyl and cycloalkyl;
wherein $R^{5a}$ is selected from H, alkyl, haloalkyl, arylalkyl, heterocyclylalkyl, cycloalkylalkyl, aryl, heterocyclyl, hydroxyalkyl, alkoxyalkyl, alkylaminoalkyl, alkylthioalkyl, alkenyl, alkynyl and cycloalkyl;
wherein $R^6$ is selected from cyano, $—OR^2$, $—SR^2$, halo, $—SO_2R^2$, $—C(=O)R^2$, $—SO_2NR^2R^5$, $—NR^5C(=O)OR^2$, $—NR^5C(=O)NR^5R^2$, $NR^5C(=O)R^2$, $CO_2R^2$, $C(=O)NR^2R^5$ and $—NR^2R^5$;
wherein $R^{6a}$ is selected from cyano, $—OR^2$, $—SR^2$, halo, $—SO_2R^2$, $—C(=O)R^2$, $—SO_2NR^2R^5$, $—NR^5C(=O)OR^2$, $—NR^5C(=O)NR^5R^2$, $—NR^5C(=O)R^2$, $—CO_2R^2$, $—C(=O)NR^2R^5$ and $—NR^2R^5$;
wherein each alkyl, aryl, heteroaryl, cycloalkyl, alkenyl, alkynyl, heterocyclyl, and alkoxy moiety of any R, $R^1$, $R^2$, $R^3$, $R^4$, $R^5$, and $R^a$ is optionally substituted with one or more groups selected from halo, $R^{6a}$, $—NH_2$, $—OR^{5a}$, $—CO_2H$, $(C_1-C_6)$alkylamino, $(C_1-C_6)$alkyl, $(C_3-C_6)$cycloalkyl, $(C_1-C_6)$haloalkyl, di$(C_1-C_6)$alkylamino, $(C_1-C_6)$alkylamino-$(C_1-C_6)$alkyl, $(C_1-C_6)$hydroxyalkylamino, $(C_1-C_6)$alkylamino-$(C_1-C_6)$alkylamino, phenyl, and heterocyclyl;
and pharmaceutically acceptable salts thereof.

2. Compound of claim 1,

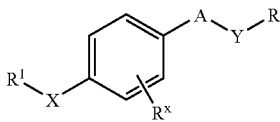

wherein R is selected from substituted or unsubstituted phenyl, substituted or unsubstituted cycloalkyl, substituted or unsubstituted cycloalkenyl, H, —OH, alkylamino, substituted or unsubstituted alkyl, and substituted or unsubstituted alkenyl and substituted or unsubstituted alkynyl,
and pharmaceutically acceptable salts thereof.

3. Compound of claim 2 wherein R is selected from H, phenyl, 4-6 membered cycloalkyl, $C_{1-6}$-alkyl, $C_{2-6}$-alkenyl and $C_{2-6}$-alkynyl; wherein R is substituted or unsubstituted.

4. Compound of claim 2 wherein R is optionally substituted phenyl.

5. Compound of claim 2 wherein R is 4-6 membered cycloalkyl selected from cyclopropyl, cyclobutyl, cyclopentyl and cyclohexyl.

6. Compound of claim 2 wherein R is selected from methyl, ethyl, propyl, butyl, isobutyl, tert-butyl, 3,3-dimethylpropyl and pentyl.

7. Compound of claim 1 wherein A is selected from

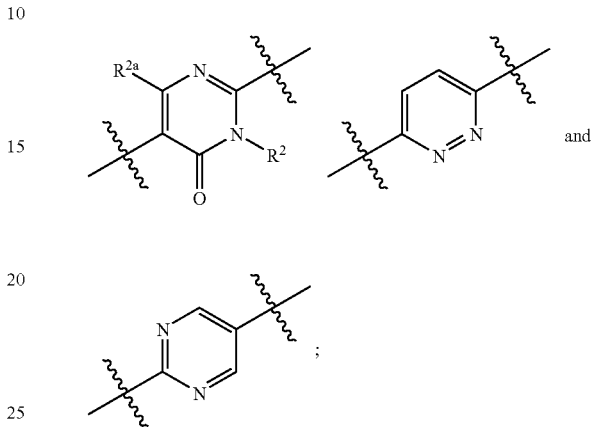

wherein $R^2$ is selected from H, $C_{1-3}$-alkyl, aryl-$C_{1-3}$-alkyl, and heterocyclyl-$C_{1-3}$-alkyl; and wherein $R^{2a}$ is selected from H and methyl;
and pharmaceutically acceptable salts thereof.

8. Compound of claim 2 wherein A is

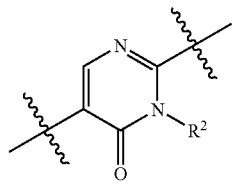

9. Compound of claim 2 wherein $R^1$ is selected from

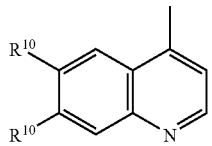

and wherein $R^{10}$ is selected from $C_{1-3}$-alkoxy, $C_{1-3}$-alkylamino-$C_{1-3}$-alkoxy, 5-6 membered heterocyclyl-$C_{1-3}$-alkoxy, $C_{4-6}$-cycloalkyl-$C_{1-3}$-alkoxy, 5-6 membered heterocyclyl-$C_{1-3}$-(hydroxyalkoxy), $C_{3-6}$-cycloalkyl-$C_{1-3}$-(hydroxyalkoxy), $C_{1-2}$-alkoxy-$C_{1-3}$-alkoxy, phenyloxy-$C_{1-3}$alkoxy, 5-6 membered heterocyclyloxy-$C_{1-3}$-alkoxy, cycloalkyloxy-$C_{1-3}$-alkoxy, 5-6 membered heterocyclyloxy, and $C_{3-6}$-cycloalkyloxy.

10. Compound of claim 2 wherein $R^1$ is selected from 6,7-dimethoxy-4-quinolinyl, 6-methoxy-7-(dimethylaminopropoxy)-4-quinolinyl, 6-methoxy-7-(3-(morpholin-4-yl)propoxy)-4-quinolinyl, 6-methoxy-7-(3-(pyrrolidin-1-yl)

propoxy)-4-quinolinyl, 6-methoxy-7-(2-hydroxy-3-(morpholin-4-yl)propoxy)-4-quinolinyl, 6-methoxy-7-(3-(1,2,4-triazol-1-yl)propoxy)-4-quinolinyl, 6-methoxy-7-(3-(4-methylpiperazin-1-yl)propoxy)-4-quinolinyl, 6-methoxy-7-(3-(piperidin-4-yl)propoxy)-4-quinolinyl, 6,7-dimethoxy-4-quinazolinyl and 6-methoxy-7-(dimethylaminopropoxy)-4-quinazolinyl.

11. Compound of claim 2 wherein R is selected from H, ethyl, isopropyl, $(CH_3)_3CCH_2$—, ethenyl, and an unsubstituted or substituted ring selected from phenyl, cyclobutyl, cyclopentyl, cyclohexyl, wherein X is —O—; and; and pharmaceutically acceptable salts thereof.

12. Compound of claim 2 wherein W is phenyl; and pharmaceutically acceptable salts thereof.

13. A compound of Formula II

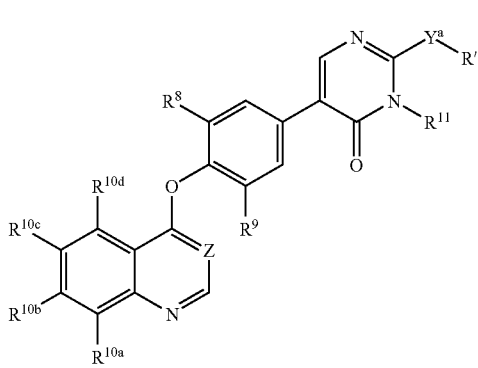

wherein $Y^a$ is selected from a bond,
wherein Z is CH;
wherein R' is selected from H, $C_{1-6}$-alkyl, di-$C_{1-3}$-alkylamino and an unsubstituted or substituted ring selected from phenyl;
wherein $R^8$ is selected from H, fluoro, chloro and methyl;
wherein $R^9$ is selected from H, methyl and fluoro;
wherein $R^{10a}$, $R^{10b}$, $R^{10c}$ and $R^{10d}$ is each independently selected from $C_{1-3}$-alkoxy, $C_{1-3}$-alkylamino-$C_{1-3}$-alkoxy, 5-6 membered heterocyclyl-$C_{1-3}$-alkoxy, $C_{4-6}$-cycloalkyl-$C_{1-3}$-alkoxy, 5-6 membered heterocyclyl-$C_{1-3}$-(hydroxyalkoxy), $C_{3-6}$-cycloalkyl-$C_{1-3}$-(hydroxyalkoxy), phenyl-$C_{1-3}$-(hydroxyalkoxy), $C_{1-2}$-alkoxy-$C_{1-3}$-alkoxy, phenyloxy-$C_{1-3}$alkoxy, 5-6 membered heterocyclyloxy-$C_{1-4}$-alkoxy, cycloalkyloxy-$C_{1-3}$-alkoxy, 5-6 membered heterocyclyloxy, and $C_{3-6}$-cycloalkyloxy; and
wherein $R^{11}$ is H or methyl;
and pharmaceutically acceptable salts thereof.

14. Compound of claim 13, wherein R' is selected from ethyl, isopropyl, isobutyl, $(CH_3)_3CCH_2$—, dimethylamino, and an unsubstituted or substituted ring selected from phenyl, cyclopropyl, cyclobutyl, cyclopentyl, cyclohexyl, 1-pyrrolidinyl, 2-pyrrolyl, 5-imidazolyl, 5-pyrazolyl, 2-pyrazinyl, 4-pyrimidinyl, 2-pyridyl, 3-pyridyl, 4-pyridyl, 8-quinolinyl, 2,3-dihydrobenzofur-7-yl, 2,3-dihydro-1,4-benzodioxin-5-yl, 1,3-benzodioxol-4-yl, 4-isoxazolyl, 3-isothiazolyl, 5-oxazolyl, 4-thiazolyl, 5-thiazolyl, 2-furanyl, 3-furanyl, 3-thienyl and 2-thienyl; and
wherein $R^{10a}$ and $R^{10d}$ are both H; and pharmaceutically acceptable salts thereof.

15. Compound of claim 13 wherein $R^{11}$ is methyl; and pharmaceutically acceptable salts thereof.

16. Compound of claim 13 wherein R' is selected from isobutyl, $(CH_3)_3CCH_2$—, dimethylamino, cyclopropyl, cyclopentyl, 1-pyrrolidinyl, phenyl, 2-fluorophenyl, 3-fluorophenyl, 4-fluorophenyl, 4-methylphenyl, 4-trifluoromethylphenyl, and 4-(dimethylamino)phenyl; and pharmaceutically acceptable salts thereof.

17. Compound of claim 13 wherein $R^8$ is H; and pharmaceutically acceptable salts thereof.

18. Compound of claim 13 wherein $R^9$ is H, methyl or fluoro; and pharmaceutically acceptable salts thereof.

19. Compound of claim 13 and pharmaceutically acceptable salts thereof; wherein $R^{10a}$ and $R^{10d}$ are both H; and wherein $R^{10b}$ and $R^{10c}$ are independently selected from 4-morpholinopropoxy, 2-hydroxy-3-morpholin-4-yl-propoxy, pyrrolidin-1-ylpropoxy, 1-pyrrolidinylethoxy, 4-piperidinyloxypropoxy, (4-methylpiperazin-1-yl)propoxy, 3-(4-methylpiperazin-1-yl)propoxy, 3-(1,2,4-triazol-1-yl) propoxy, triazinylpropoxy, 3-(piperidin-4-yl)propoxy, dimethylaminoethoxy, dimethylaminopropoxy and methoxy.

20. A compound of Formula V

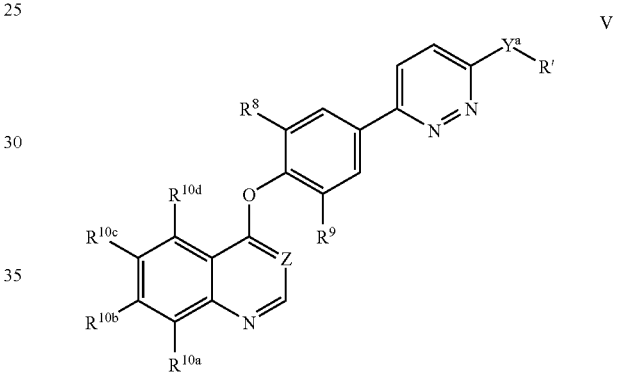

wherein $Y^a$ is a direct bond,
wherein Z is CH;
wherein R' is selected from H, $C_{1-6}$-alkyl, di-$C_{1-3}$-alkylamino and an unsubstituted or substituted phenyl, $C_{3-6}$-cycloalkyl;
wherein $R^8$ is selected from H, fluoro, chloro and methyl;
wherein $R^9$ is selected from H, methyl and fluoro; and
wherein $R^{10a}$, $R^{10b}$, $R^{10c}$ and $R^{10d}$ is each independently selected from $C_{1-3}$-alkoxy, $C_{1-3}$-alkylamino-$C_{1-3}$-alkoxy, 5-6 membered heterocyclyl-$C_{1-3}$-alkoxy, $C_{4-6}$-cycloalkyl-$C_{1-3}$-alkoxy, 5-6 membered heterocyclyl-$C_{1-3}$- (hydroxyalkoxy), $C_{3-6}$-cycloalkyl-$C_{1-3}$-(hydroxyalkoxy), $C_{1-2}$-alkoxy-$C_{1-3}$-alkoxy, phenyloxy-$C_{1-3}$ alkoxy, 5-6 membered heterocyclyloxy-$C_{1q}$-alkoxy, cycloalkyloxy-$C_{1-3}$-alkoxy, 5-6 membered heterocyclyloxy, and
$C_{3-6}$-cycloalkyloxy;
and pharmaceutically acceptable salts thereof.

21. A pharmaceutical composition comprising a pharmaceutically-acceptable carrier and a compound as in any of claims 1-4, 5-7, 8, 9-10, 11-12, 13-19, 20.

22. A method of treating lung, gastric, hemangioblastoma, colon, liver, and renal cancer in a subject, said method comprising administering an effective amount of a compound of claim 1.

23. The method of claim 22 comprising a combination with a compound selected from antibiotic-type agents, alkylating agents, antimetabolite agents, hormonal agents, immunological agents, interferon-type agents and miscellaneous agents.

24. A method of reducing metastasis in a tumor in a subject, said method comprising administering an effective amount of a compound of claim 1.

25. A method of reducing tumor size in a subject, said method comprising administering an effective amount of a compound of claim 1.

* * * * *

UNITED STATES PATENT AND TRADEMARK OFFICE
CERTIFICATE OF CORRECTION

PATENT NO. : 7,652,009 B2  Page 1 of 1
APPLICATION NO. : 11/289659
DATED : January 26, 2010
INVENTOR(S) : Tae-Seong Kim et al.

It is certified that error appears in the above-identified patent and that said Letters Patent is hereby corrected as shown below:

Title Page; item (73);
Column 1, Assignee's Name: change from "Amgem Inc." to --Amgen Inc.--

Signed and Sealed this
Twelfth Day of April, 2011

David J. Kappos
*Director of the United States Patent and Trademark Office*